United States Patent
Klaus et al.

(10) Patent No.: US 9,775,902 B2
(45) Date of Patent: Oct. 3, 2017

(54) COMPOUNDS AND METHODS FOR TREATMENT OF STROKE

(75) Inventors: Stephen J. Klaus, San Francisco, MA (US); Ingrid Langsetmo Parobok, Port Angeles, WA (US); Christopher T. Jacob, San Diego, CA (US)

(73) Assignee: FIBROGEN, INC, San Francisco, CA (US)

( * ) Notice: Subject to any disclaimer, the term of this patent is extended or adjusted under 35 U.S.C. 154(b) by 925 days.

(21) Appl. No.: 13/180,262

(22) Filed: Jul. 11, 2011

(65) Prior Publication Data

US 2011/0263644 A1  Oct. 27, 2011

Related U.S. Application Data

(63) Continuation of application No. 11/704,535, filed on Feb. 8, 2007, now abandoned.

(60) Provisional application No. 60/774,950, filed on Feb. 16, 2006.

(51) Int. Cl.
*A61K 31/121* (2006.01)
*A61K 31/194* (2006.01)
*A61K 45/06* (2006.01)
*A61K 38/49* (2006.01)

(52) U.S. Cl.
CPC ............ *A61K 45/06* (2013.01); *A61K 31/121* (2013.01); *A61K 31/194* (2013.01); *A61K 38/49* (2013.01)

(58) Field of Classification Search
CPC .............................. A61K 31/121; A61K 31/194
USPC .......................................................... 514/574
See application file for complete search history.

(56) References Cited

U.S. PATENT DOCUMENTS

| | | | |
|---|---|---|---|
| 5,942,434 A | 8/1999 | Ratcliffe et al. | |
| 7,928,120 B2 * | 4/2011 | Arend et al. | ................. 514/307 |
| 2002/0137758 A1 * | 9/2002 | Grotta et al. | ............ 514/263.31 |
| 2003/0176317 A1 | 9/2003 | Guenzkler-Pukall et al. | |
| 2006/0194756 A1 | 8/2006 | Borea et al. | |
| 2007/0092500 A1 | 4/2007 | Frey et al. | |

FOREIGN PATENT DOCUMENTS

| | | |
|---|---|---|
| WO | WO-00/69908 A1 | 11/2000 |
| WO | WO-02/074249 A2 | 9/2002 |
| WO | WO-02/074981 A2 | 9/2002 |
| WO | WO-03/049686 A3 | 6/2003 |
| WO | WO-03/053997 A2 | 7/2003 |
| WO | WO-2004/108121 A1 | 12/2004 |
| WO | WO-2004/108681 A1 | 12/2004 |
| WO | WO-2005/094236 | 10/2005 |
| WO | WO-2006/020727 A2 | 2/2006 |
| WO | WO 2006/094292 A2 | 9/2006 |
| WO | WO-2006/138511 A2 | 12/2006 |

OTHER PUBLICATIONS

Ivan, Mircea, et al., "HIFα Targeted for VHL-Mediated Destruction by Proline Hydroxylation: Implications for O2 Sensing," Science (2001) 292:464-468.

Ivan, Mircea, et al., "Biochemical Purification and Pharmacological Inhibition of a Mammalian Prolyl Hydroxylase Acting on Hypoxia-Inducible Factor," PNAS (2002) 99(21):13459-13464.

Ratan, Rajiv R., et al., "Translation of Ischemic Preconditioning to the Patient. Prolyl hydroxylase inhibition and hypoxia inducible factor-1 as novel targets for stroke therapy," Stroke (2004) 35[Suppl 1]:2687-89.

\* cited by examiner

*Primary Examiner* — Yong Chong

(57) ABSTRACT

The present invention relates to methods and agents useful for the treatment of stroke, including ischemic stroke and hemorrhagic stroke. In particular, methods and agents for treating stroke in a subject are provided, wherein the agent is administered prior to diagnosis of the stroke as an ischemic stroke or a hemorrhagic stroke.

10 Claims, 5 Drawing Sheets

COMPOUNDS AND METHODS FOR TREATMENT OF STROKE

This application is a continuation of U.S. application Ser. No. 11/704,535 filed 8 Feb. 2007, which claims the benefit of U.S. Provisional Application Ser. No. 60/774,950, filed on 16 Feb. 2006, each of which is incorporated by reference herein in its entirety.

FIELD OF THE INVENTION

The present invention relates to methods and agents useful for the treatment of ischemic disorders. In particular, methods and agents of the present invention can be used for treatment of stroke, including ischemic stroke and hemorrhagic stroke.

BACKGROUND OF THE INVENTION

Stroke

Approximately 15 million people worldwide suffer a stroke each year, resulting in death or sensorimotor and other defects. Stroke remains the third most common cause of death in the industrialized world behind heart disease and cancer. There are two forms of stroke: ischemic stoke, caused by a blood clot that blocks or prevents the flow of blood, and hemorrhagic stroke, caused by bleeding into or around the brain. Ischemic stroke accounts for approximately 80-86% of all stroke cases. Current pharmacotherapy for ischemic stroke is limited.

Administration of thrombolytic agents, such as tissue plasminogen activator (tPA), which dissolve blood clots and thus restore blood flow to affected regions, has limited applicability. In particular, administration of tPA is only effective if given within three hours from the time of stroke onset. This three-hour therapeutic window must include time for diagnosis, as the use of tPA for treatment of stroke is limited to that of ischemic stroke, and cannot be administered to a patient having had a hemorrhagic stroke. The use of tPA for treatment of ischemic stroke has other limitations, including that not all clinicians are adequately trained to deliver tPA, and that tPA has also been associated with extravascular deleterious effects, including hemmorhagic transformation, microvascular dysfunction, and excitotoxic neuronal damage.

Moreover, use of thrombolytic agents, such as tPA, as well as other existing stroke therapies, target only a specific subset of deleterious symptoms associated with or resulting from stroke, and therefore fail to provide a complete therapeutic approach for addressing both the immediate and long-term consequences following a stroke. Additionally, such therapies are often of high cost and have limited modes of administration.

Therefore, a need exists for a therapy that is effective in the treatment all types of stroke, i.e., both ischemic strokes and hemorrhagic strokes. There is also a need for a therapy that is effective in the treatment of stroke even when administered beyond the therapeutic window of current treatments. There is also a need for a therapy that upregulates in a coordinated fashion protective factors corresponding to the full range of symptoms resulting from the stroke. Preferably, the therapy would be of lower cost than existing therapies and allow for convenient and timely administration.

Ischemia

Ischemia, reduction in blood flow, can be caused by the obstruction or occlusion of an artery or vein by a blood clot (thrombus) or by any foreign circulating matter (embolus), or by a vascular disorder such as atherosclerosis. Reduction in blood flow can have a sudden onset and short duration (acute ischemia), or can have a slow onset with long duration or frequent recurrence (chronic ischemia). Acute ischemia is often associated with regional, irreversible tissue necrosis (an infarct), whereas chronic ischemia is often associated with transient hypoxic tissue injury. If the decrease in perfusion is prolonged or severe, however, chronic ischemia can also be associated with an infarct. Infarctions commonly occur in the spleen, kidney, lungs, brain, and heart, producing disorders such as intestinal infarction, pulmonary infarction, ischemic stroke, and myocardial infarction.

Ischemic disorders are a major cause of morbidity and mortality. For example, cardiovascular disease is associated with over 15 million deaths every year and is responsible for 30% of deaths worldwide. Among the various cardiovascular diseases, ischemic heart disease and cerebrovascular diseases cause approximately 17% of deaths.

Currently, treatment of ischemic disorders is focused on relief of symptoms and treatment of causative disorders. For example, treatments for myocardial infarction include nitroglycerin and analgesics to control pain and relieve the workload of the heart. Other medications, including digoxin, diuretics, amrinone, beta-blockers, lipid-lowering agents and angiotensin-converting enzyme inhibitors, are used to stabilize the condition, but none of these therapies directly address the tissue damage produced by the ischemia.

Due to deficiencies in current treatments, there remains a need for methods that are effective for treating ischemic disorders, such as, for example, cerebrovascular ischemia (including ischemic stroke), cardiovascular ischemia, peripheral vascular ischemia, and renal ischemia.

SUMMARY OF THE INVENTION

The present invention provides methods for treating stroke in a subject in need. In various embodiments, the method comprises administering to the subject an effective amount of an agent that inhibits hypoxia inducible factor (HIF) hydroxylase activity, wherein the agent is administered prior to diagnosis of the stroke as an ischemic stroke or a hemorrhagic stroke.

An advantage of the present methods over current treatment methods for stroke is that methods of the present invention can be applied to situations in which a subject has had a stroke or is suspected of having had a stroke prior to diagnosis of the stroke as an ischemic stroke or a hemorrhagic stroke. The consequent elimination of the need to diagnose a stroke as being an ischemic stroke or a hemorrhagic stroke reduces the delay between the time from stroke onset to appropriate treatment.

The methods of the present invention may be applied more than three hours after the time from stroke onset, thus extending the therapeutic window beyond that provided by existing treatments. Accordingly, in various embodiments, methods of the present invention may be carried out more than 3 hours, more than 3½ hours, more than 4 hours, more than 4½ hours, more than 5 hours, more than 5½ hours, more than 6 hours, more than 7 hours, or more than 8 hours after the time of stroke onset.

The invention further provides methods and agents useful for treating or ameliorating brain tissue damage associated with stroke in a subject, the method comprising administering to the subject an effective amount of an agent that inhibits hypoxia inducible factor (HIF) hydroxylase activity. In various embodiments, brain tissue damage is infarct volume, edema, a lesion, neuronal degeneration, or brain tissue loss.

In other embodiments, the present invention provides methods and agents for treating or ameliorating brain tissue damage associated with stroke in a subject, the method comprising administering to the subject an effective amount of an agent that inhibits HIF hydroxylase activity, wherein the agent is administered more than 3 hours after the time of stroke onset. Accordingly, methods and agents for treating or ameliorating brain tissue damage are provided wherein the agent is administered more than 3 hours, more than 3½ hours, more than 4 hours, more than 4½ hours, more than 5 hours, more than 5½ hours, more than 6 hours, more than 7 hours, or more than 8 hours after the time of stroke onset.

In certain embodiments, the invention provides methods and agents useful for improving or restoring sensorimotor function in a subject having had a stroke, the method comprising administering to the subject an effective amount of an agent that inhibits hypoxia inducible factor (HIF) hydroxylase activity. In other embodiments, the invention provides methods and agents useful for improving or restoring neuromuscular function in a subject having had a stroke, the method comprising administering to the subject an effective amount of an agent that inhibits hypoxia inducible factor (HIF) hydroxylase activity.

For purposes of this invention, a subject suitable for treatment with the present methods and compounds is a subject who has had a stroke or is suspected of having had a stroke. In various aspects, the subject is a subject who has diabetes.

An agent suitable for use in the present methods is a 2-oxoglutarate mimetic.

In certain embodiments, the agent used in the present methods is a compound selected from the group consisting of the compounds of Formula I, Formula II, Formula III, Formula IV, and Formula V. Formula I includes, but is not limited to, compounds of Formulae Ia, Ib, Ic, and Id. Formula III includes, but is not limited to, the compounds of Formula IIIa. Compounds of Formula IV include, but are not limited to, compounds of Formulae IVA, IVB, IVC, and IVD. Formula V includes, but is not limited to, compounds of Formulae VA, VB, VC, and VD.

In particular embodiments, an agent of the present invention is selected from the group consisting of a quinoline-2-carboxamide, an isoquinoline-3-carboxamide, a cinnoline-3-carboxamide, a beta-carboline-3-carboxamide, a thienopyridine, and an N-substituted arylsulfonylamino hydroxamate.

In particular embodiments, an agent for use in the present methods is selected from the group consisting of [(1-Chloro-4-hydroxy-isoquinoline-3-carbonyl)-amino]-acetic acid (Compound A); [(7-Chloro-3-hydroxy-quinoline-2-carbonyl)-amino]-acetic acid (Compound B); [(3-Hydroxy-6-phenoxy-quinoline-2-carbonyl)-amino]-acetic acid (Compound C); [(1-Chloro-4-hydroxy-5-methyl-isoquinoline-3-carbonyl)-amino]-acetic acid (Compound D); [(4-Hydroxy-7-phenylsulfanyl-isoquinoline-3-carbonyl)-amino]-acetic acid (Compound E); {[4-Hydroxy-7-(4-methoxy-phenoxy)-isoquinoline-3-carbonyl]-amino}-acetic acid (Compound F); {[7-(4-Fluoro-phenoxy)-4-hydroxy-isoquinoline-3-carbonyl]-amino}-acetic acid (Compound G); {[1-Chloro-4-hydroxy-6-(4-methoxy-phenoxy)-isoquinoline-3-carbonyl]-amino}-acetic acid (Compound H); 2-[(4-Hydroxy-7-phenoxy-isoquinoline-3-carbonyl)-amino]-propionic acid (Compound I); [(4-Hydroxy-1-methyl-7-phenoxy-isoquinoline-3-carbonyl)-amino]-acetic acid (Compound J); [(4-Benzyloxy-1-methyl-7-phenoxy-isoquinoline-3-carbonyl)-amino]-acetic acid (Compound K); [(4-Chloro-7-hydroxy-thieno[3,2-c]pyridine-6-carbonyl)-amino]-acetic acid (Compound L); [(7-Ethynyl-4-hydroxy-thieno[2,3-c]pyridine-5-carbonyl)-amino]-acetic acid (Compound M); {[4-Hydroxy-7-(2-methyl-benzooxazol-6-yloxy)-isoquinoline-3-carbonyl]-amino}-acetic acid (Compound N); {[7-(Benzo[1,3]dioxol-5-yloxy)-4-hydroxy-isoquinoline-3-carbonyl]-amino}-acetic acid (Compound O); {[2-(4-Fluoro-phenyl)-4-hydroxy-7-methyl-thieno[2,3-c]pyridine-5-carbonyl]-amino}-acetic acid (Compound P); {[2-(4-Chloro-phenyl)-6-hydroxy-thieno[3,2-b]pyridine-5-carbonyl]-amino}-acetic acid (Compound Q); {[1-Cyano-7-(4-fluoro-phenoxy)-4-hydroxy-isoquinoline-3-carbonyl]-amino}-acetic acid (Compound R); [(7-Chloro-1-cyano-4-hydroxy-isoquinoline-3-carbonyl)-amino]-acetic acid (Compound S); [(7-Chloro-3-hydroxy-4-iodo-quinoline-2-carbonyl)-amino] acetic acid (Compound T); {[1-(4-Chloro-phenylsulfanyl)-4-hydroxy-isoquinoline-3-carbonyl]-amino}-acetic acid (Compound U); [(7-Cyclohexylsulfanyl-4-hydroxy-isoquinoline-3-carbonyl)-amino]-acetic acid (Compound V); [(1-Cyano-4-hydroxy-8-phenoxy-isoquinoline-3-carbonyl)-amino]-acetic acid (Compound W); {[7-(2,3-Dihydro-benzofuran-5-yloxy)-4-hydroxy-isoquinoline-3-carbonyl]-amino}-acetic acid (Compound X); 2-[(4-Hydroxy-7-phenylsulfanyl-isoquinoline-3-carbonyl)-amino]-propionic acid (Compound Y); {[1-(2-Fluoro-phenoxy)-4-hydroxy-isoquinoline-3-carbonyl]-amino}-acetic acid (Compound Z); [(4-Hydroxy-1-methyl-6-phenoxy-isoquinoline-3-carbonyl)-amino]-acetic acid (Compound AA); {[4-Hydroxy-6-(pyridin-2-ylsulfanyl)-isoquinoline-3-carbonyl]-amino}-acetic acid (Compound AB); [(4-Hydroxy-7-phenoxy-isoquinoline-3-carbonyl)-amino]acetic acid (Compound AC); [(2,4-Dibromo-7-hydroxy-thieno[3,2-c]pyridine-6-carbonyl)-amino]-acetic acid (Compound AD); [(4-Bromo-7-hydroxy-thieno[3,2-c]pyridine-6-carbonyl)-amino]-acetic acid (Compound AE); {[4-Hydroxy-1-methyl-7-(2-methyl-benzooxazol-6-yloxy)-isoquinoline-3-carbonyl]-amino}-acetic acid (Compound AF); [(7-Hydroxy-2-phenoxy-thieno[3,2-c]pyridine-6-carbonyl)-amino]-acetic acid (Compound AG); [(4-Cyano-7-hydroxy-thieno[3,2-c]pyridine-6-carbonyl)-amino]-acetic acid (Compound AH); [(4-Furan-3-yl-7-hydroxy-thieno[3,2-c]pyridine-6-carbonyl)-amino]-acetic acid (Compound AI); {[2,3-Bis-(4-fluoro-phenyl)-7-hydroxy-thieno[3,2-c]pyridine-6-carbonyl]-amino}-acetic acid (Compound AJ); [(1-Formyl-4-hydroxy-6-phenoxy-isoquinoline-3-carbonyl)-amino]-acetic acid (Compound AK); {[1-Cyano-6-(2,6-dimethyl-phenoxy)-4-hydroxy-isoquinoline-3-carbonyl]-amino}-acetic acid (Compound AL); [(1-Cyano-4-hydroxy-5-phenoxy-isoquinoline-3-carbonyl)-amino]-acetic acid (Compound AM); {[6-(Benzo[1,3]dioxol-5-yloxy)-1-cyano-4-hydroxy-isoquinoline-3-carbonyl]-amino}-acetic acid (Compound AN); {[1-Cyano-6-(2,3-dihydro-benzofuran-5-yloxy)-4-hydroxy-isoquinoline-3-carbonyl]-amino}-acetic acid (Compound AO); {[1-Cyano-4-hydroxy-8-(3-methoxy-phenoxy)-isoquinoline-3-carbonyl]-amino}-acetic acid (Compound AP); {[1-Cyano-4-hydroxy-6-(2-methyl-benzooxazol-6-yloxy)-isoquinoline-3-carbonyl]-amino}-acetic acid (Compound AQ); [(7-Benzyl-1-cyano-4-hydroxy-isoquinoline-3-carbonyl)-amino]-acetic acid (Compound AR); {[1-Cyano-5-(4-fluoro-phenoxy)-4-hydroxy-isoquinoline-3-carbonyl]-amino}-acetic acid (Compound AS); [(7-Chloro-4-ethyl-3-hydroxy-quinoline-2-carbonyl)-amino]-acetic acid (Compound AT); {[7-Chloro-3-hydroxy-4-(3-trifluorom-ethyl-phenyl)-quinoline-2-carbonyl]-amino}-acetic acid (Compound AU); [(6,7-Dichloro-4-hydroxy-isoquinoline-3-carbonyl)-amino]-acetic acid (Compound AV); [(4-Hydroxy-8-phenyl-isoquinoline-3-carbonyl)-amino]-acetic acid (Compound AW); [(4-Hydroxy-6,7-diphenoxy-isoquinoline-3-carbonyl)-amino]-acetic acid (Compound AX); {[7-(4-Fluoro-phenoxy)-4-hydroxy-1-methyl-isoquinoline-3-carbonyl]-amino}-acetic acid (Compound AY); [(1-Cyano-4-hydroxy-7-phenoxy-isoquinoline-3-carbonyl)-amino]-acetic acid (Compound AZ); {[8-(4-Fluoro-phenoxy)-4-hydroxy-1-methyl-isoquinoline-3-carbonyl]-amino}-acetic acid (Compound BA); {[1-Cyano-8-(4-fluoro-phenoxy)-4-hydroxy-isoquinoline-3-carbonyl]-amino}-acetic acid (Compound BB); [(1-Cyano-4-hydroxy-6-phenoxy-isoquinoline-3-carbonyl)-amino]-acetic acid (Compound BC); and {[1-Cyano-6-(4-fluoro-phenoxy)-4-hydroxy-isoquinoline-3-carbonyl]-amino}-acetic acid (Compound BD).

Pharmaceutical compositions or medicaments effective for use in any of the present methods are provided herein. In various embodiments, the compositions comprise an effective amount of an agent that inhibits HIF hydroxylase activity and a carrier.

In various embodiments of the present invention, the agent is administered orally, systemically, by injection, and intravenously.

It is further contemplated that, in various embodiments, the methods of the present invention are used in combination with administration of one or more other therapeutic agents. Other therapeutic agents (subsequent or coordinate administration) for use in the present methods include a thrombolytic agent, a fibrinolytic agent, an anti-platelet aggregation agent, an anti-coagulant, an antihypertensive agent, an ACE inhibitor, an ARB, a beta-blocker, a cascade channel blocker, a neuroprotectant, a diuretic, a statin, a thrombin inhibitor, or tissue plasminogen activator.

DETAILED DESCRIPTION OF THE INVENTION

Figure 1:
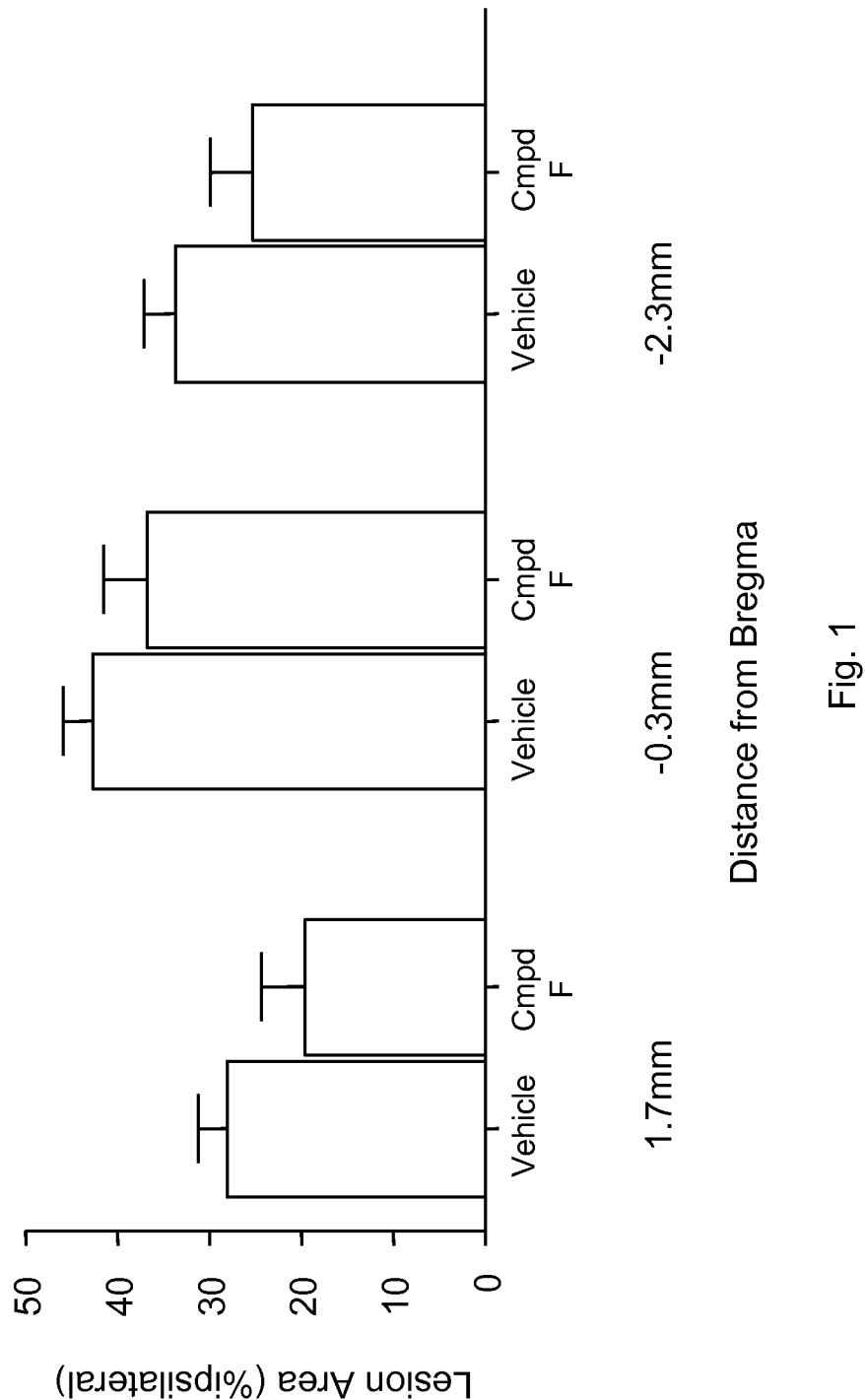
FIG. 1 sets forth data showing methods and compounds of the present invention reduced lesion area in the brain in a transient middle cerebral artery occlusion animal model of stroke.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a HIF-specific 2-oxoglutarate dioxygenase enzyme" may include a plurality of such enzymes; a reference to a "PHI" may be a reference to one or more PHIs, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature.

Methods

The present invention therefore provides alternative or improved methods for treating stroke. In particular, the present invention provides methods for treating a subject diagnosed with or suspected of having had a stroke, said method comprising administering to the subject an effective amount of an agent that stabilizes HIFα. The present invention also provides for the use of an agent that stabilizes HIFα in the manufacture of a medicament for the treatment of stroke. Preferably, the agent is a compound that inhibits HIF prolyl hydroxylase activity.

Methods provided by the present invention are effective for the treatment of stroke, and, in particular, are effective for the treatment of ischemic stroke and hemorrhagic stroke. The consequent elimination of the need to diagnose a stroke as being ischemic or hemorrhagic reduces the delay between the time from stroke onset to treatment, increasing the likelihood of successful treatment. Accordingly, in some embodiments, methods of the present invention are useful for treating a subject diagnosed with or suspected of having had an ischemic stroke. In other embodiments, the methods of the present invention are useful for treating a subject diagnosed with or suspected of having had a hemorrhagic stroke.

The present invention provides alternative or improved methods for treating ischemic disorders or for treating or minimizing ischemic damage. In particular, current treatments for ischemic disorders, for example, diuretics, address only some of the full range of symptoms that can occur. Such treatments are directed towards stabilizing the underlying cause or condition, e.g., stopping hemorrhaging, dissolving a clot, and do not address the tissue damage, infarct size, or associated physiological conditions, such as edema, which can result from ischemic insult. In contrast, the present methods provide for coordinated upregulation of protective factors corresponding to the full range of symptoms associated with ischemic damage. Therefore, the present invention provides methods for treating a subject diagnosed with or suspected of having an ischemic disorder or believed to have been exposed to or be at risk for exposure to an ischemic event, said method comprising administering to the subject an effective amount of an agent that stabilizes HIFα. The present invention also provides for the use of an agent that stabilizes HIFα in the manufacture of a medicament for the treatment of an ischemic disorder. Preferably, the agent is a compound that inhibits HIF prolyl hydroxylase. In certain aspects, the ischemic disorder is cerebrovascular ischemia (e.g., ischemic stroke and transient ischemic attacks), cardiovascular ischemia (e.g., myocardial infarction), peripheral vascular ischemia, and renal ischemia. Thus, in certain aspects, expression of neuroprotective factors and cytoprotective factors occurs locally (i.e., at or adjacent to the ischemic area, infarct, or penumbra).

In certain embodiments, the present invention provides methods for minimizing functional damage (including stroke-related disability, including speech, movement, memory; improving/treating paralysis; improving cognitive function/reducing cognitive impairment, etc.) in a subject, or repairing such damage, including restoring the subject to normal state. The extent of stroke-related disability or functional damage and any improvement or restoration of function can be assessed using any functional assessment known to one of skill in the art. Examples of functional assessment methods include Berg Balance Scale, Modified Rankin Scale, Stroke Impact Scale, and Stroke Specific Quality of Life Measures.

The methods of the present invention may additionally include subsequent or coordinate administration of an additional stroke therapy (e.g., EPO, tPA, etc.) or an additional therapy for ischemic disorders (e.g., digoxin, diuretics, etc.).

The present methods for treatment of stroke can be carried out within any effective therapeutic window. For example, the methods may be carried out 1 minute, 5 minutes, 10 minutes, 15 minutes, 20 minutes, 30 minutes, 1 hour, 2 hours, 3 hours, 4 hours, 5 hours, 6 hours, 7 hours, 8 hours, 9 hours, 10 hours, 11 hours, 12 hours, 15 hours, 20 hours, or 24 hours after the time of stroke onset. In particular, the methods may be carried out more than 1 hour, more than 1½ hours, more than 2 hours, more than 2½ hours, more than 3 hours, more than 3½ hours, more than 4 hours, more than 4½ hours, more than 5 hours, more than 5½ hours, more than 6 hours, more than 7 hours, more than 8 hours, more than 9 hours, more than 10 hours, more than 11 hours, more than 12 hours, more than 15 hours, more than 20 hours, and more than 24 hours after the time of stroke onset. Preferably, the method is carried out as soon as possible after the time of stroke onset.

In particular embodiments, the present invention also provides methods and compounds that are effective in the treatment of stroke even when applied or administered at a time beyond the therapeutic window of current treatments. For example, a current treatment for ischemic stroke is tPA, which is limited to the treatment of ischemic stroke. tPA is effective only if administered within a three-hour window following onset of stroke. The methods of the present invention may applied more than three hours after the time from stroke onset, thus extending the therapeutic window beyond that provided by existing treatments.

Similarly, the methods of the present invention may be carried out 1 minute, 5 minutes, 10 minutes, 15 minutes, 20 minutes, 30 minutes, 1 hour, 2 hours, 3 hours, 4 hours, 5 hours, 6 hours, 7 hours, 8 hours, 9 hours, 10 hours, 11 hours, 12 hours, 15 hours, 20 hours, or 24 hours after an ischemic event or after the subject is believed to have been exposed to or at risk for an ischemic event. In particular, the methods may be carried out more than 1 hour, more than 1½ hours, more than 2 hours, more than 2½ hours, more than 3 hours, more than 3½ hours, more than 4 hours, more than 4½ hours, more than 5 hours, more than 5½ hours, more than 6 hours, more than 7 hours, more than 8 hours, more than 9 hours, more than 10 hours, more than 11 hours, more than 12 hours, more than 15 hours, more than 20 hours, and more than 24 hours after an event triggering an ischemic disorder. Preferably, the method is carried out as soon as possible after the event triggering an ischemic disorder. The methods may be carried out on the subject post-reperfusion, e.g., after the subject has experienced reperfusion following an ischemic injury.

The methods of the present invention may be combined with the administration of one or more other therapeutic agents. In particular, the methods of the present invention may be combined with the administration of one or more therapeutic agents that may be effective in the treatment or prevention of stroke or damage resulting from stroke onset or of ischemic disorders or ischemic damage. Such agents include thrombolytics (e.g., streptokinase, tPA, antistreplase, reteplase, urokinase and tenecteplase); fibrinolytics (Retavase®); antiplatelet agents or platelet antiaggregants (e.g., aspirin, ticlopidine, clopidogrel and dipyridamole); anticoagulants (e.g., warfarin, heparin, ximelagatran); antihypertensives, including diuretics such as bumetamide, chlorothiazide, chlorthalidone, furosemide, hydrochlorothiazide, metolazone, and spironolactone; statins (e.g., HMG-CoA reductase inhibitors); beta blockers (e.g., atenolol, bisoprolol, carvedilol, metoprolol, and propranolol); ACE inhibitors (e.g., benazepril, captopril, enalapril, fosinopril, lisinopril, moexipril, quinapril, ramipril, and trandolapril); angiotensin II receptor antagonists (e.g., candesartan, irbesartan, losartan, potassium, and valsartan); calcium channel blockers (e.g., amlodipine, bepridil, diltiazem, felodipine, isradipine, nicardipine, nimodipine, nisoldipine, and verapamil); angiotensin receptor blockers (ARBs); thrombin inhibitors (e.g., warfarin, Ximelagatran); and other drugs that can lower blood pressure (e.g., clonidine, guanfacine, hydralazine, methyldopa, minoxidil, and prazosin); and neuroprotectants (e.g., NXY-059). Such agents may be administered in simultaneous, separate, or sequential (i.e., before or after) administration with the agents of the present invention.

The present methods comprise administering to a subject an effective amount of a compound that stabilizes HIFα. Such stabilization can be through, e.g., inhibition of HIF hydroxylase activity. A preferred compound of the invention is a compound that inhibits HIF prolyl hydroxylase activity. The inhibition can be direct or indirect, can be competitive or non-competitive, etc. In various embodiments, a compound of the invention is a 2-oxoglutarate mimetic. In one aspect, a 2-oxoglutarate mimetic is a heterocyclic carboxamide. In other aspects, the heterocyclic carboxamide is a quinoline carboxamide, an isoquinoline carboxamide, a pyridine carboxamide, a cinnoline carboxamide, or a beta-carboline carboxamide.

Exemplary compounds of the invention include: [(1-Chloro-4-hydroxy-isoquinoline-3-carbonyl)-amino]-acetic acid (Compound A); [(7-Chloro-3-hydroxy-quinoline-2-carbonyl)-amino]-acetic acid (Compound B); [(3-Hydroxy-6-phenoxy-quinoline-2-carbonyl)-amino]acetic acid (Compound C); [(1-Chloro-4-hydroxy-5-methyl-isoquinoline-3-carbonyl)-amino]-acetic acid (Compound D); [(4-Hydroxy-7-phenylsulfanyl-isoquinoline-3-carbonyl)-amino]-acetic acid (Compound E); {[4-Hydroxy-7-(4-methoxy-phenoxy)-isoquinoline-3-carbonyl]-amino}-acetic acid (Compound F); {[7-(4-Fluoro-phenoxy)-4-hydroxy-isoquinoline-3-carbonyl]-amino}-acetic acid (Compound G); {[1-Chloro-4-hydroxy-6-(4-methoxy-phenoxy)-isoquinoline-3-carbonyl]-amino}-acetic acid (Compound H); 2-[(4-Hydroxy-7-phenoxy-isoquinoline-3-carbonyl)-amino]-propionic acid (Compound I); [(4-Hydroxy-1-methyl-7-phenoxy-isoquinoline-3-carbonyl)-amino]-acetic acid (Compound J); [(4-Benzyloxy-1-methyl-7-phenoxy-isoquinoline-3-carbonyl)-amino]-acetic acid (Compound K); [(4-Chloro-7-hydroxy-thieno[3,2-c]pyridine-6-carbonyl)-amino]-acetic acid (Compound L); [(7-Ethynyl-4-hydroxy-thieno[2,3-c]pyridine-5-carbonyl)-amino]-acetic acid (Compound M); {[4-Hydroxy-7-(2-methyl-benzooxazol-6-yloxy)-isoquinoline-3-carbonyl]-amino}-acetic acid (Compound N); {[7-(Benzo[1,3]dioxol-5-yloxy)-4-hydroxy-isoquinoline-3-carbonyl]-amino}-acetic acid (Compound O); {[2-(4-Fluoro-phenyl)-4-hydroxy-7-methyl-thieno[2,3-c]pyridine-5-carbonyl]-amino}-acetic acid (Compound P); {[2-(4-Chloro-phenyl)-6-hydroxy-thieno[3,2-c]pyridine-5-carbonyl]-amino}-acetic acid (Compound Q); {[1-Cyano-7-(4-fluoro-phenoxy)-4-hydroxy-isoquinoline-3-carbonyl]-amino}-acetic acid (Compound R); [(7-Chloro-1-cyano-4-hydroxy-isoquinoline-3-carbonyl)-amino]-acetic acid (Compound S); [(7-Chloro-3-hydroxy-4-iodo-quinoline-2-carbonyl)-amino]-acetic acid (Compound T); {[1-(4-Chloro-phenylsulfanyl)-4-hydroxy-isoquinoline-3-carbonyl]-amino}-acetic acid (Compound U); [(7-Cyclohexylsulfanyl-4-hydroxy-isoquinoline-3-carbonyl)-amino]-acetic acid (Compound V); [(1-Cyano-4-hydroxy-8-phenoxy-isoquinoline-3-carbonyl)-amino]-acetic acid (Compound W); {[7-(2,3-Dihydro-benzofuran-5-yloxy)-4-hydroxy-isoquinoline-3-carbonyl]-amino}-acetic acid (Compound X); 2-[(4-Hydroxy-7-phenylsulfanyl-isoquinoline-3-carbonyl)-amino]-propionic acid (Compound Y); {[1-(2-Fluoro-phenoxy)-4-hydroxy-isoquinoline-3-carbonyl]-amino}-acetic acid (Compound Z); [(4-Hydroxy-1-methyl-6-phenoxy-isoquinoline-3-carbonyl)-amino]-acetic acid (Compound AA); and {[4-Hydroxy-6-(pyridin-2-ylsulfanyl)-isoquinoline-3-carbonyl]-amino}-acetic acid (Compound AB).

Other exemplary compounds of the invention include: [(4-Hydroxy-7-phenoxy-isoquinoline-3-carbonyl)-amino]-acetic acid (Compound AC); [(2,4-Dibromo-7-hydroxy-thieno[3,2-c]pyridine-6-carbonyl)-amino]-acetic acid (Compound AD); [(4-Bromo-7-hydroxy-thieno[3,2-c]pyridine-6-carbonyl)-amino]-acetic acid (Compound AE); {[4-Hydroxy-1-methyl-7-(2-methyl-benzooxazol-6-yloxy)-isoquinoline-3-carbonyl]-amino}-acetic acid (Compound AF); [(7-Hydroxy-2-phenoxy-thieno[3,2-c]pyridine-6-carbonyl)-amino]-acetic acid (Compound AG); [(4-Cyano-7-hydroxy-thieno[3,2-c]pyridine-6-carbonyl)-amino]-acetic acid (Compound AH); [(4-Furan-3-yl-7-hydroxy-thieno[3,2-c]pyridine-6-carbonyl)-amino]-acetic acid (Compound AI); {[2,3-Bis-(4-fluoro-phenyl)-7-hydroxy-thieno[3,2-c]pyridine-6-carbonyl]-amino}-acetic acid (Compound AJ); [(1-Formyl-4-hydroxy-6-phenoxy-isoquinoline-3-carbonyl)-amino]-acetic acid (Compound AK); {[1-Cyano-6-(2,6-dimethyl-phenoxy)-4-hydroxy-isoquinoline-3-carbonyl]-amino}-acetic acid (Compound AL); [(1-Cyano-4-hydroxy-5-phenoxy-isoquinoline-3-carbonyl)-amino]-acetic acid (Compound AM); {[6-(Benzo[1,3]dioxol-5-yloxy)-1-cyano-4-hydroxy-isoquinoline-3-carbonyl]-amino}-acetic acid (Compound AN); {[1-Cyano-6-(2,3-dihydro-benzofuran-5-yloxy)-4-hydroxy-isoquinoline-3-carbonyl]-amino}-acetic acid (Compound AO); {[1-Cyano-4-hydroxy-8-(3-methoxy-phenoxy)-isoquinoline-3-carbonyl]-amino}-acetic acid (Compound AP); {[1-Cyano-4-hydroxy-6-(2-methyl-benzooxazol-6-yloxy)-isoquinoline-3-carbonyl]-amino}-acetic acid (Compound AQ); [(7-Benzyl-1-cyano-4-hydroxy-isoquinoline-3-carbonyl)-amino]-acetic acid (Compound AR); {[1-Cyano-5-(4-fluoro-phenoxy)-4-hydroxy-isoquinoline-3-carbonyl]-amino}-acetic acid (Compound AS); [(7-Chloro-4-ethyl-3-hydroxy-quinoline-2-carbonyl)-amino]-acetic acid (Compound AT); {[7-Chloro-3-hydroxy-4-(3-trifluoromethyl-phenyl)-quinoline-2-carbonyl]-amino}-acetic acid (Compound AU); [(6,7-Dichloro-4-hydroxy-isoquinoline-3-carbonyl)-amino]acetic acid (Compound AV); [(4-Hydroxy-8-phenyl-isoquinoline-3-carbonyl)-amino]-acetic acid (Compound AW); [(4-Hydroxy-6,7-diphenoxy-isoquinoline-3-carbonyl)-amino]-acetic acid (Compound AX); {[7-(4-Fluoro-phenoxy)-4-hydroxy-1-methyl-isoquinoline-3-carbonyl]-amino}-acetic acid (Compound AY); [(1-Cyano-4-hydroxy-7-phenoxy-isoquinoline-3-carbonyl)-amino]-acetic acid (Compound AZ); {[8-(4-Fluoro-phenoxy)-4-hydroxy-1-methyl-isoquinoline-3-carbonyl]-amino}-acetic acid (Compound BA); {[1-Cyano-8-(4-fluoro-phenoxy)-4-hydroxy-isoquinoline-3-carbonyl]-amino}-acetic acid (Compound BB); [(1-Cyano-4-hydroxy-6-phenoxy-isoquinoline-3-carbonyl)-amino]-acetic acid (Compound BC); and {[1-Cyano-6-(4-fluoro-phenoxy)-4-hydroxy-isoquinoline-3-carbonyl]-amino}-acetic acid (Compound BD).

Additional compounds according to the present invention and methods for identifying additional compounds of the present invention are provided, infra.

Subjects

In preferred embodiments of all the above-described methods, the subject is a human subject.

In certain embodiments, the subject is diagnosed with or suspected of having had a stroke. In other embodiments, the patient is diagnosed with or suspected of having an ischemic disorder, or is believed to have been exposed to or to be at risk for exposure to an ischemic event.

In particular embodiments where the patient is diagnosed with or suspected of having had a stroke, the stroke has not been diagnosed as an ischemic stroke or hemorrhagic stroke. Accordingly, the methods of the present invention are particularly suited for application in the acute phase. Subjects presenting with stroke, particularly stroke that has not been diagnosed as an ischemic stroke or hemorrhagic stroke, are often on life support measures. Such life support measures include the administration of low-flow oxygen (e.g. 1-2 liters/minute), except in instances in which the subject has respiratory distress or respiratory insufficiency; intravenous catheter placement, and 12-lead electrocardiographic tracings; and treatment of hypotension (in accordance with the underlying etiology for the hypotension).

In some embodiments, the subject will be one that has had a stroke before the stroke with which the present invention is concerned. Such subjects will often be on secondary preventative measures to reduce the risk of further strokes or susceptibility to greater damage upon occurrence of an ischemic event. Administration of such agents in simultaneous, separate, or sequential administration with the agent of the present invention is specifically contemplated.

Diabetes is an established risk factor for stroke and is associated with a greater degree of tissue damage following an ischemic insult compared to that observed in non-diabetic subjects. In addition, diabetic subjects who have had a stroke have higher mortality rates, poorer neurological outcomes, and more severe long-term disabilities compared to that observed in non-diabetic stroke subjects. In certain embodiments, the subject having had a stroke will be a subject that has diabetes. Methods for treating stroke in a diabetic subject are specifically contemplated.

Modes of Administration

The agents of the present invention can be delivered directly or in pharmaceutical compositions containing excipients, as is well known in the art. The present methods involve administration of an effective amount of an agent of the present invention to a subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences; and Hardman, Limbird, and Gilman, eds. (2001) The Pharmacological Basis of Therapeutics).

For compositions useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred. For example, for instances in which the compound is not orally bioavailable, intravenous injection may be a preferred route of administration. In certain preferred embodiments, the compounds of the present invention are administered orally. In other preferred embodiments, the compounds of the present invention are administered by intravenous injection.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Compounds

The methods of the present invention comprise administering an agent that stabilizes hypoxia-inducible factor alpha (HIFα). Preferably, the agent is a compound that inhibits HIF prolyl hydroxylase.

Suitable compounds for use in the present methods may be identified and characterized using the assay described in International Publication No. WO 2005/118836, or in Example 10 of International Publication No. WO 2003/049686, both of which are incorporated herein by reference in their entirety. Compounds identifiable by these assays are specifically envisaged for use in the present invention.

Exemplary compounds useful in the present methods are described in, e.g. International Publication No. WO 2004/108121 and International Publication No. WO 2004/108681, incorporated herein by reference in their entireties.

Functionally, the prolyl hydroxylase inhibitors (PHIs) for use in the methods of the present invention are defined by their ability to inhibit an activity of a 2-oxoglutarate dioxygenase enzyme, wherein the enzyme has specific activity toward hypoxia inducible factor. Such compounds are defined herein as prolyl hydroxylase inhibitors (PHIs). Preferably, the PHIs for use in the invention are small molecule compounds.

Several inhibitors of 2-oxoglutarate dioxygenases have been described in general, and inhibitors of various 2-oxoglutarate dioxygenase family members including, e.g., HIF-PH, have been described specifically. (See, Majamaa et al. (1984) Eur J Biochem 138:239-245; Majamaa et al. (1985) Biochem J 229:127-133; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin et al. (2001) Biochem J 353:333-338; Franklin (1991) Biochem Soc Trans 19:812-815; Welford et al. (2003) J Biol Chem 278:10157-10161; and International Publication No. WO 03/049686, all incorporated by reference herein in their entirety.) As used herein, "2-oxoglutarate dioxygenase" encompasses any protein or active fragment thereof that requires $Fe^{2+}$, 2-oxoglutarate, and oxygen for enzymatic activity, e.g., modification of a substrate by hydroxylation. (See, e.g., Majamaa et al. (1985) Biochem J 229:127-133; Myllyharju and Kivirikko (1997) EMBO J. 16:1173-1180; Thornburg et al. (1993) Biochemistry 32:14023-14033; and Jia et al. (1994) Proc Natl Acad Sci USA 91:7227-7231.) Such enzymes include, but are not limited to, procollagen lysyl hydroxylase, procollagen prolyl 3-hydroxylase, procollagen prolyl 4-hydroxylase α(I), αII), and α(III); thymine 7-hydroxylase, aspartyl (asparaginyl) β-hydroxylase; peroxisomal phytanoyl-CoA α-hydroxylase (GenBank Accession AAB81834); ε-N-trimethyllysine hydroxylase (e.g., GenBank Accession AAL01871) and γ-butyrobetaine hydroxylase (e.g., GenBank Accession XP_053891); hypoxia inducible factor prolyl hydroxylase (HIF PH) and factor inhibiting HIF (FIH; e.g., GenBank Accession AAL27308; Mahon et al. (2001) Genes Dev 15:2675-2686; Lando et al. (2002) Science 295:858-861; and Lando et al. (2002) Genes Dev 16:1466-1471. Also, see, Elkins et al. (2002) J Biol Chem C200644200). Additionally, 2-oxoglutarate dioxygenase enzymes include AlkB, an enzyme that catalyses demethylation of substrates, e.g., DNA. (See, e.g., Duncan (2002) Proc Natl Acad Sci USA 99:16660-16665.)

Of particular interest are compounds that inhibit one or more HIF hydroxylases. The term "HIF hydroxylase" refers to any enzyme that modifies the alpha subunit of HIF by hydroxylation of one or more amino acid residues. HIF hydroxylases include Factor Inhibiting HIF (FIH)-1, which modifies at least one asparagine residue found within HIFα (GenBank Accession AAL27308; Mahon et al. (2001) Genes Dev 15:2675-2686; Lando et al. (2002) Science 295:858-861; and Lando et al. (2002) Genes Dev 16:1466-1471. Also, see, Elkins et al. (2002) J Biol Chem C200644200.) HIF hydroxylases also include HIF prolyl hydroxylases, which modify proline residues found within HIFα.

In particular embodiments, the present invention provides for use of 2-oxoglutarate mimetics. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. (1985) Biochem J 229:127-133.) In various embodiments, a compound of the invention is a 2-oxoglutarate mimetic. In one aspect, a 2-oxoglutarate mimetic is a heterocyclic carboxamide. In other aspects, the heterocyclic carboxamide is a quinoline carboxamide, an isoquinoline carboxamide, a pyridine carboxamide, a cinnoline carboxamide, or a beta-carboline carboxamide. Structural mimetics of 2-oxoglut-arate effectively stabilizes HIFα. Such stabilization can be through, e.g., inhibition of prolyl hydroxylase, and, in preferred embodiments, inhibition of HIF prolyl hydroxylase activity. In preferred aspects, a compound of the invention is a compound that inhibits prolyl hydroxylase activity (e.g., a prolyl hydroxylase inhibitor). In more preferred aspects, a compound of the invention is a compound that inhibits HIF prolyl hydroxylase activity. Prolyl hydroxylase inhibitors (PHIs) specifically contemplated for use in the present methods are described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19):812 815; Franklin et al. (2001) Biochem J 353:333-338; and International Publication Nos. WO 03/053977 and WO 03/049686, each incorporated by reference herein in its entirety.

In various embodiments, an agent for use in the present methods is a 2-oxoglutarate mimetic. In certain embodiments, the agent used in the present methods is a compound selected from the group consisting of the compounds of Formula I, Formula II, Formula III, Formula IV, and Formula V. Formula I includes, but is not limited to, compounds of Formulae Ia, Ib, Ic, and Id. Formula III includes, but is not limited to, the compounds of Formula IIIa. Formula IV includes, but is not limited to, compounds of Formulae IVA, IVB, IVC, and IVD. Formula V includes, but is not limited to, compounds of Formulae VA, VB, VC, and VD.

Exemplary PHIs, including [(1-Chloro-4-hydroxy-isoquinoline-3-carbonyl)-amino]-acetic acid (Compound A); [(7-Chloro-3-hydroxy-quinoline-2-carbonyl)-amino]-acetic acid (Compound B); [(3-Hydroxy-6-phenoxy-quinoline-2-carbonyl)-amino]-acetic acid (Compound C); [(1-Chloro-4-hydroxy-5-methyl-isoquinoline-3-carbonyl)-amino]-acetic acid (Compound D); [(4-Hydroxy-7-phenylsulfanyl-isoquinoline-3-carbonyl)-amino]-acetic acid (Compound E); {[4-Hydroxy-7-(4-methoxy-phenoxy)-isoquinoline-3-carbonyl]-amino}-acetic acid (Compound F); {[7-(4-Fluoro-phenoxy)-4-hydroxy-isoquinoline-3-carbonyl]-amino}-acetic acid (Compound G); {[1-Chloro-4-hydroxy-6-(4-methoxy-phenoxy)-isoquinoline-3-carbonyl]-amino}-acetic acid (Compound H); 2-[(4-Hydroxy-7-phenoxy-isoquinoline-3-carbonyl)-amino]-propionic acid (Compound I); [(4-Hydroxy-1-methyl-7-phenoxy-isoquinoline-3-carbonyl)-amino]-acetic acid (Compound J); [(4-Benzyloxy-1-methyl-7-phenoxy-isoquinoline-3-carbonyl)-amino]-acetic acid (Compound K); [(4-Chloro-7-hydroxy-thieno[3,2-c]pyridine-6-carbonyl)-amino]-acetic acid (Compound L); [(7-Ethynyl-4-hydroxy-thieno[2,3-c]pyridine-5-carbonyl)-amino]-acetic acid (Compound M); {[4-Hydroxy-7-(2-methyl-benzooxazol-6-yloxy)-isoquinoline-3-carbonyl]-amino}-acetic acid (Compound N); {[7-(Benzo[1,3]dioxol-5-yloxy)-4-hydroxy-isoquinoline-3-carbonyl]-amino}-acetic acid (Compound O); {[2-(4-Fluoro-phenyl)-4-hydroxy-7-methyl-thieno[2,3-c]pyridine-5-carbonyl]-amino}-acetic acid (Compound P); {[2-(4-Chloro-phenyl)-6-hydroxy-thieno[3,2-b]pyridine-5-carbonyl]-amino}-acetic acid (Compound Q); {[1-Cyano-7-(4-fluoro-phenoxy)-4-hydroxy-isoquinoline-3-carbonyl]-amino}-acetic acid (Compound R); [(7-Chloro-1-cyano-4-hydroxy-isoquinoline-3-carbonyl)-amino]-acetic acid (Compound S); [(7-Chloro-3-hydroxy-4-iodo-quinoline-2-carbonyl)-amino]-acetic acid (Compound T); {[1-(4-Chloro-phenyl-sulfanyl)-4-hydroxy-isoquinoline-3-carbonyl]-amino}-acetic acid (Compound U); [(7-Cyclohexylsulfanyl-4-hydroxy-isoquinoline-3-carbonyl)-amino]-acetic acid (Compound V); [(1-Cyano-4-hydroxy-8-phenoxy-isoquinoline-3-carbonyl)-amino]-acetic acid (Compound W); {[7-(2,3-Dihydro-benzofuran-5-yloxy)-4-hydroxy-isoquinoline-3-carbonyl]-amino}-acetic acid (Compound X); 2-[(4-Hydroxy-7-phenylsulfanyl-isoquinoline-3-carbonyl)-amino]-propionic acid (Compound Y); {[1-(2-Fluoro-phenoxy)-4-hydroxy-isoquinoline-3-carbonyl]-amino}-acetic acid (Compound Z); [(4-Hydroxy-1-methyl-6-phenoxy-isoquinoline-3-carbonyl)-amino]-acetic acid (Compound AA); and {[4-Hydroxy-6-(pyridin-2-ylsulfanyl)-isoquinoline-3-carbonyl]-amino}-acetic acid (Compound AB) are used in the present examples to demonstrate the methods of the invention described herein.

Other exemplary PHIs used in the present examples to demonstrate the methods of the invention described herein include: [(4-Hydroxy-7-phenoxy-isoquinoline-3-carbonyl)-amino]acetic acid (Compound AC); [(2,4-Dibromo-7-hydroxy-thieno[3,2-c]pyridine-6-carbonyl)-amino]-acetic acid (Compound AD); [(4-Bromo-7-hydroxy-thieno[3,2-c]pyridine-6-carbonyl)-amino]-acetic acid (Compound AE); {[4-Hydroxy-1-methyl-7-(2-methyl-benzooxazol-6-yloxy)-isoquinoline-3-carbonyl]-amino}-acetic acid (Compound AF); [(7-Hydroxy-2-phenoxy-thieno[3,2-c]pyridine-6-carbonyl)-amino]-acetic acid (Compound AG); [(4-Cyano-7-hydroxy-thieno[3,2-c]pyridine-6-carbonyl)-amino]-acetic acid (Compound AH); [(4-Furan-3-yl-7-hydroxy-thieno[3,2-c]pyridine-6-carbonyl)-amino]-acetic acid (Compound AI); {[2,3-Bis-(4-fluoro-phenyl)-7-hydroxy-thieno[3,2-c]pyridine-6-carbonyl]-amino}-acetic acid (Compound AJ); [(1-Formyl-4-hydroxy-6-phenoxy-isoquinoline-3-carbonyl)-amino]-acetic acid (Compound AK); {[1-Cyano-6-(2,6-dimethyl-phenoxy)-4-hydroxy-isoquinoline-3-carbonyl]-amino}-acetic acid (Compound AL); [(1-Cyano-4-hydroxy-5-phenoxy-isoquinoline-3-carbonyl)-amino]-acetic acid (Compound AM); {[6-(Benzo[1,3]dioxol-5-yloxy)-1-cyano-4-hydroxy-isoquinoline-3-carbonyl]-amino}-acetic acid (Compound AN); {[1-Cyano-6-(2,3-dihydro-benzofuran-5-yloxy)-4-hydroxy-isoquinoline-3-carbonyl]-amino}-acetic acid (Compound AO); {[1-Cyano-4-hydroxy-8-(3-methoxy-phenoxy)-isoquinoline-3-carbonyl]-amino}-acetic acid (Compound AP); {[1-Cyano-4-hydroxy-6-(2-methyl-benzooxazol-6-yloxy)-isoquinoline-3-carbonyl]-amino}-acetic acid (Compound AQ); [(7-Benzyl-1-cyano-4-hydroxy-isoquinoline-3-carbonyl)-amino]-acetic acid (Compound AR); {[1-Cyano-5-(4-fluoro-phenoxy)-4-hydroxy-isoquinoline-3-carbonyl]-amino}-acetic acid (Compound AS); [(7-Chloro-4-ethyl-3-hydroxy-quinoline-2-carbonyl)-amino]-acetic acid (Compound AT); {[7-Chloro-3-hydroxy-4-(3-trifluoromethyl-phenyl)-quinoline-2-carbonyl]-amino}-acetic acid (Compound AU); [(6,7-Dichloro-4-hydroxy-isoquinoline-3-carbonyl)-amino]-acetic acid (Compound AV); [(4-Hydroxy-8-phenyl-isoquinoline-3-carbonyl)-amino]-acetic acid (Compound AW); [(4-Hydroxy-6,7-diphenoxy-isoquinoline-3-carbonyl)-amino]-acetic acid (Compound AX); {[7-(4-Fluoro-phenoxy)-4-hydroxy-1-methyl-isoquinoline-3-carbonyl]-amino}-acetic acid (Compound AY); [(1-Cyano-4-hydroxy-7-phenoxy-isoquinoline-3-carbonyl)-amino]-acetic acid (Compound AZ); {[8-(4-Fluoro-phenoxy)-4-hydroxy-1-methyl-isoquinoline-3-carbonyl]-amino}-acetic acid (Compound BA); {[1-Cyano-8-(4-fluoro-phenoxy)-4-hydroxy-isoquinoline-3-carbonyl]-amino}-acetic acid (Compound BB); [(1-Cyano-4-hydroxy-6-phenoxy-isoquinoline-3-carbonyl)-amino]-acetic acid (Compound BC); and {[1-Cyano-6-(4-fluoro-phenoxy)-4-hydroxy-isoquinoline-3-carbonyl]-amino}-acetic acid (Compound BD).

The terms "HIF prolyl hydroxylase" and "HIF PH," as used herein, refer to any enzyme that is capable of hydroxylating a proline residue on or associated with an alpha subunit of HIF. In particular embodiments, the proline residue is found within the motif LXXLAP, e.g., as occurs in the human HIF-1α native sequence at $L_{397}$TLLAP and $L_{559}$EMLAP. HIF PH encompasses members of the EGL-9 (EGLN) gene family described by Taylor (2001) Gene 275:125-132; and characterized by Aravind and Koonin (2001) Genome Biol 2:RESEARCH0007; Epstein et al. (2001) Cell 107:43-54; and Bruick and McKnight (2001) Science 294:1337-1340. Examples of HIF PH enzymes include human SM-20 (EGLN1) (GenBank Accession AAG33965; Dupuy et al. (2000) Genomics 69:348-54), EGLN2 isoform 1 (GenBank Accession CAC42510; Taylor, supra), EGLN2 isoform 2 (GenBank Accession NP_060025), and EGLN3 (GenBank Accession CAC42511; Taylor, supra); mouse EGLN1 (GenBank Accession No. CAC42515), EGLN2 (GenBank Accession CAC42511), and EGLN3 (SM-20) (GenBank Accession CAC42517); and rat SM-20 (GenBank Accession AAA19321). Additionally, HIF PH may include *Caenorhabditis elegans* EGL-9 (GenBank Accession AAD56365) and *Drosophila melanogaster* CG1114 gene product (GenBank Accession AAF52050).

The term "prolyl hydroxylase inhibitor" or "PHI," as used herein, refers to any compound that reduces or otherwise modulates the activity of a HIF PH, as defined herein. A PHI may additionally show inhibitory activity toward one or more other 2-oxoglutarate dioxygenase enzymes, e.g. FIH, procollagen P4H, etc. Although PHIs may include, for example, iron chelators, 2-oxoglutarate mimetics, and modified amino acid, e.g., proline, analogs, compounds that function as 2-oxoglutarate mimetics are preferred.

Therefore, in particular embodiments, the present invention provides for use of structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; Majamaa et al. (1985) Biochem J 229:127-133.) PHIs specifically contemplated for use in the present methods are described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19:812-815; Franklin et al. (2001) Biochem J 353:333-338; and International Publication No. WO 2003/049686, all incorporated by reference herein in their entireties.

In one aspect, a compound of the invention is a compound that stabilizes HIFα. Preferably, the compound stabilizes HIFα through inhibition of HIF hydroxylase activity. Exemplary compounds for use in the present methods are disclosed in, e.g., WO 2004/108121 and WO 2004/108681, incorporated herein by reference in their entireties. In various embodiments, the activity is due to a HIF prolyl hydroxylase, such as, for example, EGLN1, EGLN2, or EGLN3, etc. In other embodiments, the activity is due to a HIF asparaginyl hydroxylase, such as, for example, FIH. A preferred compound of the invention is a compound that inhibits HIF prolyl hydroxylase activity. The inhibition can be direct or indirect; can be competitive or non-competitive, etc.

In one aspect, a compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl)hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroxylase, a compound that inhibits the activity of a HIF prolyl hydroxylase may additionally inhibit the activity of a HIF asparaginyl hydroxylase, etc.

In certain embodiments, compounds used in the methods of the invention are selected from a compound of the formula (I)

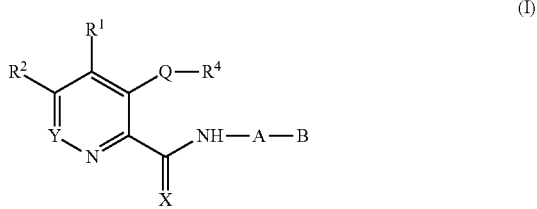

(I)

wherein

A is 1,2-arylidene, 1,3-arylidene, 1,4-arylidene; or ($C_1$-$C_4$)-alkylene, optionally substituted by one or two halogen, cyano, nitro, trifluoromethyl, ($C_1$-$C_6$)-alkyl, ($C_1$-$C_6$)-hydroxyalkyl, ($C_1$-$C_6$)-alkoxy, —O—[$CH_2$]$_x$—$C_fH_{(2f+1-g)}$Hal$_g$, ($C_1$-$C_6$)-fluoroalkoxy, ($C_1$-$C_8$)-fluoroalkenyloxy, ($C_1$-$C_8$)-fluoroalkynyloxy, —OCF$_2$Cl, —O—CF$_2$—CHFCl; ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, phenyl, benzyl, phenoxy, benzyloxy, anilino, N-methylanilino, phenylmercapto, phenylsulfonyl, phenylsulfinyl, sulfamoyl, N—($C_1$-$C_4$)-alkylsulfamoyl, N,N-di-($C_1$-$C_4$)-alkylsulfamoyl; or by a substituted ($C_6$-$C_{12}$)-aryloxy, ($C_7$-$C_{11}$)-aralkyloxy, ($C_6$-$C_{12}$)-aryl, ($C_7$-$C_{11}$)-aralkyl radical, which carries in the aryl moiety one to five identical or different substituents selected from halogen, cyano, nitro, trifluoromethyl, ($C_1$-$C_6$)-alkyl, ($C_1$-$C_6$)-alkoxy, —O—[$CH_2$]$_x$—$C_fH_{(2f+1-g)}$Hal$_g$, —OCF$_2$Cl, —O—CF$_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, sulfamoyl, N—($C_1$-$C_4$)-alkylsulfamoyl, N,N-di-($C_1$-$C_4$)-alkylsulfamoyl; or wherein A is —CR$^5$R$^6$ and R$^5$ and R$^6$ are each independently selected from hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer.

B is —CO$_2$H, —NH$_2$, —NHSO$_2$CF$_3$, tetrazolyl, imidazolyl, 3-hydroxyisoxazolyl, —CONHCOR''', —CONHSOR''', CONHSO$_2$R''', where R''' is aryl, heteroaryl, ($C_3$-$C_7$)-cycloalkyl, or ($C_1$-$C_4$)-alkyl, optionally monosubstituted by ($C_6$-$C_{12}$)-aryl, heteroaryl, OH, SH, ($C_1$-$C_4$)-alkyl, ($C_1$-$C_4$)-alkoxy, ($C_1$-$C_4$)-thioalkyl, ($C_1$-$C_4$)-sulfinyl, ($C_1$-$C_4$)-sulfonyl, CF$_3$, Cl, Br, F, I, NO2, —COOH, ($C_2$-$C_5$)-alkoxycarbonyl, NH$_2$, mono-($C_1$-$C_4$-alkyl)-amino, di-($C_1$-$C_4$-alkyl)-amino, or ($C_1$-$C_4$)-perfluoroalkyl; or wherein B is a CO$_2$-G carboxyl radical, where G is a radical of an alcohol G-OH in which G is selected from ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical, where the alkenyl, cycloalkenyl, alkynyl, and alkenynyl radicals contain one or more multiple bonds; ($C_6$-$C_{16}$)-carbocyclic aryl radical, ($C_7$-$C_{16}$)-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, ($C_1$-$C_{12}$)-alkyl, ($C_3$-$C_8$)-cycloalkyl, ($C_5$-$C_8$)-cycloalkenyl, ($C_6$-$C_{12}$)-aryl, ($C_7$-$C_{16}$)-aralkyl, ($C_2$-$C_{12}$)-alkenyl, ($C_2$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—[$CH_2$]$_x$—$C_fH_{(2f+1-g)}$—F$_g$, —OCF$_2$Cl, —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{12}$)-alkenylcarbonyl, ($C_2$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, acyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di ($C_1$-$C_{12}$)-alkylcarbamoyl, N—($C_3$-$C_8$)-cycloalkyl-carbamoyl, N—($C_6$-$C_{16}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{16}$)-aryloxy-($C_1$-$C_{10}$)-alkyl)-carbamoyl, N—($C_1$-$C_{10}$)-alkyl-N—($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_2$-$C_{12}$)-alkenylamino, ($C_2$-$C_{12}$)-alkynylamino, N—($C_6$-$C_{12}$)-arylamino, N—(C—$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$) arylcarbonylamino, ($C_7$-$C_{16}$)-aralkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)alkylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)alkyl, ($C_6$-$C_{12}$)-arylcarbonylamino-($C_1$-$C_8$)-alkyl, ($C_7$-$C_{12}$)-aralkylcarbonylamino($C_1$-$C_8$)-alkyl, amino-($C_1$-$C_{10}$)-alkyl, N—($C_1$-$C_{10}$) alkylamino-($C_1$-$C_{10}$)-alkyl, N,N-di-($C_1$-$C_{10}$)-alkylamino-($C_1$-$C_{10}$)-alkyl, ($C_3$-$C_8$)cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di($C_1$-$C_{10}$)-alkylsulfamoyl, ($C_3$-$C_8$)-cycloalkylsulfamoyl, N—($C_6$-$C_{12}$)-alkylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, or N—(($C_1$-$C_{10}$)-alkyl-($C_7$-$C_{16}$)-aralkylsulfonamido; wherein radicals which are aryl or contain an aryl moiety, may be substituted on the aryl by one to five identical or different hydroxyl, halogen, cyano, trifluoromethyl, nitro, carboxyl, ($C_1$-$C_{12}$)-alkyl, ($C_3$-$C_8$)-cycloalkyl, ($C_6$-$C_{12}$)-aryl, ($C_7$-$C_{16}$)-aralkyl, ($C_1$-$C_{12}$)-alkoxy, ($C_1$-$C_{12}$)-alkoxy-($C_1$-$C_{12}$)alkyl, ($C_1$-$C_{12}$)-alkoxy-($C_1$ $C_{12}$)alkoxy, ($C_6$-$C_{12}$)-aryloxy, ($C_7$-$C_{16}$)-aralkyloxy, ($C_1$-$C_8$)-hydroxyalkyl, ($C_1$-$C_{12}$)-alkylcarbonyl, ($C_3$-$C_8$)-cycloalkyl-carbonyl, ($C_6$-$C_{12}$)-arylcarbonyl, ($C_7$-$C_{16}$) aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{12}$)-arylcarbamoyl, N—($C_1$-$C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)-alkyl)-carbamoyl, N—($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N—($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—($C_6$-$C_{12}$)-aryloxy-($C_1$-$C_{10}$)-alkyl)-carbamoyloxy, N—($C_1$-$C_{10}$)-alkyl-N—($C_7$-$C_{16}$)-aralkyloxy-($C_1$-$C_{10}$)-alkyl)-carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkylaralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkylcarbonylamino, ($C_3$-$C_8$)-cycloalkylcarbonylamino, ($C_6$-$C_{12}$)-arylcarbonylamino, ($C_7$-$C_{16}$)-alkylcarbonylamino, ($C_1$-$C_{12}$)-alkylcarbonyl-N—($C_1$-$C_{10}$)-alkylamino, ($C_3$-$C_8$)-cycloalkylcarbonyl-N—($C_1$-$C_{10}$)-alkylamino, ($C_6$-$C_{12}$)-arylcarbonyl-N—($C_1$-$C_{10}$)-alkylamino, ($C_7$-$C_{11}$)-aralkylcarbonyl-N—($C_1$-$C_{10}$)-alkylamino, ($C_1$-$C_{12}$)-alkylcarbonylamino-($C_1$-$C_8$)-alkyl, ($C_3$-$C_8$)-cycloalkylcarbonylamino-($C_1$-$C_8$)-alkyl, ($C_6$-$C_{12}$)-arylcarbonylamino-($C_1$-$C_8$)-alkyl, ($C_7$-$C_{16}$)-aralkylcarbonylamino-($C_1$-$C_8$)-alkyl, amino-($C_1$-$C_{10}$)-alkyl, N—($C_1$-$C_{10}$)-alkylamino-($C_1$-$C_{10}$)alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

X is O or S;

Q is O, S, NR', or a bond;

where, if Q is a bond, $R^4$ is halogen, nitrile, or trifluoromethyl;

or where, if Q is O, S, or NR', $R^4$ is hydrogen, ($C_1$-$C_{10}$)-alkyl radical, ($C_2$-$C_{10}$)-alkenyl radical, ($C_2$-$C_{10}$)-alkynyl radical, wherein alkenyl or alkynyl radical contains one or two C—C multiple bonds; unsubstituted fluoroalkyl radical of the formula —[$CH_2$]$_x$—$C_f H_{(2f+1-g)}$—F$_g$, ($C_1$-$C_8$)-alkoxy-($C_1$-$C_6$)-alkyl radical, ($C_1$-$C_6$)-alkoxy-($C_1$-$C_4$)-alkoxy-($C_1$-$C_4$)-alkyl radical, aryl radical, heteroaryl radical, ($C_7$-$C_{11}$)-aralkyl radical, or a radical of the formula Z —[$CH_2$]$_v$—[O]$_w$—[$CH_2$]$_t$-E    (Z)

where

E is a heteroaryl radical, a ($C_3$-$C_8$)-cycloalkyl radical, or a phenyl radical of the formula F

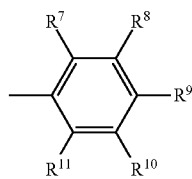

v is 0-6, w is 0 or 1, t is 0-3, and $R^7$, $R^8$, $R^9$, $R^{10}$, and $R^{11}$ are identical or different and are hydrogen, halogen, cyano, nitro, trifluoromethyl, ($C_1$-$C_6$)-alkyl, ($C_3$-$C_8$)-cycloalkyl, ($C_1$-$C_6$)-alkoxy, —O—[$CH_2$]$_x$—

$C_fH_{(2f+1-g)}$—$F_g$, —$OCF_2$—Cl, —O—$CF_2$—CHFCl, ($C_1$-$C_6$)-alkylmercapto, ($C_1$-$C_6$)-hydroxyalkyl, ($C_1$-$C_6$)-alkoxy-($C_1$-$C_6$)-alkoxy, ($C_1$-$C_6$)-alkoxy-($C_1$-$C_6$)-alkyl, ($C_1$-$C_6$)-alkylsulfinyl, ($C_1$-$C_6$)-alkylsulfonyl, ($C_1$-$C_6$)-alkylcarbonyl, ($C_1$-$C_8$)-alkoxycarbonyl, carbamoyl, N—($C_1$-$C_8$)-alkylcarbamoyl, N,N-di-($C_1$-$C_8$)-alkylcarbamoyl, or ($C_7$-$C_{11}$)-aralkylcarbamoyl, optionally substituted by fluorine, chlorine, bromine, trifluoromethyl, ($C_1$-$C_6$)-alkoxy, N—($C_3$-$C_8$)-cycloalkylcarbamoyl, N—($C_3$-$C_8$)-cycloalkyl-($C_1$-$C_4$)-alkylcarbamoyl, ($C_1$-$C_6$)-alkylcarbonyloxy, phenyl, benzyl, phenoxy, benzyloxy, $NR^yR^z$ wherein $R^y$ and $R^z$ are independently selected from hydrogen, ($C_1$-$C_{12}$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_3$-$C_{10}$)-cycloalkyl, ($C_3$-$C_{12}$)-alkenyl, ($C_3$-$C_{12}$)-alkynyl, ($C_6$-$C_{12}$)-aryl, ($C_7$-$C_{11}$)-aralkyl, ($C_1$-$C_{12}$)-alkoxy, ($C_7$-$C_{12}$)aralkoxy, ($C_1$-$C_{12}$)-alkylcarbonyl, ($C_3$-$C_8$)-cycloalkylcarbonyl, ($C_6$-$C_{12}$)arylcarbonyl, ($C_7$-$C_{16}$)-aralkylcarbonyl; or further wherein $R^y$ and $R^z$ together are —$[CH2]_h$, in which a $CH_2$ group can be replaced by O, S, N—($C_1$-$C_4$)-alkylcarbonylimino, or N—($C_1$-$C_4$)-alkoxycarbonylimino; phenylmercapto, phenylsulfonyl, phenylsulfinyl, sulfamoyl, N—($C_1$-$C_8$)-alkylsulfamoyl, or N,N-di-($C_1$-$C_8$)-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH=CH—CH=CH—, where a $CH_2$ group of the chain is optionally replaced by O, S, SO, $SO_2$, or $NR^Y$; and n is 3, 4, or 5; and if E is a heteroaryl radical, said radical can carry 1-3 substituents selected from those defined for $R^7$-$R^{11}$, or if E is a cycloalkyl radical, the radical can carry one substituent selected from those defined for $R^7$-$R^{11}$;

or where, if Q is NR', $R^4$ is alternatively R", where R' and R" are identical or different and are hydrogen, ($C_6$-$C_{12}$)-aryl, ($C_7$-$C_{11}$)-aralkyl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkylcarbonyl, optionally substituted ($C_7$-$C_{16}$)-aralkylcarbonyl, or optionally substituted $C_6$-$C_{12}$)-arylcarbonyl; or R' and R" together are —$[CH_2]_h$, in which a $CH_2$ group can be replaced by O, S, N-acylimino, or N—($C_1$-$C_{10}$)-alkoxycarbonylimino, and h is 3 to 7.

Y is N or $CR^3$;

$R^1$, $R^2$ and $R^3$ are identical or different and are hydrogen, hydroxyl, halogen, cyano, trifluoromethyl, nitro, carboxyl, ($C_1$-$C_{20}$)-alkyl, ($C_3$-$C_8$)-cycloalkyl, ($C_3$-$C_8$)cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl-($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_1$-$C_{20}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy-($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_{16}$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, ($C_2$-$C_{20}$)-alkenyloxy-($C_1$-$C_6$)-alkyl, ($C_2$-$C_{20}$)-alkynyloxy-($C_1$-$C_6$)-alkyl, retinyloxy-($C_1$-$C_6$)-alkyl, —O—$[CH_2]_x$$CfH_{(2f+1-g)}$$F_g$, —$OCF_2$Cl, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—($C_3$-$C_8$)-cycloalkyl-($C_1$-$C_6$)-alkyl)-carbamoyl, N—($C_1$-$C_6$)-alkyl-N—($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{18}$)-alkoxy-($C_1$-$C_{10}$)-alkyl)-carbamoyl, N—($C_6$-$C_{16}$)-aryloxy-($C_1$-$C_{10}$)-alkyl)-carbamoyl, N—($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N—($C_7$-$C_{16}$)-aralkyloxy-($C_1$-$C_{10}$)-alkyl)-carbamoyl; CON$(CH_2)_h$, in which a $CH_2$ group can be replaced by O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; a carbamoyl radical of the formula R

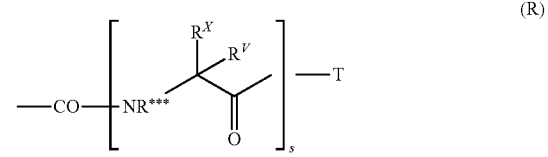

(R)

in which $R^x$ and $R^v$ are each independently selected from hydrogen, ($C_1$-$C_6$)-alkyl, ($C_3$-$C_7$)-cycloalkyl, aryl, or the substituent of an α-carbon of an α-amino acid, to which the L- and D-amino acids belong, s is 1-5, T is OH, or NR*R**, and R*, R and R* are identical or different and are selected from hydrogen, ($C_6$-$C_{12}$)-aryl, ($C_7$-$C_{11}$)-aralkyl, ($C_1$-$C_8$)-alkyl, ($C_3$-$C_8$)-cycloalkyl, (+)-dehydroabietyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, optionally substituted ($C_6$-$C_{12}$)-aroyl; or R* and R** together are —$[CH_2]_h$, in which a $CH_2$ group can be replaced by O, S, SO, $SO_2$, N-acylamino, N—($C_1$-$C_{10}$)-alkoxycarbonylimino, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—(C₁-C₄)-alkoxy-(C₁-C₆)-alkylimino, and h is from 3 to 7; carbamoyloxy, N—(C₁-C₁₂)-alkylcarbamoyloxy, N,N-di-(C₁-C₁₂)-alkylcarbamoyloxy, N—(C₃-C₈)-cycloalkylcarbamoyloxy, N—(C₆-C₁₂)-arylcarbamoyloxy, N—(C₇-C₁₆)-aralkylcarbamoyloxy, N—(C₁-C₁₀)-alkyl-N—(C₆-C₁₂)-arylcarbamoyloxy, N—(C₁-C₁₀)-alkyl-N—(C₇-C₁₆)-aralkylcarbamoyloxy, N—((C₁-C₁₀)-alkyl)-carbamoyloxy, N—((C₆-C₁₂)-aryloxy-(C₁-C₁₀)-alkyl)-carbamoyloxy, N—((C₇-C₁₆)-aralkyloxy-(C₁-C₁₀)-alkyl)-carbamoyloxy, N—(C₁-C₁₀)-alkyl-N—((C₁-C₁₀)-alkoxy-(C₁-C₁₀)-alkyl)-carbamoyloxy, N—(C₁-C₁₀)-alkyl-N—(C₆-C₁₂)-aryloxy-(C₁-C₁₀)-alkyl)-carbamoyloxy, N—(C₁-C₁₀)-alkyl-N—(C₇-C₁₆)-aralkyloxy-(C₁-C₁₀)-alkyl)-carbamoyloxyamino, (C₁-C₁₂)-alkylamino, di-(C₁-C₁₂)-alkylamino, (C₃-C₈)-cycloalkylamino, (C₃-C₁₂)-alkenylamino, (C₃-C₁₂)-alkynylamino, N—(C₆-C₁₂)-arylamino, N—(C₇-C₁₁)-aralkylamino, N-alkyl-aralkylamino, N-alkyl-arylamino, (C₁-C₁₂)-alkoxyamino, (C₁-C₁₂)-alkoxy-N—(C₁-C₁₀)-alkylamino, (C₁-C₁₂)-alkanoylamino, (C₃-C₈)-cycloalkanoylamino, (C₆-C₁₂)-aroylamino, (C₇-C₁₆)-aralkanoylamino, (C₁-C₁₂)-alkanoyl-N—(C₁-C₁₀)-alkylamino, (C₃-C₈)-cycloalkanoyl-N—(C₁-C₁₀)-alkylamino, (C₆-C₁₂)-aroyl-N—(C₁-C₁₀)-alkylamino, (C₇-C₁₁)-aralkanoyl-N—(C₁-C₁₀)-alkylamino, (C₁-C₁₂)-alkanoylamino-(C₁-C₈)-alkyl, (C₃-C₈)-cycloalkanoylamino-(C₁-C₈)-alkyl, (C₆-C₁₂)-aroylamino-(C₁-C₈)-alkyl, (C₇-C₁₆)-aralkanoylamino-(C₁-C₈)-alkyl, amino-(C₁-C₁₀)-alkyl, N—(C₁-C₁₀)-alkylamino-(C₁-C₁₀)-alkyl, N,N-di(C₁-C₁₀)-alkylamino-(C₁-C₁₀)-alkyl, (C₃-C₈)-cycloalkylamino(C₁-C₁₀)-alkyl, (C₁-C₂₀)-alkylmercapto, (C₁-C₂₀)-alkylsulfinyl, (C₁-C₂₀)-alkylsulfonyl, (C₆-C₁₂)-arylmercapto, (C₆-C₁₂)-arylsulfinyl, (C₆-C₁₂)-arylsulfonyl, (C₇-C₁₆)-aralkylmercapto, (C₇-C₁₆)-aralkylsulfinyl, (C₇-C₁₆)-aralkylsulfonyl, (C₁-C₁₂)-alkylmercapto-(C₁-C₆)-alkyl, (C₁-C₁₂)-alkylsulfinyl-(C₁-C₆)-alkyl, (C₁-C₂)-alkylsulfonyl-(C₁-C₆)-alkyl, (C₆-C₁₂)-arylmercapto-(C₁-C₆)-alkyl, (C₆-C₁₂)-arylsulfinyl-(C₁-C₆)-alkyl, (C₆-C₁₂)-arylsulfonyl-(C₁-C₆)-alkyl, (C₇-C₁₆)-aralkylmercapto-(C₁-C₆)-alkyl, (C₇-C₁₆)-aralkylsulfinyl-(C₁-C₆)-alkyl, (C₇-C₁₆)-aralkylsulfonyl-(C₁-C₆)-alkyl, sulfamoyl, N—(C₁-C₁₀)-alkylsulfamoyl, N,N-di-(C₁-C₁₀)-alkylsulfamoyl, (C₃-C₈)-cycloalkylsulfamoyl, N—(C₆-C₁₂)-arylsulfamoyl, N—(C₇-C₁₆)-aralkylsulfamoyl, N—(C₁-C₁₀)-alkyl-N—(C₆-C₁₂)-arylsulfamoyl, N—(C₁-C₁₀)-alkyl-N—(C₇-C₁₆)-aralkylsulfamoyl, (C₁-C₁₀)-alkylsulfonamido, N—((C₁-C₁₀)-alkyl)-(C₁-C₁₀)-alkylsulfonamido, (C₇-C₁₆)-aralkylsulfonamido, and N—((C₁-C₁₀)-alkyl-(C₇-C₁₆)-aralkylsulfonamido; where an aryl radical may be substituted by 1 to 5 substituents selected from hydroxyl, halogen, cyano, trifluoromethyl, nitro, carboxyl, (C₂-C₁₆)-alkyl, (C₃-C₈)-cycloalkyl, (C₃-C₈)-cycloalkyl-(C₁-C₁₂)-alkyl, (C₃-C₈)-cycloalkoxy, (C₃-C₈)-cycloalkyl-(C₁-C₁₂)-alkoxy, (C₃-C₈)-cycloalkyloxy-(C₁-C₁₂)-alkyl, (C₃-C₈)-cycloalkyloxy-(C₁-C₁₂)-alkoxy, (C₃-C₈)-cycloalkyl-(C₁-C₈)-alkyl-(C₁-C₆)-alkoxy, (C₃-C₈)-cycloalkyl(C₁-C₈)-alkoxy-(C₁-C₆)-alkyl, (C₃-C₈)-cycloalkyloxy-(C₁-C₈)-alkoxy-(C₁-C₆)-alkyl, (C₃-C₈)-cycloalkoxy-(C₁-C₈)-alkoxy-(C₁-C₈)-alkoxy, (C₆-C₁₂)-aryl, (C₇-C₁₆)-aralkyl, (C₂-C₁₆)-alkenyl, (C₂-C₁₂)-alkynyl, (C₁-C₁₆)-alkoxy, (C₁-C₁₆)-alkenyloxy, (C₁-C₁₂)-alkoxy-(C₁-C₁₂)-alkyl, (C₁-C₁₂)-alkoxy-(C₁-C₁₂)-alkoxy, (C₁-C₁₂)-alkoxy(C₁-C₈)-alkoxy-(C₁-C₈)-alkyl, (C₆-C₁₂)-aryloxy, (C₇-C₁₆)-aralkyloxy, (C₆-C₁₂)-aryloxy-(C₁-C₆)-alkoxy, (C₇-C₁₆)-aralkoxy-(C₁-C₆)-alkoxy, (C₁-C₈)-hydroxyalkyl, (C₆-C₁₆)-aryloxy-(C₁-C₈)-alkyl, (C₇-C₁₆)-aralkyloxy-(C₁-C₈)-alkyl, (C₆-C₁₂)-aryloxy-(C₁-C₈)-alkoxy-(C₁-C₆)-alkyl, (C₇-C₁₂)-aralkyloxy-(C₁-C₈)-alkoxy-(C₁-C₆)-alkyl, —O—[CH₂]ₓCᵧH₍₂ᶠ₊₁₋g₎Fg, —OCF₂Cl, —OCF₂—CHFCl, (C₁-C₁₂)-alkylcarbonyl, (C₃-C₈)-cycloalkylcarbonyl, (C₆-C₁₂)-arylcarbonyl, (C₇-C₁₆)-aralkylcarbonyl, (C₁-C₁₂)-alkoxycarbonyl, (C₁-C₁₂)-alkoxy-(C₁-C₁₂)-alkoxycarbonyl, (C₆-C₁₂)-aryloxycarbonyl, (C₇-C₁₆)-aralkoxycarbonyl, (C₃-C₈)-cycloalkoxycarbonyl, (C₂-C₁₂)-alkenyloxycarbonyl, (C₂-C₁₂)-alkynyloxycarbonyl, (C₆-C₁₂)-aryloxy-(C₁-C₆)-alkoxycarbonyl, (C₇-C₁₆)-aralkoxy-(C₁-C₆)-alkoxycarbonyl, (C₃-C₈)-cycloalkyl-(C₁-C₆)-alkoxycarbonyl, (C₃-C₈)-cycloalkoxy-(C₁-C₆)-alkoxycarbonyl, (C₁-C₁₂)-alkylcarbonyloxy, (C₃-C₈)-cycloalkylcarbonyloxy, (C₆-C₁₂)-arylcarbonyloxy, (C₇-C₁₆)-aralkylcarbonyloxy, cinnamoyloxy, (C₂-C₁₂)-alkenylcarbonyloxy, (C₂-C₁₂)-alkynylcarbonyloxy, (C₁-C₁₂)-alkoxycarbonyloxy, (C₁-C₁₂)-alkoxy-(C₁-C₁₂)-alkoxycarbonyloxy, (C₆-C₁₂)-aryloxycarbonyloxy, (C₇-C₁₆)-aralkyloxycarbonyloxy, (C₃-C₈)-cycloalkoxycarbonyloxy, (C₂-C₁₂)-alkenyloxycarbonyloxy, (C₂-C₁₂)-alkynyloxycarbonyloxy, carbamoyl, N—(C₁-C₁₂)-alkylcarbamoyl, N,N-di(C₁-C₁₂)-alkylcarbamoyl, N—(C₃-C₈)-cycloalkylcarbamoyl, N,N-dicyclo-(C₃-C₈)-alkylcarbamoyl, N—(C₁-C₁₀)-alkyl-N—(C₃-C₈)-cycloalkylcarbamoyl, N—(C₃-C₈)-cycloalkyl-(C₁-C₆)-alkyl)carbamoyl, N—(C₁-C₆)-alkyl-N—(C₃-C₈)-cycloalkyl-(C₁-C₆)-alkyl)carbamoyl, N-(+)-dehydroabietylcarbamoyl, N—(C₁-C₆)-alkyl-N-(+)-dehydroabietylcarbamoyl, N—(C₆-C₁₂)-arylcarbamoyl, N—(C₇-C₁₆)-aralkylcarbamoyl, N—(C₁-C₁₀)-alkyl-N—(C₆-C₁₆)-arylcarbamoyl, N—(C₁-C₁₀)-alkyl-N—(C₇-C₁₆)-aralkylcarbamoyl, N—(C₁-C₁₆)-alkoxy-(C₁-C₁₀)-alkyl)carbamoyl, N—(C₆-C₁₆)-aryloxy-(C₁-C₁₀)-alkyl)carbamoyl, N—(C₇-C₁₆)-aralkyloxy-(C₁-C₁₀)-alkyl)carbamoyl, N—(C₁-C₁₀)-alkyl-N—(C₁-C₁₀)-alkoxy-(C₁-C₁₀)-alkyl)carbamoyl, N—(C₁-C₁₀)-alkyl-N—((C₆-C₁₂)-aryloxy-(C₁-C₁₀)-alkyl)carbamoyl, N—(C₁-C₁₀)-alkyl-N—(C₇-C₁₆)-aralkyloxy-(C₁-C₁₀)-alkyl)-carbamoyl, CON(CH₂)ₕ, in which a CH₂ group can be replaced by, O, S, N—(C₁-C₈)-alkylimino, N—(C₃-C₈)-cycloalkylimino, N—(C₃-C₈)-cycloalkyl-(C₁-C₄)-alkylimino, N—(C₆-C₁₂)-arylimino, N—(C₇-C₁₆)-aralkylimino, N—(C₁-C₄)-alkoxy-(C₁-C₆)-alkylimino, and h is from 3 to 7; carbamoyloxy, N—(C₁-C₁₂)-alkylcarbamoyloxy, N,N-di-(C₁-C₁₂)-alkylcarbamoyloxy, N—(C₃-C₈)-cycloalkylcarbamoyloxy, N—(C₆-C₁₆)-arylcarbamoyloxy, N—(C₇-C₁₆)-aralkylcarbamoyloxy, N—(C₁-C₁₀)-alkyl-N—(C₆-C₁₂)-arylcarbamoyloxy, N—(C₁-C₁₀)-alkyl-N—(C₇-C₁₆)-aralkylcarbamoyloxy, N—((C₁-C₁₀)-alkyl)carbamoyloxy, N—((C₆-C₁₂)-aryloxy-(C₁-C₁₀)-alkyl)carbamoyloxy, N—((C₇-C₁₆)-aralkyloxy-(C₁-C₁₀)-alkyl)carbamoyloxy, N—(C₁-C₁₀)-alkyl-N—((C₁-C₁₀)-alkoxy-(C₁-C₁₀)-alkyl)carbamoyloxy, N—(C₁-C₁₀)-alkyl-N—(C₆-C₁₂)-aryloxy-(C₁-C₁₀)-alkyl)carbamoyloxy, N—(C₁-C₁₀)-alkyl-N—(C₇-C₁₆)-aralkyloxy-(C₁-C₁₀)-alkyl)carbamoyloxy, amino, (C₁-C₁₂)-alkylamino, di-(C₁-C₁₂)-alkylamino, (C₃-C₈)-cycloalkylamino, (C₃-C₁₂)-alkenylamino, (C₃-C₁₂)-alkynylamino, N—(C₆-C₁₂)-arylamino, N—(C₇-C₁₁)-aralkylamino, N-alkyl-aralkylamino, N-alkyl-arylamino, (C₁-C₁₂)-alkoxyamino, (C₁-C₁₂)-alkoxy-N—(C₁-C₁₀)-alkylamino, (C₁-C₁₂)-alkanoylamino, (C₃-C₈)-cycloalkanoylamino, (C₆-C₁₂)-aroylamino, (C₇-C₁₆)-aralkanoylamino, (C₁-C₁₂)-alkanoyl-N—(C₁-C₁₀)-alkylamino, (C₃-C₈)-cycloalkanoyl-N—(C₁-C₁₀)-alkylamino, (C₆-C₁₂)-aroyl-N—(C₁-C₁₀)-alkylamino, (C₇-C₁₁)-aralkanoyl-N—(C₁-C₁₀)-alkylamino, (C₁-C₁₂)-alkanoylamino-(C₁-C₈)-alkyl, (C₃-C₈)-cycloalkanoylamino-(C₁-C₈)-alkyl, (C₆-C₁₂)-aroylamino-(C₁-C₈)-alkyl, (C₇-C₁₆)-aralkanoylamino-(C₁-C₈)-alkyl, amino-(C₁-C₁₀)-alkyl, N—(C₁-C₁₀)-alkylamino-(C₁-C₁₀)-alkyl, N,N-di-(C₁-C₁₀)-alkylamino-(C₁-C₁₀)-alkyl, (C₃-C₈)- cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, or $(C_7-C_{16})$-aralkylsulfonyl;

or wherein $R^1$ and $R^2$, or $R^2$ and $R^3$ form a chain $[CH_2]_o$, which is saturated or unsaturated by a C=C double bond, in which 1 or 2 $CH_2$ groups are optionally replaced by O, S, SO, $SO_2$, or NR', and R' is hydrogen, $(C_6-C_{12})$-aryl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl, or optionally substituted $(C_6-C_{12})$-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the formulae Ia, Ib and Ic:

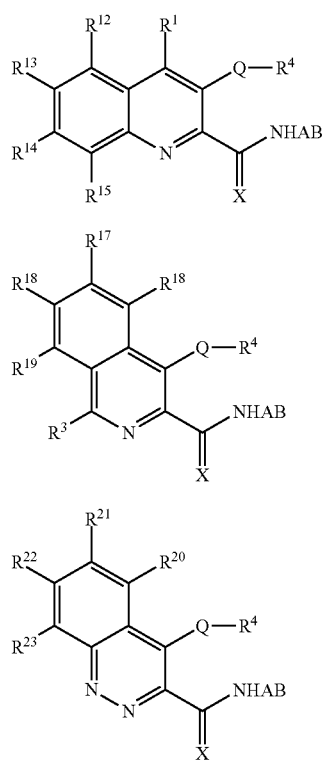

and the substituents $R^{12}$ to $R^{23}$ in each case independently of each other have the meaning of $R^1$, $R^2$ and $R^3$;

or wherein the radicals $R^1$ and $R^2$, together with the pyridine carrying them, form a compound of Formula Id:

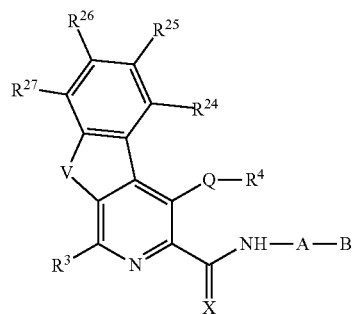

where V is S, O, or $NR^k$, and $R^k$ is selected from hydrogen, $(C_1-C_6)$-alkyl, aryl, or benzyl; where an aryl radical may be optionally substituted by 1 to 5 substituents as defined above; and $R^{24}$, $R^{25}$, $R^{26}$, and $R^{27}$ in each case independently of each other have the meaning of $R^1$, $R^2$ and $R^3$;

f is 1 to 8;

g is 0 or 1 to (2f+1);

x is 0 to 3; and h is 3 to 7;

including the physiologically active salts and prodrugs derived therefrom.

Exemplary compounds according to Formula (I) are described in European Patent Nos. EP0650960 and EP0650961. All compounds listed in EP0650960 and EP0650961, in particular, those listed in the compound claims and the final products of the working examples, are hereby incorporated into the present application by reference herein. Exemplary compounds of Formula (I) include, but are not limited to, [(3-Hydroxy-pyridine-2-carbonyl)-amino]-acetic acid and [(3-methoxy-pyridine-2-carbonyl)-amino]-acetic acid.

Additionally, exemplary compounds according to Formula (I) are described in U.S. Pat. No. 5,658,933. All compounds listed in U.S. Pat. No. 5,658,933, in particular, those listed in the compound claims and the final products of the working examples, are hereby incorporated into the present application by reference herein. Exemplary compounds of Formula (I) include, but are not limited to, 3-methoxypyridine-2-carboxylic acid N-(((hexadecyloxy)-carbonyl)-methyl)-amide hydrochloride, 3-methoxypyridine-2-carboxylic acid N-(((1-octyloxy)-carbonyl)-methyl)-amide, 3-methoxypyridine-2-carboxylic acid N-(((hexyloxy)-carbonyl)-methyl)-amide, 3-methoxypyridine-2-carboxylic acid N-(((butyloxy)-carbonyl)-methyl)-amide, 3-methoxypyridine-2-carboxylic acid N-(((2-nonyloxy)-carbonyl)-methyl)-amide racemate, 3-methoxypyridine-2-carboxylic acid N-(((heptyloxy)-carbonyl)-methyl)-amide, 3-benzyloxypyridine-2-carboxylic acid N-(((octyloxy)-carbonyl)-methyl)-amide, 3-benzyloxypyridine-2-carboxylic acid N-(((butyloxy)-carbonyl)-methyl)-amide, 5-(((3-(1-butyloxy)-propyl)-amino)-carbonyl)-3-methoxypyridine-2-carboxylic acid N-((benzyloxycarbonyl)-methyl)-amide, 5-(((3-(1-butyloxy)-propyl)-amino)-carbonyl)-3-methoxypyridine-2-carboxylic acid N-(((1-butyloxy)-carbonyl)-methyl)-amide, and 5-(((3-lauryloxy)-propyl)amino)-carbonyl)-3-methoxypyridine-2-carboxylic acid N-(((benzyloxy)-carbonyl)-methyl)-amide.

Additional compounds according to Formula (I) are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula (Ia) are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds of Formula (Ia) include, but are not limited to, N-((3-hydroxy-6-isopropoxy-quinoline-2-carbonyl)-amino)-acetic acid, N-((6-(1-butyloxy)-3-hydroxyquinolin-2-yl)-carbonyl)-glycine, [(3-hydroxy-6-trifluoromethoxy-quinoline-2-carbonyl)-amino]-acetic acid, N-((6-chloro-3-hydroxyquinolin-2-yl)-carbonyl)-glycine, N-((7-chloro-3-hydroxyquinolin-2-yl)-carbonyl)-glycine, and [(6-chloro-3-hydroxy-quinoline-2-carbonyl)-amino]-acetic acid.

In certain embodiments, compounds for use in the invention are quinoline-2-carboxamides. In one embodiment, the compound is selected from a compound of the Formula Ia wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and ($C_7$-$C_{11}$)-aralkyl;

$R^1$, $R^{12}$, $R^{13}$, $R^{14}$ and $R^{15}$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_xCfH_{(2f+1-g)}F_g$, —$OCF_2Cl$, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—$[CH_2]_xC_fH_{(2f+1-g)}F_g$, —$OCF_2Cl$, and —$OCF_2$—CHFCl;

x is 0 to 3;

f is 1 to 8; and g is 0 or 1 to (2f+1);

including the physiologically active salts, esters, and prodrugs derived therefrom.

In certain embodiments, the quinoline-2-carboxamide is selected from a compound of the Formula Ia wherein A is —$CHR^5$ and $R^5$ is hydrogen or methyl;

B is —$CO_2H$;

X is O;

Q is O;

R⁴ is hydrogen; and
R¹, R¹², R¹³, R¹⁴ and R¹⁵ are identical or different and are selected from the group consisting hydrogen, chloro, aryl, aryloxy, and substituted aryloxy,
including the physiologically active salts, esters, and prodrugs derived therefrom.

Quinoline-2-carboxamides of Formula Ia additionally include, but are not limited to, [(7-chloro-3-hydroxy-quinoline-2-carbonyl)-amino]-acetic acid], [(3-hydroxy-6-phenoxy-quinoline-2-carbonyl)-amino]-acetic acid, [(7-chloro-3-hydroxy-4-iodo-quinoline-2-carbonyl)-amino]-acetic acid, [(7-chloro-4-ethyl-3-hydroxy-quinoline-2-carbonyl)-amino]-acetic acid, and {[7-Chloro-3-hydroxy-4-(3-trifluoromethyl-phenyl)-quinoline-2-carbonyl]-amino}-acetic acid.

Exemplary compounds according to Formula (Ib) are described in U.S. Pat. No. 6,093,730. All compounds listed in U.S. Pat. No. 6,093,730, in particular, those listed in the compound claims and the final products of the working examples, are hereby incorporated into the present application by reference herein. Exemplary compounds of Formula (Ib) include, but are not limited to, N-((1-chloro-4-hydroxy-7-(2-propyloxy) isoquinolin-3-yl)-carbonyl)-glycine, N-((1-chloro-4-hydroxy-6-(2-propyloxy) isoquinolin-3-yl)-carbonyl)-glycine, N-((1-chloro-4-hydroxy-isoquinoline-3-carbonyl)-amino)-acetic acid (compound A), N-((1-chloro-4-hydroxy-7-methoxyisoquinolin-3-yl)-carbonyl)-glycine, N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N-((7-benzyloxy-1-chloro-4-hydroxy-isoquinoline-3-carbonyl)-amino)-acetic acid, N-((8-chloro-4-hydroxyisoquinolin-3-yl)-carbonyl)-glycine, N-((7-butoxy-4-hydroxy-isoquinoline-3-carbonyl)-amino)-acetic acid.

In certain embodiments, compounds for use in the invention are isoquinoline-3-carboxamides. In one embodiment, the isoquinoline-3-carboxamide is selected from a compound of the Formula Ib wherein
A is —CR⁵R⁶—, and R⁵ and R⁶ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;
B is —$CO_2$H or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;
X is O;
Q is O;
R⁴ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and ($C_7$-$C_{11}$)-aralkyl;
R³, R¹⁶, R¹⁷, R¹⁸ and R¹⁹ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_x$$CfH_{(2f+1-g)}F_g$, —$OCF_2$Cl, —$OCF_2$—CHFCl, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkenyl, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_f$$H_{(2f+1-g)}$$F_g$, —$OCF_2$Cl, and —$OCF_2$—CHFCl;

x is 0 to 3;

f is 1 to 8; and g is 0 or 1 to (2f+1);

including the physiologically active salts, esters, and prodrugs derived therefrom.

In one particular embodiment therein, the isoquinoline-3-carboxamide is selected from a compound of the Formula Ib wherein A is —$CHR^5$ where $R^5$ is selected hydrogen or methyl;

B is —$CO_2H$;

X is O;

Q is O;

$R^4$ is hydrogen, ($C_1$-$C_3$)-alkyl, or substituted ($C_1$-$C_3$)-alkyl;

$R^3$ is hydrogen, chloro, or cyano; and $R^{16}$, $R^{17}$, $R^{18}$ and $R^{19}$ are independently selected from the group consisting of hydrogen, halo, alkyl, substituted alkyl, aryl, heteroaryl, substituted heteroaryl, —$OR^{70}$, —$SR^{70}$, —$SOR^{70}$, and —$SO_2R^{70}$ wherein $R^{70}$ is selected from the group consisting of alkyl, substituted alkyl, cycloalkyl, substituted cycloalkyl, aryl, substituted aryl, heteroaryl, and substituted heteroaryl;

including the physiologically active salts, esters, and prodrugs derived therefrom.

In other embodiments, isoquinoline-3-carboxamides for use in the present invention include those disclosed in International Publication No. WO 2004/108681 and as represented by Formula IV, IVA, IVB, IVC, IVD, VA, VB, VC and VD below. Exemplary isoquinoline-3-carboxamides of Formula 1(b), IV, IVA, IVB, IVC, IVD, VA, VB, VC, or VD and various embodiments provided herein for use in the present invention include, but are not limited to, [(1-chloro-4-hydroxy-isoquinoline-3-carbonyl)-amino]-acetic acid; [(1-chloro-4-hydroxy-5-methyl-isoquinoline-3-carbonyl)-amino]-acetic acid; [(6,7-Dichloro-4-hydroxy-isoquinoline-3-carbonyl)-amino]-acetic acid; [(4-hydroxy-8-phenyl-isoquinoline-3-carbonyl)-amino]-acetic acid; {[1-chloro-4-hydroxy-6-(4-methoxy-phenoxy)-isoquinoline-3-carbonyl]-amino}-acetic acid; [(4-hydroxy-7-phenylsulfanyl-isoquinoline-3-carbonyl)-amino]-acetic acid; [(4-hydroxy-7-phenoxy-isoquinoline-3-carbonyl)-amino]-acetic acid; {[4-hydroxy-7-(4-methoxy-phenoxy)-isoquinoline-3-carbonyl]-amino}-acetic acid; {[7-(4-fluoro-phenoxy)-4-hydroxy-isoquinoline-3-carbonyl]-amino}-acetic acid; (S)-2-[(4-hydroxy-7-phenoxy-isoquinoline-3-carbonyl)-amino]-propionic acid; {[4-hydroxy-7-(2-methyl-benzooxazol-6-yloxy)-isoquinoline-3-carbonyl]-amino}-acetic acid; {[7-(benzo[1,3]dioxol-5-yloxy)-4-hydroxy-isoquinoline-3-carbonyl]-amino}-acetic acid; {[7-(2,3-dihydro-benzofuran-5-yloxy)-4-hydroxy-isoquinoline-3-carbonyl]-amino}-acetic acid; [(7-cyclohexylsulfanyl-4-hydroxy-isoquinoline-3-carbonyl)-amino]-acetic acid; {[4-hydroxy-6-(pyridin-2-ylsulfanyl)-isoquinoline-3-carbonyl]-amino}-acetic acid; 2-[(4-hydroxy-7-phenoxy-isoquinoline-3-carbonyl)-amino]-propionic acid; {[1-(2-fluoro-phenoxy)-4-hydroxy-isoquinoline-3-carbonyl]-amino}-acetic acid; {[1-(4-chloro-phenylsulfanyl)-4-hydroxy-isoquinoline-3-carbonyl]-amino}-acetic acid; [(1-cyano-4-hydroxy-7-phenoxy-isoquinoline-3-carbonyl)-amino]-acetic acid; {[1-cyano-7-(4-fluoro-phenoxy)-4-hydroxy-isoquinoline-3-carbonyl]-amino}-acetic acid; [(7-chloro-1-cyano-4-hydroxy-isoquinoline-3-carbonyl)-amino]-acetic acid; {[1-cyano-8-(4-fluoro-phenoxy)-4-hydroxy-isoquinoline-3-carbonyl]-amino}-acetic acid; [(1-cyano-4-hydroxy-6-phenoxy-isoquinoline-3-carbonyl)-amino]-acetic acid; {[1-cyano-6-(4-fluoro-phenoxy)-4-hydroxy-isoquinoline-3-carbonyl]-amino}-acetic acid; {[1-cyano-6-(2,6-dimethyl-phenoxy)-4-hydroxy-isoquinoline-3-carbonyl]-amino}-acetic acid; [(1-cyano-4-hydroxy-5-phenoxy-isoquinoline-3-carbonyl)-amino]-acetic acid; {[6-(benzo[1,3]dioxol-5-yloxy)-1-cyano-4-hydroxy-isoquinoline-3-carbonyl]-amino}-acetic acid; {[1-cyano-6-(2,3-dihydro-benzofuran-5-yloxy)-4-hydroxy-isoquinoline-3-carbonyl]-amino}-acetic acid; {[1-cyano-4-hydroxy-8-(3-methoxy-phenoxy)-isoquinoline-3-carbonyl]-amino}-acetic acid; {[1-cyano-4-hydroxy-6-(2-methyl-benzooxazol-6-yloxy)-isoquinoline-3-carbonyl]-amino}-acetic acid; [(7-benzyl-1-cyano-4-hydroxy-isoquinoline-3-carbonyl)-amino]-acetic acid; {[1-cyano-5-(4-fluoro-phenoxy)-4-hydroxy-isoquinoline-3-carbonyl]-amino}-acetic acid; [(1-cyano-4-hydroxy-8-phenoxy-isoquinoline-3-carbonyl)-amino]-acetic acid; [(1-formyl-4-hydroxy-6-phenoxy-isoquinoline-3-carbonyl)-amino]-acetic acid; 2-[(4-hydroxy-7-phenylsulfanyl-isoquinoline-3-carbonyl)-amino]-propionic acid; [(4-hydroxy-1-methyl-7-phenoxy-isoquinoline-3-carbonyl)-amino]-acetic acid; [(4-benzyloxy-1-methyl-7-phenoxy-isoquinoline-3-carbonyl)-amino]-acetic acid; {[7-(4-fluoro-phenoxy)-4-hydroxy-1-methyl-isoquinoline-3-carbonyl]-amino}-acetic acid; {[4-hydroxy-1-methyl-7-(2-methyl-benzooxazol-6-yloxy)-isoquinoline-3-carbonyl]-amino}-acetic acid; {[8-(4-fluoro-phenoxy)-4-hydroxy-1-methyl-isoquinoline-3-carbonyl]-amino}-acetic acid; [(4-hydroxy-1-methyl-6-phenoxy-isoquinoline-3-carbonyl)-amino]-acetic acid; and [(4-hydroxy-6,7-diphenoxy-isoquinoline-3-carbonyl)-amino]-acetic acid.

Additionally, compounds related to Formula (I) that can also be used in the methods of the invention include, but are not limited to, 6-cyclohexyl-1-hydroxy-4-methyl-1H-pyridin-2-one, 7-(4-methyl-piperazin-1-ylmethyl)-5-phenylsulfanylmethyl-quinolin-8-ol, 4-nitro-quinolin-8-ol, 5-butoxymethyl-quinolin-8-ol, [(4-Hydroxy-7-phenoxy-isoquinoline-3-carbonyl)-amino]-acetic acid (compound B), and [(4-Hydroxy-7-phenylsulfanyl-isoquinoline-3-carbonyl)-amino]-acetic acid (compound C). Further, the invention provides additional exemplary compounds wherein, e.g., position A and B together may be, e.g., hexanoic acid, cyanomethyl, 2-aminoethyl, benzoic acid, 1H-benzoimidazol-2-ylmethyl, etc.

In another embodiment, compounds for use in the present invention are as disclosed in International Publication No. WO 2006/094292, represented by Formula II

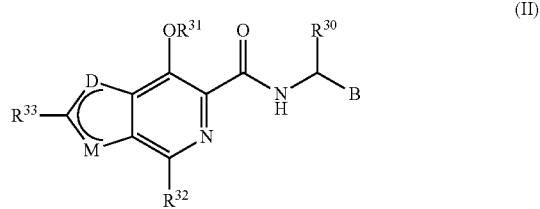

(II)

wherein $R^{30}$ is selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$)

cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkenynyl radical;

$R^{31}$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7-C_{11})$-aralkyl;

one of D or M is —S—, and the other is =C($R^{34}$)—;

$R^{32}$, $R^{33}$, and $R^{34}$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xC_fH_{(2f+1-g)}F_g$, —$OCF_2Cl$, —$OCF_2$—$CHFCl$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—$((C_1-C_{10})$-alkyl)-carbamoyloxy, N—$(C_1-C_{10})$-alkyl-N—$(C_7-C_{16})$-aralkyloxy-$(C_1-C_{10})$-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_2-C_{20})$-alkylsulfinyl, $(C_1-C_{20})$-alkylsulfonyl, $(C_6-C_{12})$-aryl-mercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, $(C_7-C_{16})$-aralkylsulfonamido, and N—$(C_1-C_{10})$-alkyl-$(C_7-C_{16})$-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, and —$OCF_2$—$CHFCl$;

x is 0 to 3;

f is 1 to 8; and g is 0 or 1 to (2f+1);

including the physiologically active salts, esters, and prodrugs derived therefrom.

In certain embodiments, the compound is a compound of Formula II wherein

B is $CO_2H$;

$R^{30}$ and $R^{31}$ are hydrogen;

$R^{32}$ is selected from hydrogen, halo, aryl, substituted aryl, aryloxy, and substituted aryloxy;

$R^{33}$ is selected from hydrogen, halo, cyano, alkyl, alkynyl, and heteroaryl;

one of D or M is —S—, and the other is =C($R^{34}$)—; and $R^{34}$ is hydrogen, aryl, or substituted aryl;

including the physiologically active salts, esters, and prodrugs derived therefrom.

Compounds of Formula II include, but are not limited to, [(2-bromo-4-hydroxy-thieno[2,3-c]pyridine-5-carbonyl)-amino]-acetic acid, [(2-bromo-7-hydroxy-thieno[3,2-c]pyridine-6-carbonyl)-amino]-acetic acid, {[4-hydroxy-2-(4-methoxy-phenyl)-thieno[2,3-c]pyridine-5-carbonyl]-amino}-acetic acid, {[7-hydroxy-2-(4-methoxy-phenyl)-thieno[3,2-c]pyridine-6-carbonyl]-amino}-acetic acid, [(4-hydroxy-2,7-dimethyl-thieno[2,3-c]pyridine-5-carbonyl)-amino]-acetic acid, [(7-hydroxy-2,4-dimethyl-thieno[3,2-c]pyridine-6-carbonyl)-amino]-acetic acid, {[7-hydroxy-4-methyl-2-(4-phenoxy-phenyl)-thieno[3,2-c]pyridine-6-carbonyl]-amino}-acetic acid, {[4-hydroxy-2-(4-phenoxy-phenyl)-7-methyl-thieno[2,3-c]pyridine-5-carbonyl]-amino}-acetic acid, {[4-hydroxy-2-(4-phenoxy-phenyl)-thieno[2,3-c]pyridine-5-carbonyl]-amino}-acetic acid, {[7-hydroxy-2-(4-phenoxy-phenyl)-thieno[3,2-c]pyridine-6-carbonyl]-amino}-acetic acid, [(2,7-dibromo-4-hydroxy-thieno[2,3-c]pyridine-5-carbonyl)-amino]-acetic acid, [(2-bromo-7-chloro-4-hydroxy-thieno[2,3-c]pyridine-5-carbonyl)-amino]-acetic acid, [(7-hydroxy-thieno[3,2-c]pyridine-6-carbonyl)-amino]-acetic acid, [(4-hydroxy-thieno[2,3-c]pyridine-5-carbonyl)-amino]-acetic acid, [(2-bromo-4-chloro-7-hydroxy-thieno[3,2-c]pyridine-6-carbonyl)-amino]-acetic acid, [(2,4-dibromo-7-hydroxy-thieno[3,2-c]pyridine-6-carbonyl)-amino]-acetic acid, [(7-hydroxy-2-phenylsulfanyl-thieno[3,2-c]pyridine-6-carbonyl)-amino]-acetic acid, [(4-hydroxy-2-phenylsulfanyl-thieno[2,3-c]pyridine-5-carbonyl)-amino]-acetic acid, [(4-hydroxy-2,7-diphenyl-thieno[2,3-c]pyridine-5-carbonyl)-amino]-acetic acid, [(7-hydroxy-2,4-diphenyl-thieno[3,2-c]pyridine-6-carbonyl)-amino]-acetic acid, [(7-hydroxy-2-styryl-thieno[3,2-c]pyridine-6-carbonyl)-amino]-acetic acid, [(7-hydroxy-2-phenoxy-thieno[3,2-c]pyridine-6-carbonyl)-amino]-acetic acid, [(7-hydroxy-2-phenethyl-thieno[3,2-c]pyridine-6-carbonyl)-amino]-acetic acid, {[7-hydroxy-2-(3-trifluoromethyl-phenyl)-thieno[3,2-c]pyridine-6-carbonyl]-amino}-acetic acid, {[4-bromo-7-hydroxy-2-(3-trifluoromethyl-phenyl)-thieno[3,2-c]pyridine-6-carbonyl]-amino}-acetic acid, {[4-cyano-7-hydroxy-2-(3-trifluoromethyl-phenyl)-thieno[3,2-c]pyridine-6-carbonyl]-amino}-acetic acid, [(2-cyano-7-hydroxy-thieno[3,2-c]pyridine-6-carbonyl)-amino]-acetic acid, {[7-hydroxy-2-(4-trifluoromethyl-phenyl)-thieno[3,2-c]pyridine-6-carbonyl]-amino}-acetic acid, {[7-hydroxy-2-(2-trifluoromethyl-phenyl)-thieno[3,2-c]pyridine-6-carbonyl]-amino}-acetic acid, {[4-bromo-3-(4-fluoro-phenyl)-7-hydroxy-thieno[3,2-c]pyridine-6-carbonyl]-amino}-acetic acid, {[3-(4-fluoro-phenyl)-7-hydroxy-thieno[3,2-c]pyridine-6-carbonyl]-amino}-acetic acid, {[2-(4-chloro-phenyl)-6-hydroxy-thieno[3,2-b]pyridine-5-carbonyl]-amino}-acetic acid, {[3-(4-fluoro-phenyl)-7-hydroxy-4-methyl-thieno[3,2-c]pyridine-6-carbonyl]-amino}-acetic acid, {[4-cyano-3-(4-fluoro-phenyl)-7-hydroxy-thieno[3,2-c]pyridine-6-carbonyl]-amino}-acetic acid, {[2-(4-fluoro-phenyl)-7-hydroxy-thieno[3,2-c]pyridine-6-carbonyl]-amino}-acetic acid, {[2-(4-fluoro-phenyl)-7-hydroxy-4-methyl-thieno[3,2-c]pyridine-6-carbonyl]-amino}-acetic acid, [(4-cyano-7-hydroxy-thieno[3,2-c]pyridine-6-carbonyl)-amino]-acetic acid, {[2,3-bis-(4-fluoro-phenyl)-7-hydroxy-thieno[3,2-c]pyridine-6-carbonyl]-amino}-acetic acid, {[7-bromo-3-(4-fluoro-phenyl)-4-hydroxy-thieno[2,3-c]pyridine-5-carbonyl]-amino}-acetic acid, {[3-(4-fluoro-phenyl)-4-hydroxy-thieno[2,3-c]pyridine-5-carbonyl]-amino}-acetic acid, {[2-(4-fluoro-phenyl)-4-hydroxy-thieno[2,3-c]pyridine-5-carbonyl]-amino}-acetic acid, {[2-(4-fluoro-phenyl)-4-hydroxy-7-methyl-thieno[2,3-c]pyridine-5-carbonyl]-amino}-acetic acid, [(7-chloro-4-hydroxy-thieno[2,3-c]pyridine-5-carbonyl)-amino]-acetic acid, [(4-chloro-7-hydroxy-thieno[3,2-c]pyridine-6-carbonyl)-amino]-acetic acid, [(7-bromo-4-hydroxy-thieno[2,3-c]pyridine-5-carbonyl)-amino]-acetic acid, [(4-bromo-7-hydroxy-thieno[3,2-c]pyridine-6-carbonyl)-amino]-acetic acid, [(4-hydroxy-7-phenyl-thieno[2,3-c]pyridine-5-carbonyl)-amino]-acetic acid, [(7-hydroxy-4-phenyl-thieno[3,2-c]pyridine-6-carbonyl)-amino]-acetic acid, {[7-(4-fluoro-phenyl)-4-hydroxy-thieno[2,3-c]pyridine-5-carbonyl]-amino}-acetic acid, {[4-(4-fluoro-phenyl)-7-hydroxy-thieno[3,2-c]pyridine-6-carbonyl]-amino}-acetic acid, 2-(7-(furan-2-yl)-4-hydroxythieno[2,3-c]pyridine-5-carboxamido)acetic acid, [(4-furan-2-yl-7-hydroxy-thieno[3,2-c]pyridine-6-carbonyl)-amino]-acetic acid, [(7-furan-3-yl-4-hydroxy-thieno[2,3-c]pyridine-5-carbonyl)-amino]-acetic acid, [(4-furan-3-yl-7-hydroxy-thieno[3,2-c]pyridine-6-carbonyl)-amino]-acetic acid, 2-(4-hydroxy-7-(thiophen-2-yl)thieno[2,3-c]pyridine-5-carboxamido)acetic acid, [(7-hydroxy-4-thiophen-2-yl-thieno[3,2-c]pyridine-6-carbonyl)-amino]-acetic acid, [(4-hydroxy-7-thiophen-3-yl-thieno[2,3-c]pyridine-5-carbonyl)-amino]-acetic acid, [(7-hydroxy-4-thiophen-3-yl-thieno[3,2-c]pyridine-6-carbonyl)-amino]-acetic acid, [(4-hydroxy-7-methyl-thieno[2,3-c]pyridine-5-carbonyl)-amino]-acetic acid, [(7-hydroxy-4-methyl-thieno[3,2-c]pyridine-6-carbonyl)-amino]-acetic acid, [(7-ethynyl-4-hydroxy-thieno[2,3-c]pyridine-5-carbonyl)-amino]-acetic acid, [(4-ethynyl-7-hydroxy-thieno[3,2-c]pyridine-6-carbonyl)-amino]-acetic acid, [(7-cyano-4-hydroxy-thieno[2,3-c]pyridine-5-carbonyl)-amino]-acetic acid, and [(4-cyano-7-hydroxy-thieno[3,2-c]pyridine-6-carbonyl)-amino]-acetic acid.

In other embodiments, compounds used in the methods of the invention are selected from a compound of the formula (III)

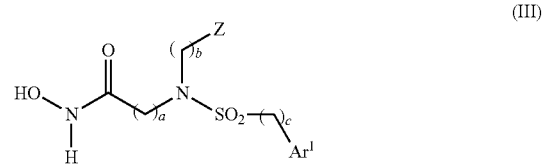

(III)

or pharmaceutically acceptable salts thereof, wherein:
a is an integer from 1 to 4;
b is an integer from 0 to 4;
c is an integer from 0 to 4;
Z is selected from the group consisting of $(C_3-C_{10})$ cycloalkyl, $(C_3-C_{10})$ cycloalkyl independently substituted with one or more $Y^1$, 3-10 membered heterocycloalkyl and 3-10 membered heterocycloalkyl independently substituted with one or more $Y^1$; $(C_5-C_{20})$ aryl, $(C_5-C_{20})$ aryl independently substituted with one or more $Y^1$, 5-20 membered heteroaryl and 5-20 membered heteroaryl independently substituted with one or more $Y^1$;
$Ar^1$ is selected from the group consisting of $(C_5-C_{20})$ aryl, $(C_5-C_{20})$ aryl independently substituted with one or more $Y^2$, 5-20 membered heteroaryl and 5-20 membered heteroaryl independently substituted with one or more $Y^2$;
each $Y^1$ is independently selected from the group consisting of a lipophilic functional group, $(C_5-C_{20})$ aryl, $(C_6-C_{26})$ alkaryl, 5-20 membered heteroaryl and 6-26 membered alk-heteroaryl;
each $Y^2$ is independently selected from the group consisting of —R', —OR', —OR'', —SR', —SR'', —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R'', —NR'—SO$_2$—R', —NR'—C(O)—NR'R', tetrazol-5-yl, —NR'—C(O)—OR', —C(NR'R')=NR', —S(O)—R', —S(O)—R'', and —NR'—C(S)—NR'R; and
each R' is independently selected from the group consisting of —H, $(C_1-C_8)$ alkyl, $(C_2-C_8)$ alkenyl, and $(C_2-C_8)$ alkynyl; and
each R'' is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups,
or wherein c is 0 and $Ar^1$ is an N' substituted urea-aryl, the compound has the structural formula (Ma):

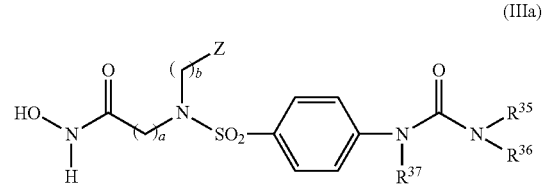

(IIIa)

or pharmaceutically acceptable salts thereof, wherein:
a, b, and Z are as defined above; and
$R^{35}$ and $R^{36}$ are each independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5-20 membered heteroaryl, 5-20 membered substituted heteroaryl, 6-26 membered alk-heteroaryl, and 6-26 membered substituted alk-heteroaryl; and $R^{37}$ is independently selected from the group consisting of hydrogen, ($C_1$-$C_8$) alkyl, ($C_2$-$C_8$) alkenyl, and ($C_2$-$C_8$) alkynyl.

Exemplary compounds of Formula (III) are described in International Publication No. WO 00/50390. All compounds listed in WO 00/50390, in particular, those listed in the compound claims and the final products of the working examples, are hereby incorporated into the present application by reference herein. Exemplary compounds of Formula (III) include 3-{[4-[3,3-d]benzyl-ureido)-benzenesulfonyl]-[2-(4-methoxy-phenyl)-ethyl]-amino}-N-hydroxy-propionamide (compound D), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide.

Methods for identifying compounds of the invention are also provided. In certain aspects, a compound of the invention is one that stabilizes HIFα. The ability of a compound to stabilize or activate HIFα can be measured, for example, by direct measurement of HIFα in a sample, indirect measurement of HIFα, e.g., by measuring a decrease in HIFα associated with the von Hippel Lindau protein (see, e.g., International Publication No. WO 2000/69908), or activation of HIF responsive target genes or reporter constructs (see, e.g., U.S. Pat. No. 5,942,434). Measuring and comparing levels of HIF and/or HIF-responsive target proteins in the absence and presence of the compound will identify compounds that stabilize HIFα and/or activate HIF.

In other aspects, a compound of the invention is one that inhibits HIF hydroxylase activity. Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof (See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184:291-297) describe an exemplary procedure that measures production of succinate from 2-oxoglutarate.

Procedures such as those described above can be used to identify compounds that modulate HIF hydroxylase activity. Target protein may include HIFα or a fragment thereof, e.g., HIF(556-575). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278:30772-30780); additional methods are described in International Publication No. WO 03/049686. Measuring and comparing enzyme activity in the absence and presence of the compound will identify compounds that inhibit hydroxylation of HIFα.

In certain embodiments, the compounds used in the present invention are as disclosed in International Publication No. WO 2004/108681, represented by formula (IV):

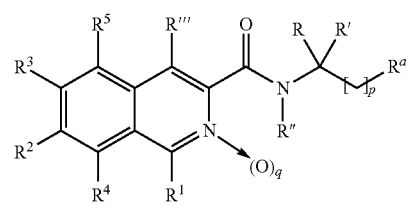

IV wherein:

q is zero or one;

p is zero or one;

$R^a$ is —COOH or —WR$^8$; provided that when $R^a$ is —COOH then p is zero and when $R^a$ is —WR$^8$ then p is one;

W is selected from the group consisting of oxygen, —S(O)$_n$— and —NR$^9$— where n is zero, one or two, R$^9$ is selected from the group consisting of hydrogen, alkyl, substituted alkyl, acyl, aryl, substituted aryl, heteroaryl, substituted heteroaryl, heterocyclic and substituted heterocyclic and R$^8$ is selected from the group consisting of hydrogen, alkyl, substituted alkyl, aryl, substituted aryl, heteroaryl, substituted heteroaryl, heterocyclic and substituted heterocyclic, or when W is —NR$^9$— then R$^8$ and R$^9$, together with the nitrogen atom to which they are bound, can be joined to form a heterocyclic or a substituted heterocyclic group, provided that when W is —S(O)$_n$— and n is one or two, then R$^8$ is not hydrogen;

R$^1$ is selected from the group consisting of hydrogen, alkyl, substituted alkyl, alkoxy, substituted alkoxy, amino, substituted amino, aminoacyl, aryl, substituted aryl, halo, heteroaryl, substituted heteroaryl, heterocyclic, substituted heterocyclic, and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl or, when X is —NR$^7$—, then R$^7$ and R$^8$, together with the nitrogen atom to which they are bound, can be joined to form a heterocyclic or substituted heterocyclic group;

R$^2$ and R$^3$ are independently selected from the group consisting of hydrogen, alkyl, substituted alkyl, aryl, substituted aryl, heteroaryl, substituted heteroaryl, halo, hydroxy, cyano, —S(O)$_n$—N(R$^6$)—R$^6$ where n is 0, 1, or 2, —NR$^6$C(O)NR$^6$R$^6$, —XR$^6$ where X is oxygen, —S(O)$_n$— or —NR$^7$— where n is zero, one or two, each R$^6$ is independently selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic provided that when X is —SO— or —SO$_2$—, then R$_6$ is not hydrogen, and R$^7$ is selected from the group consisting of hydrogen, alkyl, aryl, or R$^2$, R$^3$ together with the carbon atom pendent thereto, form an aryl substituted aryl, heteroaryl, or substituted heteroaryl;

R$^4$ and R$^5$ are independently selected from the group consisting of hydrogen, halo, alkyl, substituted alkyl, alkoxy, substituted alkoxy, aryl, substituted aryl, heteroaryl, substituted heteroaryl and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl or, when X is —NR$^7$—, then R$^7$ and R$^8$, together with the nitrogen atom to which they are bound, can be joined to form a heterocyclic or substituted heterocyclic group;

R is selected from the group consisting of hydrogen, deuterium and methyl;

R' is selected from the group consisting of hydrogen, deuterium, alkyl and substituted alkyl; alternatively, R and R' and the carbon pendent thereto can be joined to form cycloalkyl, substituted cycloalkyl, heterocyclic or substituted heterocyclic group;

R" is selected from the group consisting of hydrogen and alkyl or R" together with R' and the nitrogen pendent thereto can be joined to form a heterocyclic or substituted heterocyclic group;

R''' is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)$_n$—R$^{10}$ wherein R$^{10}$ is selected from the group consisting of alkyl, substituted alkyl, cycloalkyl, substituted cycloalkyl, aryl, substituted aryl, heteroaryl and substituted heteroaryl and n is zero, one or two;

and pharmaceutically acceptable salts, esters and prodrugs thereof;

with the proviso that when R, R' and R" are hydrogen and q is zero, and R$^8$ is either —COOH (p is zero) or —WR$^8$ (p is one) and W is oxygen and R$^8$ is hydrogen then at least one of the following occurs:

1) R$^1$ is fluoro, bromo, iodo, alkyl, substituted alkyl, alkoxy, aminoacyl, substituted alkoxy, aryl, substituted aryl, heteroaryl, substituted heteroaryl, heterocyclic, substituted heterocyclic, and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl; or 2) R$^2$ is substituted alkyl, aryl, substituted aryl, heteroaryl, substituted heteroaryl, fluoro, bromo, iodo, cyano, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl provided that:
a) when R$^2$ is substituted alkyl such a substituent does not include trifluoromethyl;
b) —XR$^6$ is not alkoxy; and
c) when —XR$^6$ is substituted alkoxy such a substituent does not include benzyl or benzyl substituted by a substituent selected from the group consisting of (C$_1$-C$_5$) alkyl and (C$_1$-C$_5$) alkoxy or does not include a fluoroalkoxy substituent of the formula:

—O—[CH$_2$]$_x$—C$_f$H$_{(2f+1-g)}$F$_g$ where x is zero or one; f is an integer of from 1 to 5; and g is an integer of from 1 to (2f+1); or 3) R$^3$ is substituted alkyl, aryl, substituted aryl, heteroaryl, substituted heteroaryl, bromo, iodo, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl provided that:
a) when R$^3$ is substituted alkyl such a substituent does not include trifluoromethyl;
b) —XR$^6$ is not alkoxy; and
c) when —XR$^6$ is substituted alkoxy such a substituent does not include benzyl or benzyl substituted by a substituent selected from the group consisting of (C$_1$-C$_5$) alkyl and (C$_1$-C$_5$) alkoxy or does not include a fluoroalkoxy substituent of the formula:

—O—[CH$_2$]$_x$—C$_f$H$_{(2f+1-g)}$F$_g$ where x is zero or one; f is an integer of from 1 to 5; and g is an integer of from 1 to (2f+1); or 4) R$^4$ is iodo, substituted alkyl, aryl, substituted aryl, heteroaryl, substituted heteroaryl, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl provided that:
a) when R$^4$ is substituted alkyl such a substituent does not include trifluoromethyl;
b) —XR$^6$ is not alkoxy; and
c) when —XR$^6$ is substituted alkoxy such a substituent does not include a fluoroalkoxy substituent of the formula:

—O—[CH$_2$]$_x$—C$_f$H$_{(2f+1-g)}$F$_g$ where x is zero or one; f is an integer of from 1 to 5; and g is an integer of from 1 to (2f+1); or 5) R$^5$ is iodo, substituted alkyl, aryl, substituted aryl, heteroaryl, substituted heteroaryl, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl provided that:
a) when R$^5$ is substituted alkyl such a substituent does not include trifluoromethyl;
b) —XR$^6$ is not alkoxy; and
c) when —XR$^6$ is substituted alkoxy such a substituent does not include a fluoroalkoxy substituent of the formula:

—O—[CH$_2$]$_x$—C$_f$H$_{(2f+1-g)}$F$_g$ where x is zero or one; f is an integer of from 1 to 5; and g is an integer of from 1 to (2f+1);

and with the further following proviso:

that when R$^1$, R$^3$, R$^4$, and R$^5$ are hydrogen, then R$^2$ is not bromo.

In an alternative embodiment, the compounds of formula (IV) are represented by formula (IVA):

IVA wherein R$^1$, R$^2$, R$^3$, R$^4$, R$^5$, R, R', R", R''' and q are as defined above; and pharmaceutically acceptable salts, esters, prodrugs thereof.

In an another alternative embodiment, the compounds of formula (IV) are represented by the formula (IVB):

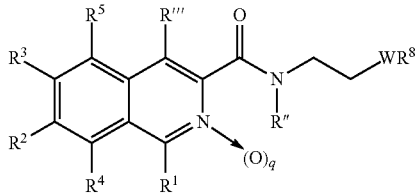

IVB wherein $R^1$, $R^2$, $R^3$, $R^4$, $R^5$, R", R''', $WR^8$ and q are as defined above; and pharmaceutically acceptable salts, esters, prodrugs thereof.

In an another alternative embodiment, the invention is directed to compounds represented by the formula (IVC):

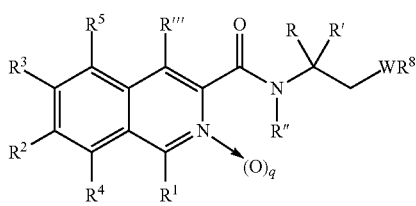

IVC wherein $R^1$, $R^2$, $R^3$, $R^4$, $R^5$, R, R', R", R''', $WR^8$ and q are as defined above; and pharmaceutically acceptable salts, esters, prodrugs thereof.

In yet another alternative embodiment, the invention is directed to compounds represented by the formula (IVD):

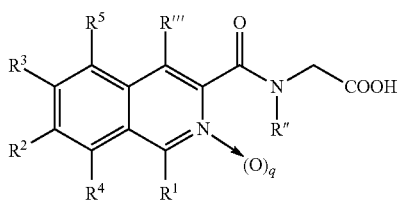

IVD wherein $R^1$, $R^2$, $R^3$, $R^4$, $R^5$, R, R', R", R''' and q are as defined above; and pharmaceutically acceptable salts, esters, prodrugs thereof.

In other embodiments, the invention is directed to compounds represented by the formulae (VA), (VB), (VC), (V), wherein said formulae are defined below.

Formula VA:

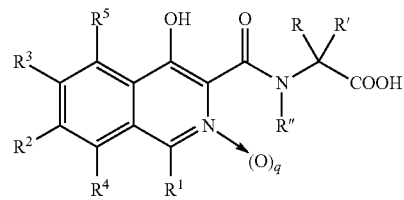

VA wherein:

q is zero or one;

$R^1$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl;

$R^2$ and $R^3$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl;

$R^4$ and $R^5$ are independently selected from the group consisting of hydrogen, halo, alkyl, substituted alkyl, alkoxy, substituted alkoxy, aryl, substituted aryl, heteroaryl, substituted heteroaryl and —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl;

R is selected from the group consisting of hydrogen and methyl;

R' is selected from the group consisting of alkyl and substituted alkyl; or R and R' may be joined to form a cycloalkyl, substituted cycloalkyl, heterocyclic or substituted heterocyclic;

R" is selected from the group consisting of hydrogen and alkyl or R" together with R' and the nitrogen pendent thereto forms a heterocyclic or substituted heterocyclic group;

or pharmaceutically acceptable salts and/or prodrugs thereof.

Formula VB:

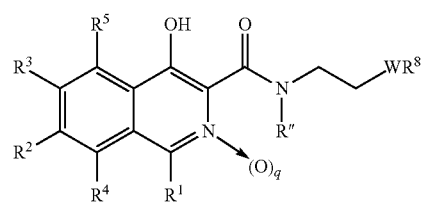

VB wherein:

q is zero or one;

W is selected from the group consisting of oxygen, —S(O)$_n$— and —NR$^9$— where n is zero, one or two, R$^9$ is selected from the group consisting of hydrogen, alkyl, substituted alkyl, acyl, aryl, substituted aryl, heteroaryl, substituted heteroaryl, heterocyclic and substituted heterocyclic, and R$^8$ is selected from the group consisting of hydrogen, alkyl, substituted alkyl, aryl, substituted aryl, heteroaryl, substituted heteroaryl, heterocyclic and substituted heterocyclic;

R" is selected from hydrogen and alkyl;

R$^1$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl;

R$^2$ and R$^3$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl;

R$^4$ and R$^5$ are independently selected from the group consisting of hydrogen, halo, alkyl, substituted alkyl, alkoxy, substituted alkoxy, aryl, substituted aryl, heteroaryl, substituted heteroaryl and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl; or pharmaceutically acceptable salts and/or prodrugs thereof.

Formula VC:

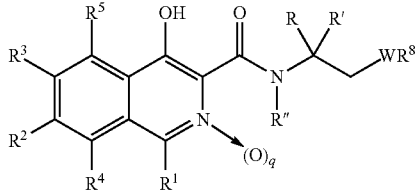

wherein:

q is zero or one;

R$^1$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl, or aryl;

R$^2$ and R$^3$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl, or aryl;

R$^4$ and R$^5$ are independently selected from the group consisting of hydrogen, halo, alkyl, substituted alkyl, alkoxy, substituted alkoxy, aryl, substituted aryl, heteroaryl, substituted heteroaryl and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl, or aryl;

R is selected from the group consisting of hydrogen and methyl;

R' is selected from the group consisting of alkyl and substituted alkyl; or R and R' can be joined to form cycloalkyl, substituted cycloalkyl, heterocyclic or substituted heterocyclic R" is selected from the group consisting of hydrogen and alkyl or R" together with R' and the nitrogen pendent thereto forms a heterocyclic or substituted heterocyclic group;

W is selected from the group consisting of oxygen, —S(O)$_n$— and —NR$^9$— where n is zero, one or two, R$^9$ is selected from the group consisting of hydrogen, alkyl, substituted alkyl, aryl, substituted aryl, heteroaryl, substituted heteroaryl, heterocyclic and substituted heterocyclic, and R$^8$ is selected from the group consisting of hydrogen, alkyl, substituted alkyl, aryl, substituted aryl, heteroaryl, substituted heteroaryl, heterocyclic and substituted heterocyclic; or pharmaceutically acceptable salts and/or prodrugs thereof.

Formula VD:

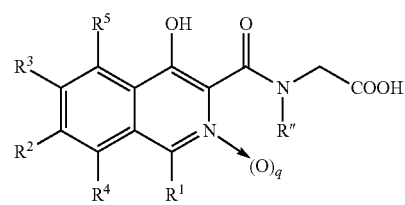

wherein:

q is zero or one;

R" is selected from hydrogen and alkyl;

R$^1$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl;

R$^2$ and R$^3$ are independently selected from the group consisting of hydrogen, alkyl, substituted alkyl, aryl, substituted aryl, heteroaryl, substituted heteroaryl, halo, hydroxy, cyano, —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl;

R$^4$ and R$^5$ are independently selected from the group consisting of hydrogen, halo, alkyl, substituted alkyl, alkoxy, substituted alkoxy, aryl, substituted aryl, heteroaryl, substituted heteroaryl and —XR$^6$ where X is oxygen, —S(O)$_n$— or —NR$^7$— where n is zero, one or two, R$^6$ is selected from the group consisting of alkyl, substituted alkyl, aryl, substituted aryl, heteroaryl, substituted heteroaryl, heterocyclic and substituted heterocyclic, and R$^7$ is hydrogen, alkyl or aryl; or pharmaceutically acceptable salts and/or prodrugs thereof.

In compounds of formulae (IV), (IVA), (IVB), (IVC), and (IVD), preferably R$^1$ is selected from the group consisting of hydrogen, alkyl, substituted alkyl, halo, alkoxy, aryloxy, substituted aryloxy, substituted aryl, alkylthio, aminoacyl, aryl, substituted amino, heteroaryl, heteroaryloxy, —S(O)$_n$-aryl, —S(O)$_n$-substituted aryl, —S(O)$_n$-heteroaryl, and —S(O)$_n$-substituted heteroaryl, where n is zero, one or two.

More preferably, R$^1$ is selected from the group consisting of:
(3-methoxyphenyl)sulfanyl;
(4-chlorophenyl)sulfanyl;
(4-methylphenyl)sulfanyl;
2-fluorophenoxy;
2-methoxyphenoxy;
(2-methoxyphenyl)sulfanyl
3-fluorophenoxy;
3-methoxyphenoxy;
4-(methylcarbonylamino)phenoxy;
4-(methylsulfonamido)phenoxy;
4-fluorophenoxy;
4-methoxyphenoxy;
4-methoxyphenylsulfanyl;
4-methylphenyl;
bromo;
chloro;
dimethylaminomethyl;
ethoxy;
ethylsulfanyl;
hydrogen;
isopropyl;
methoxy;
methoxymethyl;
methyl;
N,N-dimethylaminocarbonyl;
naphth-2-yloxy;
naphthylsulfanyl;
phenoxy;
phenyl;
phenylamino;
phenylsulfinyl;
phenylsulfanyl;
pyridin-2-yloxy;
pyridin-2-yl; and
pyridin-2-ylsulfanyl.

In compounds of formulae (IV), (IVA), (IVB), (IVC), and (IVD), R$^2$ is preferably selected from the group consisting of substituted amino, aryloxy, substituted aryloxy, alkoxy, substituted alkoxy, halo, hydrogen, alkyl, substituted alkyl, aryl, —S(O)$_n$-aryl, —S(O)$_n$-substituted aryl, —S(O)$_n$-cycloalkyl, where n is zero, one or two, aminocarbonylamino, heteroaryloxy, and cycloalkyloxy.

More preferably, R$^2$ is selected from the group consisting of:
(4-methoxy)phenylsulfonylamino;
2,6-dimethylphenoxy;
3,4-difluorophenoxy;
3,5-difluorophenoxy;
3-chloro-4-fluorophenoxy;
3-methoxy-4-fluorophenoxy;
3-methoxy-5-fluorophenoxy;
4-(methylsulfonamido)phenoxy;
4-(phenylsulfonamido)phenoxy;
4-CF$_3$—O-phenoxy;
4-CF$_3$-phenoxy;
4-chlorophenoxy;
4-fluorophenoxy;
4-(4-fluorophenoxy)phenoxy;
4-methoxyphenoxy;
4-nitrophenoxy;
benzyloxy;
bromo;
butoxy;
CF$_3$;
chloro;
cyclohexyloxy;
cyclohexylsulfanyl;
cyclohexylsulfonyl;
fluoro;
hydrogen;
iodo;
isopropoxy;
methyl;
phenoxy;
phenyl;
phenylsulfanyl;
phenylsulfinyl;
phenylsulfonyl;
phenylurea;
pyridin-1-ylsulfanyl;
pyridin-3-yloxy; and
pyridin-4-ylsulfanyl.

In compounds of formulae (IV), (IVA), (IVB), (IVC), and (IVD), R$^3$ is preferably selected from the group consisting of: substituted aryloxy, substituted alkoxy, alkoxy, substituted alkyl, alkyl, amino, cycloalkyloxy, hydrogen, halo, aryl, —S(O)$_n$-aryl, —S(O)$_n$-substituted aryl, —S(O)$_n$-heteroaryl, and —S(O)$_n$-substituted heteroaryl, where n is zero, one or two, aminocarbonylamino, and heteroaryloxy.

More preferably, R$^3$ is selected from the group consisting of:
amino;
(4-methyl)phenylsulfonylaminophenoxy;
3,4-difluorophenoxy;
3,5-difluorophenoxy;
3-fluoro-5-methoxy-phenoxy;
3-chloro-4-fluorophenoxy
4-CF$_3$—O-phenoxy;
4-CF$_3$-phenoxy;
4-chlorophenoxy;
4-fluorophenoxy;
4-(4-fluorophenoxy)phenoxy;
4-methoxyphenoxy;
benzyloxy;
bromo;
butoxy;
CF$_3$;

chloro;
cyclohexyloxy;
hydrogen;
iodo;
isopropoxy;
phenoxy;
phenyl;
phenylsulfanyl;
phenylsulfonyl;
phenylsulfinyl;
phenylurea;
pyridin-1-ylsulfanyl;
pyridin-3-yloxy; and
pyridin-4-ylsulfanyl.

Alternatively, $R^2$ and $R^3$, combined with the carbon atoms pendent thereto, are joined to form an aryl group. Preferably, the aryl group is phenyl.

In compounds of formulae (IV), (IVA), (IVB), (IVC), and (IVD), $R^4$ is preferably selected from the group consisting of: substituted arylthio, halo, hydrogen, substituted alkyl and aryl.

More preferably, $R^4$ is selected from the group consisting of:
4-chlorophenyl sulfanyl;
chloro;
hydrogen;
methoxymethyl; and
phenyl.

In compounds of formulae (IV), (IVA), (IVB), (IVC), and (IVD), $R^5$ is preferably hydrogen or aryl. More preferably $R^5$ is hydrogen or phenyl.

In compounds of formulae (IV), (IVA) and (IVC), R is preferably selected from the group consisting of hydrogen, deuterium, aryl and alkyl. More preferably R is selected from the group consisting of phenyl, hydrogen, deuterium and methyl.

In compounds of formulae (IV), (IVA) and (IVC), R' is selected from the group consisting of preferably hydrogen, deuterium, alkyl, substituted alkyl, and substituted amino. More preferably, R' is selected from the group consisting of:
4-aminobutyl;
4-hydroxybenzyl;
benzyl;
carboxylmethyl;
deuterium;
hydroxymethyl;
imidazol-4-ylmethyl;
isopropyl;
methyl; and
propyl.

Alternatively, R, R' and the carbon atom pendent thereto join to form a cycloalkyl and more preferably cyclopropyl.

In compounds of formulae (IV), (IVA) and (IVC), R" is preferably hydrogen, alkyl or substituted alkyl. More preferably, R" is hydrogen, methyl or carboxylmethyl (—CH$_2$C(O)OH). Alternatively, R', R" and the carbon atom and nitrogen atom respectively pendent thereto join to form a heterocyclic group and more preferably pyrrolidinyl.

In compounds of formulae (IV), (IVA), (IVB), (IVC) and (IVD), preferably R''' is selected from the group consisting of hydrogen, hydroxy, alkoxy, substituted alkoxy, cycloalkoxy, substituted cycloalkoxy, thiol, acyloxy and aryl. Preferably, R''' is selected from the group consisting of:
hydroxy;
benzyloxy;
ethoxy;
thiol;
methoxy;
methylcarbonyloxy; and
phenyl.

In compounds of formulae (IV), (IVB) and (IVC), WR$^8$ is preferably selected from the group consisting of amino, substituted amino, aminoacyl, hydroxy, and alkoxy. More preferably, WR$^8$ is selected from the group consisting of:
amino;
dimethylamino;
hydroxy;
methoxy; and
methylcarbonylamino.

Representative compounds for this application are presented in Tables A-D, wherein said table letter corresponds to formula letter (i.e., representative compounds of formula IVA are in Table A).

TABLE A

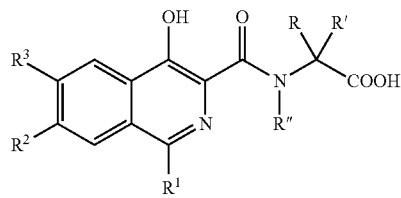

| No. | R$^1$ | R$^2$ | R$^3$ | R | R' | R" |
|---|---|---|---|---|---|---|
| 1 | Cl | H | benzyloxy | H | methyl | H |
| 2 | Cl | H | H | H | hydroxymethyl | H |
| 3 | Cl | H | H | H | hydroxymethyl | H |
| 4 | Cl | H | isopropoxy | H | hydroxymethyl | H |
| 5 | Cl | H | isopropoxy | H | hydroxymethyl | H |
| 6 | Cl | isopropoxy | H | H | hydroxymethyl | H |
| 7 | Cl | isopropoxy | H | H | hydroxymethyl | H |
| 8 | Cl | H | H | methyl | methyl | H |
| 9 | Cl | H | isopropoxy | methyl | methyl | H |
| 10 | Cl | H | H | H | imidazol-4-ylmethyl | H |
| 11 | Cl | H | H | H | imidazol-4-ylmethyl | H |
| 12 | Cl | H | H | H | isopropyl | H |
| 13 | Cl | H | H | H | isopropyl | H |

TABLE A-continued

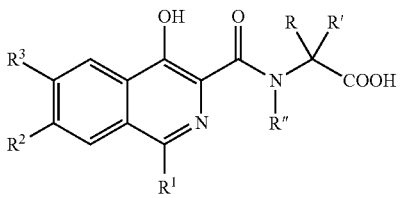

| No. | $R^1$ | $R^2$ | $R^3$ | R | R' | R" |
|---|---|---|---|---|---|---|
| 14 | Cl | H | isopropoxy | H | isopropyl | H |
| 15 | Cl | H | isopropoxy | H | isopropyl | H |
| 16 | Cl | isopropoxy | H | H | isopropyl | H |
| 17 | Cl | isopropoxy | H | H | isopropyl | H |
| 18 | Cl | H | benzyloxy | H | isopropyl | H |
| 19 | Cl | H | H | H | benzyl | H |
| 20 | Cl | H | H | H | benzyl | H |
| 21 | Cl | H | isopropoxy | H | benzyl | H |
| 22 | Cl | H | isopropoxy | H | benzyl | H |
| 23 | Cl | isopropoxy | H | H | benzyl | H |
| 24 | Cl | isopropoxy | H | H | benzyl | H |
| 25 | Cl | H | H | H | 4-hydroxybenzyl | H |
| 26 | Cl | H | H | H | 4-hydroxybenzyl | H |
| 27 | Cl | H | isopropoxy | H | 4-hydroxybenzyl | H |
| 28 | Cl | H | isopropoxy | H | 4-hydroxybenzyl | H |
| 29 | Cl | isopropoxy | H | H | 4-hydroxybenzyl | H |
| 30 | Cl | isopropoxy | H | H | 4-hydroxybenzyl | H |
| 31 | Cl | H | isopropoxy | H | propyl | H |
| 32 | Cl | H | isopropoxy | H | propyl | H |
| 33 | Cl | H | H | H | R' and R" and the carbon and nitrogen atom respectively pendent to which R" is attached join to form a pyrrolidinyl | — |
| 34 | Cl | H | H | H | R' and R" and the carbon and nitrogen atom respectively pendent to which R" is attached join to form a pyrrolidinyl | — |
| 35 | Cl | H | isopropoxy | H | R' and R" and the carbon and nitrogen atom respectively pendent to which R" is attached join to form a pyrrolidinyl | — |
| 36 | Cl | H | isopropoxy | H | R' and R" and the carbon and nitrogen atom respectively pendent to which R" is attached join to form a pyrrolidinyl | — |
| 37 | Cl | H | H | H | 4-aminobutyl | H |
| 38 | Cl | H | H | H | 4-aminobutyl | H |
| 39 | Cl | H | isopropoxy | H | 4-aminobutyl | H |
| 40 | Cl | H | isopropoxy | H | 4-aminobutyl | H |
| 41 | Cl | isopropoxy | H | H | 4-aminobutyl | H |
| 42 | Cl | isopropoxy | H | H | 4-aminobutyl | H |
| 43 | Cl | H | H | H | carboxylmethyl | H |
| 44 | Cl | H | H | H | carboxylmethyl | H |
| 45 | Cl | H | isopropoxy | H | carboxylmethyl | H |
| 46 | Cl | H | isopropoxy | H | carboxylmethyl | H |
| 47 | Cl | isopropoxy | H | H | carboxylmethyl | H |
| 48 | Cl | H | H | — | R, R' together with the carbon to which they are attached join to form cyclopropyl | H |

TABLE A-continued

| No. | R¹ | R² | R³ | R | R' | R" |
|---|---|---|---|---|---|---|
| 49 | Cl | H | isopropoxy | — | R, R" together with the carbon to which they are attached join to form cyclopropyl | H |
| 50 | Cl | H | H | D | D | H |
| 51 | Cl | H | benzyloxy | H | methyl | H |
| 52 | Cl | benzyloxy | H | H | methyl | H |
| 53 | Cl | benzyloxy | H | H | methyl | H |
| 54 | Cl | H | H | H | methyl | H |
| 55 | Cl | H | H | H | methyl | H |
| 56 | Cl | H | isopropoxy | H | methyl | H |
| 57 | Cl | H | isopropoxy | H | methyl | H |
| 58 | Cl | isopropoxy | H | H | methyl | H |
| 59 | Cl | isopropoxy | H | H | methyl | H |
| 60 | H | 4-chlorophenoxy | H | H | methyl | H |
| 61 | H | H | 4-chlorophenoxy | H | methyl | H |
| 62 | H | 3,4-difluorophenoxy | H | H | methyl | H |
| 63 | H | phenylsulfanyl | H | H | methyl | H |
| 64 | H | phenylsulfanyl | H | H | methyl | H |
| 65 | H | phenoxy | H | H | methyl | H |
| 66 | H | 4-methoxyphenoxy | H | H | methyl | H |
| 67 | H | phenylsulfonyl | H | H | methyl | H |
| 68 | methoxymethyl | phenoxy | H | H | methyl | H |
| 69 | methoxymethyl | phenoxy | H | H | methyl | H |
| 70 | H | phenoxy | H | H | methyl | H |
| 71 | 4-chlorophenyl sulfanyl | H | H | H | methyl | H |
| 72 | 4-chlorophenyl sulfanyl | H | H | H | methyl | H |
| 73 | H | 3-methoxy-4-fluorophenoxy | H | H | methyl | H |
| 74 | H | cyclohexyloxy | H | H | methyl | H |
| 75 | methyl | 4-fluorophenoxy | H | H | methyl | H |
| 76 | H | 4-fluorophenoxy | H | H | methyl | H |
| 77 | methyl | phenoxy | H | H | methyl | H |
| 78 | methyl | phenylsulfanyl | H | H | methyl | H |
| 79 | H | 4-trifluoromethyl-phenoxy | H | H | methyl | H |

TABLE B

| No. | R² | R³ | WR⁸ |
|---|---|---|---|
| 1 | H | H | methoxy |
| 2 | isopropoxy | H | amino |
| 3 | H | isopropoxy | methoxy |
| 4 | H | H | amino |
| 5 | H | H | hydroxy |
| 6 | H | isopropoxy | hydroxy |
| 7 | H | H | dimethylamino |
| 8 | H | H | methylcarbonylamino |
| 9 | H | isopropoxy | amino |
| 10 | H | isopropoxy | dimethylamino |
| 11 | isopropoxy | H | methoxy |
| 12 | isopropoxy | H | dimethylamino |
| 13 | isopropoxy | H | hydroxy |

TABLE C

[Structure: isoquinoline with OH at 4-position, R³ at 6, R² at 7, Cl at 1, and C(=O)NH-CH(CH₂OH)₂ at 3-position]

| No. | R² | R³ |
|---|---|---|
| 1 | isopropoxy | H |
| 2 | H | isopropoxy |
| 3 | H | H |

TABLE D

[Structure: isoquinoline with R⁵ at 5, R''' at 4, R³ at 6, R² at 7, R⁴ at 8, R¹ at 1, and C(=O)-N(R'')-CH₂-COOH at 3-position]

| No. | R¹ | R² | R³ | R⁴ | R⁵ | R'' | R''' |
|---|---|---|---|---|---|---|---|
| 1 | Br | 2,6-di(CH₃)phenyloxy | H | H | H | H | OH |
| 2 | Br | butoxy | H | H | H | H | OH |
| 3 | Br | phenoxy | H | H | H | H | OH |
| 4 | Cl | Br | H | H | H | H | OH |
| 5 | Br | Cl | H | H | H | H | OH |
| 6 | Cl | I | H | H | H | H | OH |
| 7 | Cl | H | I | H | H | H | OH |
| 8 | Cl | phenoxy | H | H | H | H | OH |
| 9 | Cl | phenylsulfanyl | H | H | H | H | OH |
| 10 | Br | —CF₃ | H | H | H | H | OH |
| 11 | Br | H | phenoxy | H | H | H | OH |
| 12 | Cl | H | H | phenyl | H | H | OH |
| 13 | Cl | 2,6-di(CH₃)phenyloxy | H | H | H | H | OH |
| 14 | Br | H | CF₃ | H | H | H | OH |
| 15 | Br | Br | H | H | H | H | OH |
| 16 | Br | phenylsulfanyl | H | H | H | H | OH |
| 17 | Cl | H | phenylsulfanyl | H | H | H | OH |
| 18 | 4-methoxyphenyl-sulfanyl | H | H | H | H | H | OH |
| 19 | Br | H | H | phenyl | H | H | OH |
| 20 | Cl | phenyl | H | H | H | H | OH |
| 21 | Br | H | H | H | H | H | OH |
| 22 | Br | methyl | H | H | H | H | OH |
| 23 | Br | H | butoxy | H | H | H | OH |
| 24 | Br | H | Cl | H | H | H | OH |
| 25 | Cl | H | phenoxy | H | H | H | OH |
| 26 | Br | H | phenoxy | H | H | H | OH |
| 27 | H | I | H | H | H | H | OH |
| 28 | Br | phenyl | H | H | H | H | OH |
| 29 | Br | H | phenyl | H | H | H | OH |
| 30 | ethylsulfanyl | H | H | H | H | H | OH |
| 31 | phenoxy | H | H | H | H | H | OH |
| 32 | H | H | phenyl | H | H | H | OH |
| 33 | Br | H | H | H | phenyl | H | OH |
| 34 | Br | F | H | H | H | H | OH |
| 35 | H | 2,6-di(CH₃)phenyloxy | H | H | H | H | OH |
| 36 | Cl | H | phenyl | H | H | H | OH |
| 37 | H | phenoxy | H | H | H | H | OH |
| 38 | H | phenylsulfanyl | H | H | H | H | OH |
| 39 | H | phenyl | H | H | H | H | OH |
| 40 | H | H | phenoxy | H | H | H | OH |

TABLE D-continued

| No. | R¹ | R² | R³ | R⁴ | R⁵ | R" | R''' |
|---|---|---|---|---|---|---|---|
| 41 | H | H | phenylsulfanyl | H | H | H | OH |
| 42 | H | H | H | phenyl | H | H | OH |
| 43 | Cl | H | H | H | phenyl | H | OH |
| 44 | H | H | H | H | phenyl | H | OH |
| 45 | Cl | F | H | H | H | H | OH |
| 46 | H | F | H | H | H | H | OH |
| 47 | H | H | Br | H | H | H | OH |
| 48 | H | R²/R³ = phenyl | — | H | H | H | OH |
| 49 | Br | H | benzyloxy | H | H | methyl | OH |
| 50 | Cl | H | H | H | H | methyl | OH |
| 51 | Cl | H | isopropoxy | H | H | methyl | OH |
| 52 | Cl | isopropoxy | H | H | H | methyl | OH |
| 53 | Cl | H | H | H | H | CH₂COOH | OH |
| 54 | Cl | H | isopropoxy | H | H | CH₂COOH | OH |
| 55 | naphth-2-yloxy | H | H | H | H | H | OH |
| 56 | pyridin-3-yloxy | H | H | H | H | H | OH |
| 57 | 4-methoxy phenoxy | H | H | H | H | H | OH |
| 58 | 3-methoxy phenoxy | H | H | H | H | H | OH |
| 59 | 3-fluorophenoxy | H | H | H | H | H | OH |
| 60 | 4-fluorophenoxy | H | H | H | H | H | OH |
| 61 | 2-fluorophenoxy | H | H | H | H | H | OH |
| 62 | 2-methoxy phenoxy | H | H | H | H | H | OH |
| 63 | 4-(methyl carbonyl amino) phenoxy | H | H | H | H | H | OH |
| 64 | 4-(methyl sulfonamido) phenoxy | H | H | H | H | H | OH |
| 65 | phenyl amino | H | H | H | H | H | OH |
| 66 | H | H | pyridin-3-yloxy | H | H | H | OH |
| 67 | H | pyridin-3-yloxy | H | H | H | H | OH |
| 68 | Cl | H | H | H | H | H | methoxy |
| 69 | Cl | H | H | H | H | H | ethoxy |
| 70 | methoxy | H | H | H | H | H | OH |
| 71 | ethoxy | H | H | H | H | H | OH |
| 72 | phenyl | H | H | H | H | H | methyl-carbonyloxy |
| 73 | phenyl | H | H | H | H | H | OH |
| 74 | ethoxy | H | H | H | H | H | phenyl |
| 75 | Cl | H | H | H | H | H | phenyl |
| 76 | H | H | H | H | H | H | phenyl |
| 77 | methyl | H | H | H | H | H | OH |
| 78 | methoxy methyl | H | H | H | H | H | OH |
| 79 | N,N-dimethyl amino carbonyl | H | H | H | H | H | OH |
| 80 | methyl | H | phenoxy | H | H | H | OH |
| 81 | methyl | phenoxy | H | H | H | H | OH |
| 82 | methyl | phenoxy | H | H | H | H | benzyloxy |
| 83 | methyl | phenoxy | H | H | H | H | ethoxy |
| 84 | N,N-dimethyl amino carbonyl | phenoxy | H | H | H | H | OH |
| 85 | methoxy methyl | phenoxy | H | H | H | H | OH |

TABLE D-continued

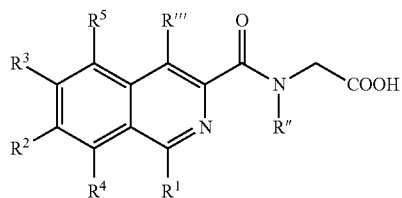

| No. | R¹ | R² | R³ | R⁴ | R⁵ | R" | R''' |
|---|---|---|---|---|---|---|---|
| 86 | 4-methyl phenyl | H | H | H | H | H | OH |
| 87 | methyl phenoxy | 4-fluoro | H | H | H | H | OH |
| 88 | Cl phenoxy | 4-methoxy | H | H | H | H | OH |
| 89 | H phenoxy | 4-methoxy | H | H | H | H | OH |
| 90 | Cl | H | 4-methoxy-phenoxy | H | H | H | OH |
| 91 | H | H | 4-methoxy-phenoxy | H | H | H | OH |
| 92 | Cl | 4-CF₃-phenoxy | H | H | H | H | OH |
| 93 | H | 4-CF₃-phenoxy | H | H | H | H | OH |
| 94 | Cl | H | 4-CF₃-phenoxy | H | H | H | OH |
| 95 | H | H | 4-CF₃-phenoxy | H | H | H | OH |
| 96 | Cl | 4-fluorophenoxy | H | H | H | H | OH |
| 97 | H | 4-fluorophenoxy | H | H | H | H | OH |
| 98 | Cl | H | 4-fluoro-phenoxy | H | H | H | OH |
| 99 | H | H | 4-fluoro-phenoxy | H | H | H | OH |
| 100 | H | pyridin-4-yl sulfanyl | H | H | H | H | OH |
| 101 | H | H | pyridin-4-yl sulfanyl | H | H | H | OH |
| 102 | H | phenylsulfinyl | H | H | H | H | OH |
| 103 | H | phenylsulfonyl | H | H | H | H | OH |
| 104 | H | H | phenyl sulfinyl | H | H | H | OH |
| 105 | H | H | phenyl sulfonyl | H | H | H | OH |
| 106 | H | H | amino | H | H | H | OH |
| 107 | H | (4-methoxy) phenylsulfonyl amino | H | H | H | H | OH |
| 108 | H | phenylurea | H | H | H | H | OH |
| 109 | H | H | phenylurea | H | H | H | OH |
| 110 | phenyl sulfanyl | H | H | H | H | H | OH |
| 111 | (4-chloro phenyl) sulfanyl | H | H | H | H | H | OH |
| 112 | (4-methyl phenyl) sulfanyl | H | H | H | H | H | OH |
| 113 | pyridin-2-ylsulfanyl | H | H | H | H | H | OH |
| 114 | (3-methoxy phenyl) sulfanyl | H | H | H | H | H | OH |
| 115 | 2-methoxy phenyl sulfanyl | H | H | H | H | H | OH |
| 116 | naphthyl sulfanyl | H | H | H | H | H | OH |
| 117 | phenyl sulfinyl | H | H | H | H | H | OH |
| 118 | phenyl sulfonyl | H | H | H | H | H | OH |
| 119 | H | pyridin-2-yl sulfanyl | H | H | H | H | OH |
| 120 | H | H | pyridin-2-yl sulfanyl | H | H | H | OH |
| 121 | Cl | phenoxy | phenoxy | H | H | H | OH |
| 122 | H | phenoxy | phenoxy | H | H | H | OH |
| 123 | H | H | (4-methyl)phenyl SO₂—NH-phenoxy | H | H | H | OH |
| 124 | H | 4-nitrophenoxy | H | H | H | H | OH |
| 125 | H | phenoxy | H | H | H | H | thiol |
| 126 | H | CF₃ | H | H | H | H | thiol |
| 127 | H | 4-(phenylsulfonamido) phenoxy | H | H | H | H | OH |

TABLE D-continued

| No. | R¹ | R² | R³ | R⁴ | R⁵ | R″ | R‴ |
|---|---|---|---|---|---|---|---|
| 128 | H | 4-(methylsulfonamido)phenoxy | H | H | H | H | OH |
| 129 | H | 4-chlorophenoxy | H | H | H | H | OH |
| 130 | H | H | 4-chloro-phenoxy | H | H | H | OH |
| 131 | H | H | 3-fluoro-5-methoxy-phenoxy | H | H | H | OH |
| 132 | H | 3-methoxy-5-fluorophenoxy | H | H | H | H | OH |
| 133 | H | 3,4-difluorophenoxy | H | H | H | H | OH |
| 134 | H | H | 3,4-difluoro-phenoxy | H | H | H | OH |
| 135 | H | 4-CF₃—O—phenoxy | H | H | H | H | OH |
| 136 | H | H | 4-CF₃—O-phenoxy | H | H | H | OH |
| 137 | H | 3,5-difluorophenoxy | H | H | H | H | OH |
| 138 | H | H | 3,5-difluorophenoxy | H | H | H | OH |
| 139 | H | 4-(4-fluorophenoxy)phenoxy | H | H | H | H | OH |
| 140 | H | H | 4-(4-fluorophenoxy)phenoxy | H | H | H | OH |
| 141 | H | 3-chloro-4-fluorophenoxy | H | H | H | H | OH |
| 142 | H | H | 3-chloro-4-fluorophenoxy | H | H | H | OH |
| 143 | methyl | 4-chlorophenoxy | H | H | H | H | OH |
| 144 | methyl | H | 4-chlorophenoxy | H | H | H | OH |
| 145 | methyl | 3,5-difluorophenoxy | H | H | H | H | OH |
| 146 | methyl | 4-methoxyphenoxy | H | H | H | H | OH |
| 147 | methyl | H | 4-methoxyphenoxy | H | H | H | OH |
| 148 | H | H | cyclohexyloxy | H | H | H | OH |
| 149 | H | cyclohexyloxy | H | H | H | H | OH |
| 150 | methyl | cyclohexyloxy | H | H | H | H | OH |
| 151 | H | cyclohexyl sulfanyl | H | H | H | H | OH |
| 152 | H | cyclohexyl sulfonyl | H | H | H | H | OH |
| 153 | isopropyl | H | H | H | H | H | OH |
| 154 | pyridin-2-yl | H | H | H | H | H | OH |
| 155 | ethyl | phenoxy | H | H | H | H | OH |
| 156 | dimethyl amino methyl | phenylsulfanyl | H | H | H | H | OH |
| 157 | methyl | phenylsulfanyl | H | H | H | H | OH |
| 158 | methyl | 4-trifluoromethyl phenoxy | H | H | H | H | OH |

Compounds included within the scope of this invention include, for example, those set forth below:

{[4-Hydroxy-1-(naphthalen-2-yloxy)-isoquinoline-3-carbonyl]-amino}-acetic acid;

{[4-Hydroxy-1-(pyridin-3-yloxy)-isoquinoline-3-carbonyl]-amino}-acetic acid;

{[4-Hydroxy-1-(4-methoxy-phenoxy)-isoquinoline-3-carbonyl]-amino}-acetic acid;

{[4-Hydroxy-1-(3-methoxy-phenoxy)-isoquinoline-3-carbonyl]-amino}-acetic acid;

{[1-(3-Fluoro-phenoxy)-4-hydroxy-isoquinoline-3-carbonyl]-amino}-acetic acid;

{[1-(4-Fluoro-phenoxy)-4-hydroxy-isoquinoline-3-carbonyl]-amino}-acetic acid;

{[1-(2-Fluoro-phenoxy)-4-hydroxy-isoquinoline-3-carbonyl]-amino}-acetic acid;

{[4-Hydroxy-1-(2-methoxy-phenoxy)-isoquinoline-3-carbonyl]-amino}-acetic acid;

{[1-(4-Acetylamino-phenoxy)-4-hydroxy-isoquinoline-3-carbonyl]-amino}-acetic acid;

{[4-Hydroxy-1-(4-methanesulfonylamino-phenoxy)-isoquinoline-3-carbonyl]-amino}-acetic acid;
[(4-Hydroxy-1-phenylamino-isoquinoline-3-carbonyl)-amino]-acetic acid;
{[4-Hydroxy-6-(pyridin-3-yloxy)-isoquinoline-3-carbonyl]-amino}-acetic acid;
{[4-Hydroxy-7-(pyridin-3-yloxy)-isoquinoline-3-carbonyl]-amino}-acetic acid;
[(1-Chloro-4-methoxy-isoquinoline-3-carbonyl)-amino]-acetic acid;
[(1-Chloro-4-ethoxy-isoquinoline-3-carbonyl)-amino]-acetic acid;
[(4-Hydroxy-1-methoxy-isoquinoline-3-carbonyl)-amino]-acetic acid;
[(1-Ethoxy-4-hydroxy-isoquinoline-3-carbonyl)-amino]-acetic acid;
[(4-Acetoxy-1-phenyl-isoquinoline-3-carbonyl)-amino]acetic acid;
[(4-Hydroxy-1-phenyl-isoquinoline-3-carbonyl)-amino] acetic acid;
[(1-Ethoxy-4-phenyl-isoquinoline-3-carbonyl)-amino]-acetic acid;
[(1-Chloro-4-phenyl-isoquinoline-3-carbonyl)-amino]-acetic acid;
[(4-Phenyl-isoquinoline-3-carbonyl)-amino]-acetic acid;
[(4-Hydroxy-1-methyl-isoquinoline-3-carbonyl)-amino]-acetic acid;
[(4-Hydroxy-1-methoxymethyl-isoquinoline-3-carbonyl)-amino]-acetic acid;
[(1-Dimethylcarbamoyl-4-hydroxy-isoquinoline-3-carbonyl)-amino]-acetic acid;
[(4-Hydroxy-1-methyl-6-phenoxy-isoquinoline-3-carbonyl)-amino]-acetic acid;
[(4-Hydroxy-1-methyl-7-phenoxy-isoquinoline-3-carbonyl)-amino]-acetic acid;
[(4-Benzyloxy-1-methyl-7-phenoxy-isoquinoline-3-carbonyl)-amino]-acetic acid;
[(4-Ethoxy-1-methyl-7-phenoxy-isoquinoline-3-carbonyl)-amino]-acetic acid;
[(1-Dimethylcarbamoyl-4-hydroxy-7-phenoxy-isoquinoline-3-carbonyl)-amino]-acetic acid;
[(4-Hydroxy-1-methoxymethyl-7-phenoxy-isoquinoline-3-carbonyl)-amino]-acetic acid;
[(4-Hydroxy-1-p-tolyl-isoquinoline-3-carbonyl)-amino]acetic acid;
{[7-(4-Fluoro-phenoxy)-4-hydroxy-1-methyl-isoquinoline-3-carbonyl]-amino}-acetic acid;
{[1-Chloro-4-hydroxy-7-(4-methoxy-phenoxy)-isoquinoline-3-carbonyl]-amino}-acetic acid;
{[4-Hydroxy-7-(4-methoxy-phenoxy)-isoquinoline-3-carbonyl]-amino}-acetic acid;
{[1-Chloro-4-hydroxy-6-(4-methoxy-phenoxy)-isoquinoline-3-carbonyl]-amino}-acetic acid;
{[4-Hydroxy-6-(4-methoxy-phenoxy)-isoquinoline-3-carbonyl]-amino}-acetic acid;
{[1-Chloro-4-hydroxy-7-(4-trifluoromethyl-phenoxy)-isoquinoline-3-carbonyl]-amino}-acetic acid;
{[4-Hydroxy-7-(4-trifluoromethyl-phenoxy)-isoquinoline-3-carbonyl]-amino}-acetic acid;
{[1-Chloro-4-hydroxy-6-(4-trifluoromethyl-phenoxy)-isoquinoline-3-carbonyl]-amino}-acetic acid;
{[4-Hydroxy-6-(4-trifluoromethyl-phenoxy)-isoquinoline-3-carbonyl]-amino}-acetic acid;
{[1-Chloro-7-(4-fluoro-phenoxy)-4-hydroxy-isoquinoline-3-carbonyl]-amino}-acetic acid;
{[7-(4-Fluoro-phenoxy)-4-hydroxy-isoquinoline-3-carbonyl]-amino}-acetic acid;
{[1-Chloro-6-(4-fluoro-phenoxy)-4-hydroxy-isoquinoline-3-carbonyl]-amino}-acetic acid;
{[6-(4-Fluoro-phenoxy)-4-hydroxy-isoquinoline-3-carbonyl]-amino}-acetic acid;
{[4-Hydroxy-7-(pyridin-4-ylsulfanyl)-isoquinoline-3-carbonyl]-amino}-acetic acid;
{[4-Hydroxy-6-(pyridin-4-ylsulfanyl)-isoquinoline-3-carbonyl]-amino}-acetic acid;
[(7-Benzenesulfinyl-4-hydroxy-isoquinoline-3-carbonyl)-amino]-acetic acid;
[(7-Benzenesulfonyl-4-hydroxy-isoquinoline-3-carbonyl)-amino]-acetic acid;
[(6-Benzenesulfinyl-4-hydroxy-isoquinoline-3-carbonyl)-amino]-acetic acid;
[(6-Benzenesulfonyl-4-hydroxy-isoquinoline-3-carbonyl)-amino]-acetic acid;
[(6-Amino-4-hydroxy-isoquinoline-3-carbonyl)-amino]-acetic acid;
{[4-Hydroxy-7-(4-methoxy-benzenesulfonylamino)-isoquinoline-3-carbonyl]-amino}-acetic acid;
{[4-Hydroxy-7-(3-phenyl-ureido)-isoquinoline-3-carbonyl]-amino}-acetic acid;
{[4-Hydroxy-6-(3-phenyl-ureido)-isoquinoline-3-carbonyl]-amino}-acetic acid;
[(4-Hydroxy-1-phenylsulfanyl-isoquinoline-3-carbonyl)-amino]-acetic acid;
{[1-(4-Chloro-phenylsulfanyl)-4-hydroxy-isoquinoline-3-carbonyl]-amino}-acetic acid;
[(4-Hydroxy-1-p-tolylsulfanyl-isoquinoline-3-carbonyl)-amino]-acetic acid;
{[4-Hydroxy-1-(pyridin-2-ylsulfanyl)-isoquinoline-3-carbonyl]-amino}-acetic acid;
{[4-Hydroxy-1-(3-methoxy-phenylsulfanyl)-isoquinoline-3-carbonyl]-amino}-acetic acid;
{[4-Hydroxy-1-(2-methoxy-phenylsulfanyl)-isoquinoline-3-carbonyl]-amino}-acetic acid;
{[4-Hydroxy-1-(naphthalen-2-ylsulfanyl)-isoquinoline-3-carbonyl]-amino}-acetic acid;
[(1-Benzenesulfinyl-4-hydroxy-isoquinoline-3-carbonyl)-amino]-acetic acid;
[(1-Benzenesulfonyl-4-hydroxy-isoquinoline-3-carbonyl)-amino]-acetic acid;
{[4-Hydroxy-7-(pyridin-2-ylsulfanyl)-isoquinoline-3-carbonyl]-amino}-acetic acid;
{[4-Hydroxy-6-(pyridin-2-ylsulfanyl)-isoquinoline-3-carbonyl]-amino}-acetic acid;
[(1-Chloro-4-hydroxy-6,7-diphenoxy-isoquinoline-3-carbonyl)-amino]-acetic acid;
[(4-Hydroxy-6,7-diphenoxy-isoquinoline-3-carbonyl)-amino]-acetic acid;
({4-Hydroxy-7-[4-(toluene-4-sulfonylamino)-phenoxy]-isoquinoline-3-carbonyl}-amino)-acetic acid;
{[4-Hydroxy-7-(4-nitro-phenoxy)-isoquinoline-3-carbonyl]-amino}-acetic acid;
[(4-Mercapto-7-phenoxy-isoquinoline-3-carbonyl)-amino] acetic acid;
[(4-Mercapto-7-trifluoromethyl-isoquinoline-3-carbonyl)-amino]-acetic acid;
{[7-(4-Benzenesulfonylamino-phenoxy)-4-hydroxy-isoquinoline-3-carbonyl]-amino}-acetic acid;
{[4-Hydroxy-7-(4-methanesulfonylamino-phenoxy)-isoquinoline-3-carbonyl]-amino}-acetic acid;
{[7-(4-Chloro-phenoxy)-4-hydroxy-isoquinoline-3-carbonyl]-amino}-acetic acid;
{[6-(4-Chloro-phenoxy)-4-hydroxy-isoquinoline-3-carbonyl]-amino}-acetic acid;

{[6-(3-Fluoro-5-methoxy-phenoxy)-4-hydroxy-isoquinoline-3-carbonyl]-amino}-acetic acid;
{[7-(3-Fluoro-5-methoxy-phenoxy)-4-hydroxy-isoquinoline-3-carbonyl]-amino}-acetic acid;
{[7-(3,4-Difluoro-phenoxy)-4-hydroxy-isoquinoline-3-carbonyl]-amino}-acetic acid;
{[6-(3,4-Difluoro-phenoxy)-4-hydroxy-isoquinoline-3-carbonyl]-amino}-acetic acid;
{[4-Hydroxy-7-(4-trifluoromethoxy-phenoxy)-isoquinoline-3-carbonyl]-amino}-acetic acid;
{[4-Hydroxy-6-(4-trifluoromethoxy-phenoxy)-isoquinoline-3-carbonyl]-amino}-acetic acid;
2-(S)-{[7-(4-Chloro-phenoxy)-4-hydroxy-isoquinoline-3-carbonyl]-amino}-propionic acid;
2-(S)-{[6-(4-Chloro-phenoxy)-4-hydroxy-isoquinoline-3-carbonyl]-amino}-propionic acid;
2-{[7-(3,4-Difluoro-phenoxy)-4-hydroxy-isoquinoline-3-carbonyl]-amino}-propionic acid;
2-(S)-[(4-Hydroxy-7-phenylsulfanyl-isoquinoline-3-carbonyl)-amino]-propionic acid;
2-(R)-[(4-Hydroxy-7-phenylsulfanyl-isoquinoline-3-carbonyl)-amino]-propionic acid;
2-(R)-[(4-Hydroxy-7-phenoxy-isoquinoline-3-carbonyl)-amino]-propionic acid;
2-(S)-{[4-Hydroxy-7-(4-methoxy-phenoxy)-isoquinoline-3-carbonyl]-amino}-propionic acid;
2-(S)-[(7-Benzenesulfonyl-4-hydroxy-isoquinoline-3-carbonyl)-amino]-propionic acid;
(R)-2-[(4-Hydroxy-1-methoxymethyl-7-phenoxy-isoquinoline-3-carbonyl)-amino]-propionic acid;
(S)-2-[(4-Hydroxy-1-methoxymethyl-7-phenoxy-isoquinoline-3-carbonyl)-amino]-propionic acid;
(S)-2-[(4-Mercapto-7-phenoxy-isoquinoline-3-carbonyl)-amino]-propionic acid;
(S)-2-{[1-(4-Chloro-phenylsulfanyl)-4-hydroxy-isoquinoline-3-carbonyl]-amino}-propionic acid;
(R)-2-{[1-(4-Chloro-phenylsulfanyl)-4-hydroxy-isoquinoline-3-carbonyl]-amino}-propionic acid;
[(4-Hydroxy-7-phenylsulfanyl-isoquinoline-3-carbonyl)-amino]-acetic acid;
[(4-Hydroxy-6-phenylsulfanyl-isoquinoline-3-carbonyl)-amino]-acetic acid;
[(1-Chloro-4-hydroxy-7-phenylsulfanyl-isoquinoline-3-carbonyl)-amino]-acetic acid;
[(1-Chloro-4-hydroxy-6-phenylsulfanyl-isoquinoline-3-carbonyl)-amino]-acetic acid;
[(1-Bromo-4-hydroxy-7-phenylsulfanyl-isoquinoline-3-carbonyl)-amino]-acetic acid;
[(1-Bromo-4-hydroxy-6-phenylsulfanyl-isoquinoline-3-carbonyl)-amino]-acetic acid;
[(4-Hydroxy-7-phenoxy-isoquinoline-3-carbonyl)-amino]-acetic acid;
[(4-Hydroxy-6-phenoxy-isoquinoline-3-carbonyl)-amino]-acetic acid;
[(1-Chloro-4-hydroxy-7-phenoxy-isoquinoline-3-carbonyl)-amino]-acetic acid;
[(1-Chloro-4-hydroxy-6-phenoxy-isoquinoline-3-carbonyl)-amino]-acetic acid;
[(1-Bromo-4-hydroxy-7-phenoxy-isoquinoline-3-carbonyl)-amino]-acetic acid;
[(1-Bromo-4-hydroxy-6-phenoxy-isoquinoline-3-carbonyl)-amino]-acetic acid;
{[7-(2,6-Dimethyl-phenoxy)-4-hydroxy-isoquinoline-3-carbonyl]-amino}-acetic acid;
{[1-Chloro-7-(2,6-dimethyl-phenoxy)-4-hydroxy-isoquinoline-3-carbonyl]-amino}-acetic acid;
{[1-Bromo-7-(2,6-dimethyl-phenoxy)-4-hydroxy-isoquinoline-3-carbonyl]-amino}-acetic acid;
[(1-Bromo-7-chloro-4-hydroxy-isoquinoline-3-carbonyl)-amino]-acetic acid;
[(1-Bromo-6-chloro-4-hydroxy-isoquinoline-3-carbonyl)-amino]-acetic acid;
[(1-Bromo-4-hydroxy-7-trifluoromethyl-isoquinoline-3-carbonyl)-amino]-acetic acid;
[(1-Bromo-4-hydroxy-6-trifluoromethyl-isoquinoline-3-carbonyl)-amino]-acetic acid;
[(4-Hydroxy-1-phenoxy-isoquinoline-3-carbonyl)-amino]-acetic acid;
[(1,7-dibromo-4-hydroxy-isoquinoline-3-carbonyl)-amino]-acetic acid;
[(7-Bromo-1-chloro-4-hydroxy-isoquinoline-3-carbonyl)-amino]-acetic acid;
[(6-Bromo-4-hydroxy-isoquinoline-3-carbonyl)-amino]acetic acid;
[(1-Bromo-7-fluoro-4-hydroxy-isoquinoline-3-carbonyl)-amino]-acetic acid;
[(7-Fluoro-4-hydroxy-isoquinoline-3-carbonyl)-amino]-acetic acid;
[(1-Chloro-7-fluoro-4-hydroxy-isoquinoline-3-carbonyl)-amino]-acetic acid;
[(1-Chloro-4-hydroxy-benzo[g]isoquinoline-3-carbonyl)-amino]-acetic acid;
[(1-Bromo-4-hydroxy-isoquinoline-3-carbonyl)-amino]-acetic acid;
[(4-Hydroxy-6-phenyl-isoquinoline-3-carbonyl)-amino]-acetic acid;
[(4-Hydroxy-7-phenyl-isoquinoline-3-carbonyl)-amino]-acetic acid;
[(1-Chloro-4-hydroxy-6-phenyl-isoquinoline-3-carbonyl)-amino]-acetic acid;
[(1-Chloro-4-hydroxy-7-phenyl-isoquinoline-3-carbonyl)-amino]-acetic acid;
[(1-Bromo-4-hydroxy-6-phenyl-isoquinoline-3-carbonyl)-amino]-acetic acid;
[(1-Bromo-4-hydroxy-7-phenyl-isoquinoline-3-carbonyl)-amino]-acetic acid;
[(4-Hydroxy-5-phenyl-isoquinoline-3-carbonyl)-amino]-acetic acid;
[(4-Hydroxy-8-phenyl-isoquinoline-3-carbonyl)-amino]-acetic acid;
[(1-Chloro-4-hydroxy-5-phenyl-isoquinoline-3-carbonyl)-amino]-acetic acid;
[(1-Chloro-4-hydroxy-8-phenyl-isoquinoline-3-carbonyl)-amino]-acetic acid;
[(1-Bromo-4-hydroxy-5-phenyl-isoquinoline-3-carbonyl)-amino]-acetic acid;
[(1-Bromo-4-hydroxy-8-phenyl-isoquinoline-3-carbonyl)-amino]-acetic acid;
[(1-Ethylsulfanyl-4-hydroxy-isoquinoline-3-carbonyl)-amino]-acetic acid;
{[4-Hydroxy-1-(4-methoxy-phenylsulfanyl)-isoquinoline-3-carbonyl]-amino}-acetic acid;
[(1-Chloro-4-hydroxy-7-iodo-isoquinoline-3-carbonyl)-amino]-acetic acid;
[(1-Chloro-4-hydroxy-6-iodo-isoquinoline-3-carbonyl)-amino]-acetic acid;
[(4-Hydroxy-7-iodo-isoquinoline-3-carbonyl)-amino]acetic acid;
[(1-Bromo-4-hydroxy-7-methyl-isoquinoline-3-carbonyl)-amino]-acetic acid;
[(1-Bromo-7-butoxy-4-hydroxy-isoquinoline-3-carbonyl)-amino]-acetic acid;

[(1-Bromo-6-butoxy-4-hydroxy-isoquinoline-3-carbonyl)-amino]-acetic acid;
[(6-Benzyloxy-1-chloro-4-hydroxy-isoquinoline-3-carbonyl)-methyl-amino]-acetic acid;
[(1-Chloro-4-hydroxy-isoquinoline-3-carbonyl)-methyl-amino]-acetic acid;
[(1-Chloro-4-hydroxy-6-isopropoxy-isoquinoline-3-carbonyl)-methyl-amino]-acetic acid;
[(1-Chloro-4-hydroxy-7-isopropoxy-isoquinoline-3-carbonyl)-methyl-amino]-acetic acid;
[Carboxymethyl-(1-chloro-4-hydroxy-isoquinoline-3-carbonyl)-amino]-acetic acid;
[Carboxymethyl-(1-chloro-4-hydroxy-6-isopropoxy-isoquinoline-3-carbonyl)-amino]-acetic acid;
1-Chloro-4-hydroxy-isoquinoline-3-carboxylic acid (2-amino-ethyl)-amide (trifluoro-acetic acid salt);
1-Chloro-4-hydroxy-isoquinoline-3-carboxylic acid (2-methoxy-ethyl)-amide;
1-Chloro-4-hydroxy-isoquinoline-3-carboxylic acid (2-hydroxy-ethyl)-amide;
1-Chloro-4-hydroxy-isoquinoline-3-carboxylic acid (2-dimethylamino-ethyl)-amide;
1-Chloro-4-hydroxy-isoquinoline-3-carboxylic acid (2-acetylamino-ethyl)-amide;
1-Chloro-4-hydroxy-6-isopropoxy-isoquinoline-3-carboxylic acid (2-hydroxy-ethyl)-amide;
1-Chloro-4-hydroxy-6-isopropoxy-isoquinoline-3-carboxylic acid (2-methoxy-ethyl)-amide;
1-Chloro-4-hydroxy-6-isopropoxy-isoquinoline-3-carboxylic acid (2-amino-ethyl)-amide (trifluoro-acetic acid salt);
1-Chloro-4-hydroxy-6-isopropoxy-isoquinoline-3-carboxylic acid (2-dimethylamino-ethyl)-amide;
1-Chloro-4-hydroxy-7-isopropoxy-isoquinoline-3-carboxylic acid (2-amino-ethyl)-amide (trifluoro-acetic acid salt);
1-Chloro-4-hydroxy-7-isopropoxy-isoquinoline-3-carboxylic acid (2-methoxy-ethyl)-amide;
1-Chloro-4-hydroxy-7-isopropoxy-isoquinoline-3-carboxylic acid (2-dimethylamino-ethyl)-amide;
1-Chloro-4-hydroxy-7-isopropoxy-isoquinoline-3-carboxylic acid (2-hydroxy-ethyl)-amide;
(S)-2-[(6-Benzyloxy-1-chloro-4-hydroxy-isoquinoline-3-carbonyl)-amino]-propionic acid;
(R)-2-[(1-Chloro-4-hydroxy-isoquinoline-3-carbonyl)-amino]-3-hydroxy-propionic acid;
(S)-2-[(1-Chloro-4-hydroxy-isoquinoline-3-carbonyl)-amino]-3-hydroxy-propionic acid;
(R)-2-[(1-Chloro-4-hydroxy-6-isopropoxy-isoquinoline-3-carbonyl)-amino]-3-hydroxy-propionic acid;
(S)-2-[(1-Chloro-4-hydroxy-6-isopropoxy-isoquinoline-3-carbonyl)-amino]-3-hydroxy-propionic acid;
(R)-2-[(1-Chloro-4-hydroxy-7-isopropoxy-isoquinoline-3-carbonyl)-amino]-3-hydroxy-propionic acid;
(S)-2-[(1-Chloro-4-hydroxy-7-isopropoxy-isoquinoline-3-carbonyl)-amino]-3-hydroxy-propionic acid;
2-[(1-Chloro-4-hydroxy-isoquinoline-3-carbonyl)-amino]-2-methyl-propionic acid;
2-[(1-Chloro-4-hydroxy-6-isopropoxy-isoquinoline-3-carbonyl)-amino]-2-methyl-propionic acid;
(R)-2-[(1-Chloro-4-hydroxy-isoquinoline-3-carbonyl)-amino]-3-(1H-imidazol-4-yl)-propionic acid (trifluoro-acetic acid salt);
(S)-2-[(1-Chloro-4-hydroxy-isoquinoline-3-carbonyl)-amino]-3-(1H-imidazol-4-yl)-propionic acid (trifluoro-acetic acid salt);
(R)-2-[(1-Chloro-4-hydroxy-isoquinoline-3-carbonyl)-amino]-3-methyl-butyric acid;
(S)-2-[(1-Chloro-4-hydroxy-isoquinoline-3-carbonyl)-amino]-3-methyl-butyric acid;
(R)-2-[(1-Chloro-4-hydroxy-6-isopropoxy-isoquinoline-3-carbonyl)-amino]-3-methyl-butyric acid;
(S)-2-[(1-Chloro-4-hydroxy-6-isopropoxy-isoquinoline-3-carbonyl)-amino]-3-methyl-butyric acid;
(R)-2-[(1-Chloro-4-hydroxy-7-isopropoxy-isoquinoline-3-carbonyl)-amino]-3-methyl-butyric acid;
(S)-2-[(1-Chloro-4-hydroxy-7-isopropoxy-isoquinoline-3-carbonyl)-amino]-3-methyl-butyric acid;
(S)-2-[(6-Benzyloxy-1-chloro-4-hydroxy-isoquinoline-3-carbonyl)-amino]-3-methyl-butyric acid;
(R)-2-[(1-Chloro-4-hydroxy-isoquinoline-3-carbonyl)-amino]-3-phenyl-propionic acid;
(S)-2-[(1-Chloro-4-hydroxy-isoquinoline-3-carbonyl)-amino]-3-phenyl-propionic acid;
(R)-2-[(1-Chloro-4-hydroxy-6-isopropoxy-isoquinoline-3-carbonyl)-amino]-3-phenyl-propionic acid;
(S)-2-[(1-Chloro-4-hydroxy-6-isopropoxy-isoquinoline-3-carbonyl)-amino]-3-phenyl-propionic acid;
(R)-2-[(1-Chloro-4-hydroxy-7-isopropoxy-isoquinoline-3-carbonyl)-amino]-3-phenyl-propionic acid;
(S)-2-[(1-Chloro-4-hydroxy-7-isopropoxy-isoquinoline-3-carbonyl)-amino]-3-phenyl-propionic acid;
(R)-2-[(1-Chloro-4-hydroxy-isoquinoline-3-carbonyl)-amino]-3-(4-hydroxy-phenyl)-propionic acid;
(S)-2-[(1-Chloro-4-hydroxy-isoquinoline-3-carbonyl)-amino]-3-(4-hydroxy-phenyl)-propionic acid;
(R)-2-[(1-Chloro-4-hydroxy-6-isopropoxy-isoquinoline-3-carbonyl)-amino]-3-(4-hydroxy-phenyl)-propionic acid;
(S)-2-[(1-Chloro-4-hydroxy-6-isopropoxy-isoquinoline-3-carbonyl)-amino]-3-(4-hydroxy-phenyl)-propionic acid;
(R)-2-[(1-Chloro-4-hydroxy-7-isopropoxy-isoquinoline-3-carbonyl)-amino]-3-(4-hydroxy-phenyl)-propionic acid;
(S)-2-[(1-Chloro-4-hydroxy-7-isopropoxy-isoquinoline-3-carbonyl)-amino]-3-(4-hydroxy-phenyl)-propionic acid;
(R)-2-[(1-Chloro-4-hydroxy-6-isopropoxy-isoquinoline-3-carbonyl)-amino]-pentanoic acid;
(S)-2-[(1-Chloro-4-hydroxy-6-isopropoxy-isoquinoline-3-carbonyl)-amino]-pentanoic acid;
(R)-1-(1-Chloro-4-hydroxy-isoquinoline-3-carbonyl)-pyrrolidine-2-carboxylic acid;
(S)-1-(1-Chloro-4-hydroxy-isoquinoline-3-carbonyl)-pyrrolidine-2-carboxylic acid;
(R)-1-(1-Chloro-4-hydroxy-6-isopropoxy-isoquinoline-3-carbonyl)-pyrrolidine-2-carboxylic acid;
(S)-1-(1-Chloro-4-hydroxy-6-isopropoxy-isoquinoline-3-carbonyl)-pyrrolidine-2-carboxylic acid;
(R)-6-Amino-2-[(1-chloro-4-hydroxy-isoquinoline-3-carbonyl)-amino]-hexanoic acid (trifluoro-acetic acid salt);
(S)-6-Amino-2-[(1-chloro-4-hydroxy-isoquinoline-3-carbonyl)-amino]-hexanoic acid (trifluoro-acetic acid salt);
(R)-6-Amino-2-[(1-chloro-4-hydroxy-6-isopropoxy-isoquinoline-3-carbonyl)-amino]-hexanoic acid; trifluoroacetic acid salt;
(S)-6-Amino-2-[(1-chloro-4-hydroxy-6-isopropoxy-isoquinoline-3-carbonyl)-amino]-hexanoic acid (trifluoro-acetic acid salt);
(R)-6-Amino-2-[(1-chloro-4-hydroxy-7-isopropoxy-isoquinoline-3-carbonyl)-amino]-hexanoic acid; trifluoroacetic acid salt;
(S)-6-Amino-2-[(1-chloro-4-hydroxy-7-isopropoxy-isoquinoline-3-carbonyl)-amino]-hexanoic acid (trifluoro-acetic acid salt);

(R)-2-[(1-Chloro-4-hydroxy-isoquinoline-3-carbonyl)-amino]-succinic acid;
(S)-2-[(1-Chloro-4-hydroxy-isoquinoline-3-carbonyl)-amino]-succinic acid;
(R)-2-[(1-Chloro-4-hydroxy-6-isopropoxy-isoquinoline-3-carbonyl)-amino]-succinic acid;
(S)-2-[(1-Chloro-4-hydroxy-6-isopropoxy-isoquinoline-3-carbonyl)-amino]-succinic acid;
(R)-2-[(1-Chloro-4-hydroxy-7-isopropoxy-isoquinoline-3-carbonyl)-amino]-succinic acid;
1-[(1-Chloro-4-hydroxy-isoquinoline-3-carbonyl)-amino]-cyclopropanecarboxylic acid;
1-[(1-Chloro-4-hydroxy-6-isopropoxy-isoquinoline-3-carbonyl)-amino]-cyclopropanecarboxylic acid;
Dideutero-[(1-chloro-4-hydroxy-isoquinoline-3-carbonyl)-amino]-acetic acid;
(R)-2-[(6-Benzyloxy-1-chloro-4-hydroxy-isoquinoline-3-carbonyl)-amino]-propionic acid;
(S)-2-[(7-Benzyloxy-1-chloro-4-hydroxy-isoquinoline-3-carbonyl)-amino]-propionic acid;
(R)-2-[(7-Benzyloxy-1-chloro-4-hydroxy-isoquinoline-3-carbonyl)-amino]-propionic acid;
(S)-2-[(1-Chloro-4-hydroxy-isoquinoline-3-carbonyl)-amino]-propionic acid;
(R)-2-[(1-Chloro-4-hydroxy-isoquinoline-3-carbonyl)-amino]-propionic acid;
(S)-2-[(6-Isopropoxy-1-chloro-4-hydroxy-isoquinoline-3-carbonyl)-amino]-propionic acid;
(R)-2-[6-Isopropoxy-1-chloro-4-hydroxy-isoquinoline-3-carbonyl)-amino]-propionic acid;
(S)-2-[(7-Isopropoxy-1-chloro-4-hydroxy-isoquinoline-3-carbonyl)-amino-propionic acid;
(R)-2-[(7-Isopropoxy-1-chloro-4-hydroxy-isoquinoline-3-carbonyl)-amino]propionic acid;
1-Chloro-4-hydroxy-6-isopropoxy-isoquinoline-3-carboxylic acid (2-hydroxy-1-hydroxymethyl-ethyl)-amide;
1-Chloro-4-hydroxy-7-isopropoxy-isoquinoline-3-carboxylic acid (2-hydroxy-1-hydroxymethyl-ethyl)-amide;
1-Chloro-4-hydroxy-isoquinoline-3-carboxylic acid (2-hydroxy-1-hydroxymethyl-ethyl)-amide;
{[7-(3,5-Difluoro-phenoxy)-4-hydroxy-isoquinoline-3-carbonyl]-amino}-acetic acid;
{[6-(3,5-Difluoro-phenoxy)-4-hydroxy-isoquinoline-3-carbonyl]-amino}-acetic acid;
({7-[4-(4-Fluoro-phenoxy)-phenoxy]-4-hydroxy-isoquinoline-3-carbonyl}-amino)-acetic acid;
({6-[4-(4-Fluoro-phenoxy)-phenoxy]-4-hydroxy-isoquinoline-3-carbonyl}-amino)-acetic acid;
{[7-(3-Chloro-4-fluoro-phenoxy)-4-hydroxy-isoquinoline-3-carbonyl]-amino}-acetic acid;
{[6-(3-Chloro-4-fluoro-phenoxy)-4-hydroxy-isoquinoline-3-carbonyl]-amino}-acetic acid;
(S)-2-{[7-(3-Fluoro-5-methoxy-phenoxy)-4-hydroxy-isoquinoline-3-carbonyl]-amino}-propionic acid;
2-(S)-[(7-Cyclohexyloxy-4-hydroxy-isoquinoline-3-carbonyl)-amino]-propionic acid;
2-(S)-{[7-(4-Fluoro-phenoxy)-4-hydroxy-1-methyl-isoquinoline-3-carbonyl]-amino}-propionic acid;
2-(S)-{[7-(4-Fluoro-phenoxy)-4-hydroxy-isoquinoline-3-carbonyl]-amino}-propionic acid;
2-(S)-[(4-Hydroxy-1-methyl-7-phenoxy-isoquinoline-3-carbonyl)-amino]-propionic acid;
2-(S)-[(4-Hydroxy-1-methyl-7-phenylsulfanyl-isoquinoline-3-carbonyl)-amino]-propionic acid;
2-(S)-{[4-Hydroxy-7-(4-trifluoromethyl-phenoxy)-isoquinoline-3-carbonyl]-amino}-propionic acid;
{[7-(4-Chloro-phenoxy)-4-hydroxy-1-methyl-isoquinoline-3-carbonyl]-amino}-acetic acid;
{[6-(4-Chloro-phenoxy)-4-hydroxy-1-methyl-isoquinoline-3-carbonyl]-amino}-acetic acid;
{[7-(3,5-Difluoro-phenoxy)-4-hydroxy-1-methyl-isoquinoline-3-carbonyl]-amino}-acetic acid;
{[4-Hydroxy-7-(4-methoxy-phenoxy)-1-methyl-isoquinoline-3-carbonyl]-amino}-acetic acid;
{[4-Hydroxy-6-(4-methoxy-phenoxy)-1-methyl-isoquinoline-3-carbonyl]-amino}-acetic acid;
[(6-Cyclohexyloxy-4-hydroxy-isoquinoline-3-carbonyl)-amino]-acetic acid;
[(7-Cyclohexyloxy-4-hydroxy-isoquinoline-3-carbonyl)-amino]-acetic acid;
[(7-Cyclohexyloxy-4-hydroxy-1-methyl-isoquinoline-3-carbonyl)-amino]-acetic acid;
[(7-Cyclohexylsulfanyl-4-hydroxy-isoquinoline-3-carbonyl)-amino]-acetic acid;
[(7-Cyclohexanesulfonyl-4-hydroxy-isoquinoline-3-carbonyl)-amino]-acetic acid;
[(4-Hydroxy-1-isobutyl-isoquinoline-3-carbonyl)-amino] acetic acid;
[(4-Hydroxy-1-pyridin-2-yl-isoquinoline-3-carbonyl)-amino]-acetic acid;
[(1-Ethyl-4-hydroxy-7-phenoxy-isoquinoline-3-carbonyl)-amino]-acetic acid;
[(1-Dimethylaminomethyl-4-hydroxy-7-phenylsulfanyl-isoquinoline-3-carbonyl)-amino]-acetic acid;
[(4-Hydroxy-1-methyl-7-phenylsulfanyl-isoquinoline-3-carbonyl)-amino]-acetic acid;
{[4-Hydroxy-1-methyl-7-(4-trifluoromethyl-phenoxy)-isoquinoline-3-carbonyl]-amino}-acetic acid;
[(1-Chloro-4-hydroxy-isoquinoline-3-carbonyl)-amino]-acetic acid;
[(7-Chloro-3-hydroxy-quinoline-2-carbonyl)-amino]-acetic acid;
[(3-Hydroxy-6-phenoxy-quinoline-2-carbonyl)-amino]acetic acid;
[(1-Chloro-4-hydroxy-5-methyl-isoquinoline-3-carbonyl)-amino]-acetic acid;
[(4-Hydroxy-7-phenylsulfanyl-isoquinoline-3-carbonyl)-amino]-acetic acid;
2-[(4-Hydroxy-7-phenoxy-isoquinoline-3-carbonyl)-amino]-propionic acid;
[(4-Chloro-7-hydroxy-thieno[3,2-c]pyridine-6-carbonyl)-amino]-acetic acid;
[(7-Ethynyl-4-hydroxy-thieno[2,3-c]pyridine-5-carbonyl)-amino]-acetic acid;
{[4-Hydroxy-7-(2-methyl-benzooxazol-6-yloxy)-isoquinoline-3-carbonyl]-amino}-acetic acid;
{[7-(Benzo[1,3]dioxol-5-yloxy)-4-hydroxy-isoquinoline-3-carbonyl]-amino}-acetic acid;
{[2-(4-Fluoro-phenyl)-4-hydroxy-7-methyl-thieno[2,3-c]pyridine-5-carbonyl]-amino}-acetic acid;
{[2-(4-Chloro-phenyl)-6-hydroxy-thieno[3,2-b]pyridine-5-carbonyl]-amino}-acetic acid;
{[1-Cyano-7-(4-fluoro-phenoxy)-4-hydroxy-isoquinoline-3-carbonyl]-amino}-acetic acid;
[(7-Chloro-1-cyano-4-hydroxy-isoquinoline-3-carbonyl)-amino]-acetic acid;
[(7-Chloro-3-hydroxy-4-iodo-quinoline-2-carbonyl)-amino]-acetic acid;
[(1-Cyano-4-hydroxy-8-phenoxy-isoquinoline-3-carbonyl)-amino]-acetic acid;
{[7-(2,3-Dihydro-benzofuran-5-yloxy)-4-hydroxy-isoquinoline-3-carbonyl]-amino}-acetic acid;

2-[(4-Hydroxy-7-phenylsulfanyl-isoquinoline-3-carbonyl)-amino]-propionic acid;
[(2,4-Dibromo-7-hydroxy-thieno[3,2-c]pyridine-6-carbonyl)-amino]-acetic acid;
[(4-Bromo-7-hydroxy-thieno[3,2-c]pyridine-6-carbonyl)-amino]-acetic acid;
{[4-Hydroxy-1-methyl-7-(2-methyl-benzooxazol-6-yloxy)-isoquinoline-3-carbonyl]-amino}-acetic acid;
[(7-Hydroxy-2-phenoxy-thieno[3,2-c]pyridine-6-carbonyl)-amino]-acetic acid;
[(4-Cyano-7-hydroxy-thieno[3,2-c]pyridine-6-carbonyl)-amino]-acetic acid;
[(4-Furan-3-yl-7-hydroxy-thieno[3,2-c]pyridine-6-carbonyl)-amino]-acetic acid;
{[2,3-Bis-(4-fluoro-phenyl)-7-hydroxy-thieno[3,2-c]pyridine-6-carbonyl]amino}-acetic acid;
[(1-Formyl-4-hydroxy-6-phenoxy-isoquinoline-3-carbonyl)-amino]-acetic acid;
{[1-Cyano-6-(2,6-dimethyl-phenoxy)-4-hydroxy-isoquinoline-3-carbonyl]-amino}-acetic acid;
[(1-Cyano-4-hydroxy-5-phenoxy-isoquinoline-3-carbonyl)-amino]-acetic acid;
{[6-(Benzo[1,3]dioxol-5-yloxy)-1-cyano-4-hydroxy-isoquinoline-3-carbonyl]-amino}-acetic acid;
{[1-Cyano-6-(2,3-dihydro-benzofuran-5-yloxy)-4-hydroxy-isoquinoline-3-carbonyl]-amino}-acetic acid;
{[1-Cyano-4-hydroxy-8-(3-methoxy-phenoxy)-isoquinoline-3-carbonyl]-amino}-acetic acid;
{[1-Cyano-4-hydroxy-6-(2-methyl-benzooxazol-6-yloxy)-isoquinoline-3-carbonyl]-amino}-acetic acid;
[(7-Benzyl-1-cyano-4-hydroxy-isoquinoline-3-carbonyl)-amino]-acetic acid;
{[1-Cyano-5-(4-fluoro-phenoxy)-4-hydroxy-isoquinoline-3-carbonyl]-amino}-acetic acid;
[(7-Chloro-4-ethyl-3-hydroxy-quinoline-2-carbonyl)-amino]-acetic acid;
{[7-Chloro-3-hydroxy-4-(3-trifluoromethyl-phenyl)-quinoline-2-carbonyl]-amino}-acetic acid;
[(6,7-Dichloro-4-hydroxy-isoquinoline-3-carbonyl)-amino]acetic acid;
[(1-Cyano-4-hydroxy-7-phenoxy-isoquinoline-3-carbonyl)-amino]-acetic acid;
{[8-(4-Fluoro-phenoxy)-4-hydroxy-1-methyl-isoquinoline-3-carbonyl]-amino}-acetic acid;
{[1-Cyano-8-(4-fluoro-phenoxy)-4-hydroxy-isoquinoline-3-carbonyl]-amino}-acetic acid
[(1-Cyano-4-hydroxy-6-phenoxy-isoquinoline-3-carbonyl)-amino]-acetic acid;
{[1-Cyano-6-(4-fluoro-phenoxy)-4-hydroxy-isoquinoline-3-carbonyl]-amino}-acetic acid;
and pharmaceutically acceptable salts, esters and prodrugs thereof.

In particular embodiments, an agent of the present invention is selected from the group consisting of a quinoline-2-carboxamide, an isoquinoline-3-carboxamide, a cinnoline-3-carboxamide, a beta-carboline-3-carboxamide, a thienopyridine, or an N-substituted arylsulfonylamino hydroxamate. In certain embodiments, the quinoline-2-carboxamide is a compound of Formula Ia. In certain embodiments, the isoquinoline-3-carboxamide is a compound of Formula Ib, Formula IV, Formula IVA, Formula IVB, Formula IVC, Formula IVD, Formula V, Formula VA, Formula VB, Formula VC, or Formula VD. In certain embodiments, the cinnoline-3-carboxamide is a compound of Formula Ic. In certain embodiments, the beta-carboline-3-carboxamide is a compound of Formula Id. In certain embodiments, the thienopyridine is a compound of Formula II. In certain embodiments, the N-substituted arylsulfonylamino hydroxamate is a compound of Formula III or Formula IIIa.

In particular embodiments, an agent for use in the present methods is selected from the group consisting of: [(1-Chloro-4-hydroxy-isoquinoline-3-carbonyl)-amino]-acetic acid (Compound A); [(7-Chloro-3-hydroxy-quinoline-2-carbonyl)-amino]-acetic acid (Compound B); [(3-Hydroxy-6-phenoxy-quinoline-2-carbonyl)-amino]-acetic acid (Compound C); [(1-Chloro-4-hydroxy-5-methyl-isoquinoline-3-carbonyl)-amino]-acetic acid (Compound D); [(4-Hydroxy-7-phenylsulfanyl-isoquinoline-3-carbonyl)-amino]-acetic acid (Compound E); {[4-Hydroxy-7-(4-methoxy-phenoxy)-isoquinoline-3-carbonyl]-amino}-acetic acid (Compound F); {[7-(4-Fluoro-phenoxy)-4-hydroxy-isoquinoline-3-carbonyl]-amino}-acetic acid (Compound G); {[1-Chloro-4-hydroxy-6-(4-methoxy-phenoxy)-isoquinoline-3-carbonyl]-amino}-acetic acid (Compound H); 2-[(4-Hydroxy-7-phenoxy-isoquinoline-3-carbonyl)-amino]-propionic acid (Compound I); [(4-Hydroxy-1-methyl-7-phenoxy-isoquinoline-3-carbonyl)-amino]-acetic acid (Compound J); [(4-Benzyloxy-1-methyl-7-phenoxy-isoquinoline-3-carbonyl)-amino]-acetic acid (Compound K); [(4-Chloro-7-hydroxy-thieno[3,2-c]pyridine-6-carbonyl)-amino]-acetic acid (Compound L); [(7-Ethynyl-4-hydroxy-thieno[2,3-c]pyridine-5-carbonyl)-amino]-acetic acid (Compound M); {[4-Hydroxy-7-(2-methyl-benzooxazol-6-yloxy)-isoquinoline-3-carbonyl]-amino}-acetic acid (Compound N); {[7-(Benzo[1,3]dioxol-5-yloxy)-4-hydroxy-isoquinoline-3-carbonyl]-amino}-acetic acid (Compound O); {[2-(4-Fluoro-phenyl)-4-hydroxy-7-methyl-thieno[2,3-c]pyridine-5-carbonyl]-amino}-acetic acid (Compound P); {[2-(4-Chloro-phenyl)-6-hydroxy-thieno[3,2-b]pyridine-5-carbonyl]-amino}-acetic acid (Compound Q); {[1-Cyano-7-(4-fluoro-phenoxy)-4-hydroxy-isoquinoline-3-carbonyl]-amino}-acetic acid (Compound R); [(7-Chloro-1-cyano-4-hydroxy-isoquinoline-3-carbonyl)-amino]-acetic acid (Compound S); [(7-Chloro-3-hydroxy-4-iodo-quinoline-2-carbonyl)-amino]acetic acid (Compound T); {[1-(4-Chloro-phenylsulfanyl)-4-hydroxy-isoquinoline-3-carbonyl]-amino}-acetic acid (Compound U); [(7-Cyclohexylsulfanyl-4-hydroxy-isoquinoline-3-carbonyl)-amino]-acetic acid (Compound V); [(1-Cyano-4-hydroxy-8-phenoxy-isoquinoline-3-carbonyl)-amino]-acetic acid (Compound W); {[7-(2,3-Dihydro-benzofuran-5-yloxy)-4-hydroxy-isoquinoline-3-carbonyl]-amino}-acetic acid (Compound X); 2-[(4-Hydroxy-7-phenylsulfanyl-isoquinoline-3-carbonyl)-amino]-propionic acid (Compound Y); {[1-(2-Fluoro-phenoxy)-4-hydroxy-isoquinoline-3-carbonyl]-amino}-acetic acid (Compound Z); [(4-Hydroxy-1-methyl-6-phenoxy-isoquinoline-3-carbonyl)-amino]-acetic acid (Compound AA); and {[4-Hydroxy-6-(pyridin-2-ylsulfanyl)-isoquinoline-3-carbonyl]-amino}-acetic acid (Compound AB).

Other exemplary compounds of the invention include: [(4-Hydroxy-7-phenoxy-isoquinoline-3-carbonyl)-amino]-acetic acid (Compound AC); [(2,4-Dibromo-7-hydroxy-thieno[3,2-c]pyridine-6-carbonyl)-amino]-acetic acid (Compound AD); [(4-Bromo-7-hydroxy-thieno[3,2-c]pyridine-6-carbonyl)-amino]-acetic acid (Compound AE); {[4-Hydroxy-1-methyl-7-(2-methyl-benzooxazol-6-yloxy)-isoquinoline-3-carbonyl]-amino}-acetic acid (Compound AF); [(7-Hydroxy-2-phenoxy-thieno[3,2-c]pyridine-6-carbonyl)-amino]-acetic acid (Compound AG); [(4-Cyano-7-hydroxy-thieno[3,2-c]pyridine-6-carbonyl)-amino]-acetic acid (Compound AH); [(4-Furan-3-yl-7-hydroxy-thieno[3,2-c]pyridine-6-carbonyl)-amino]-acetic acid (Compound AI); {[2,3-Bis-(4-fluoro-phenyl)-7-hydroxy-thieno[3,2-c]pyridine-6-carbonyl]-amino}-acetic acid (Compound AJ); [(1-

Formyl-4-hydroxy-6-phenoxy-isoquinoline-3-carbonyl)-amino]-acetic acid (Compound AK); {[1-Cyano-6-(2,6-dimethyl-phenoxy)-4-hydroxy-isoquinoline-3-carbonyl]-amino}-acetic acid (Compound AL); [(1-Cyano-4-hydroxy-5-phenoxy-isoquinoline-3-carbonyl)-amino]-acetic acid (Compound AM); {[6-(Benzo[1,3]dioxol-5-yloxy)-1-cyano-4-hydroxy-isoquinoline-3-carbonyl]-amino}-acetic acid (Compound AN); {[1-Cyano-6-(2,3-dihydro-benzofuran-5-yloxy)-4-hydroxy-isoquinoline-3-carbonyl]-amino}-acetic acid (Compound AO); {[1-Cyano-4-hydroxy-8-(3-methoxy-phenoxy)-isoquinoline-3-carbonyl]-amino}-acetic acid (Compound AP); {[1-Cyano-4-hydroxy-6-(2-methyl-benzooxazol-6-yloxy)-isoquinoline-3-carbonyl]-amino}-acetic acid (Compound AQ); [(7-Benzyl-1-cyano-4-hydroxy-isoquinoline-3-carbonyl)-amino]-acetic acid (Compound AR); {[1-Cyano-5-(4-fluoro-phenoxy)-4-hydroxy-isoquinoline-3-carbonyl]-amino}-acetic acid (Compound AS); [(7-Chloro-4-ethyl-3-hydroxy-quinoline-2-carbonyl)-amino]-acetic acid (Compound AT); {[7-Chloro-3-hydroxy-4-(3-trifluoromethyl-phenyl)-quinoline-2-carbonyl]-amino}-acetic acid (Compound AU); [(6,7-Dichloro-4-hydroxy-isoquinoline-3-carbonyl)-amino]acetic acid (Compound AV); [(4-Hydroxy-8-phenyl-isoquinoline-3-carbonyl)-amino]-acetic acid (Compound AW); [(4-Hydroxy-6,7-diphenoxy-isoquinoline-3-carbonyl)-amino]-acetic acid (Compound AX); {[7-(4-Fluoro-phenoxy)-4-hydroxy-1-methyl-isoquinoline-3-carbonyl]-amino}-acetic acid (Compound AY); [(1-Cyano-4-hydroxy-7-phenoxy-isoquinoline-3-carbonyl)-amino]-acetic acid (Compound AZ); {[8-(4-Fluoro-phenoxy)-4-hydroxy-1-methyl-isoquinoline-3-carbonyl]-amino}-acetic acid (Compound BA); {[1-Cyano-8-(4-fluoro-phenoxy)-4-hydroxy-isoquinoline-3-carbonyl]-amino}-acetic acid (Compound BB); [(1-Cyano-4-hydroxy-6-phenoxy-isoquinoline-3-carbonyl)-amino]-acetic acid (Compound BC); and {[1-Cyano-6-(4-fluoro-phenoxy)-4-hydroxy-isoquinoline-3-carbonyl]-amino}-acetic acid (Compound BD).

As used herein, "alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group, of from 1 to 10 carbon atoms, preferably, 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{40}$R$^{40}$ where each R$^{40}$ is hydrogen or alkyl, —NR$^{40}$S(O)$_2$-alkyl, —NR$^{40}$S(O)$_2$-substituted alkyl, —NR$^{40}$S(O)$_2$-aryl, —NR$^{40}$S(O)$_2$-substituted aryl, —NR$^{40}$S(O)$_2$-heteroaryl, —NR$^{40}$S(O)$_2$-substituted heteroaryl, —NR$^{40}$S(O)$_2$-heterocyclic, —NR$^{40}$S(O)$_2$-substituted heterocyclic, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic where each R$^{40}$ is hydrogen or alkyl.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminoacyl" or as a prefix "carbamoyl" or "carboxamide" or "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 6 carbon atoms and more preferably 2 to 4 carbon atoms and having at least 1 and preferably from 1 to 2 sites of alkenyl unsaturation.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkynyl" refers to alkynyl group preferably having from 2 to 6 carbon atoms and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Substituted amino" refers to the group —NR$^{41}$R$^{41}$, where each R$^{41}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{41}$ groups are not hydrogen; or the R$^{41}$ groups can be joined together with the nitrogen atom to form a heterocyclic or substituted heterocyclic ring.

"Acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Carbonyloxyamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" or as a prefix "carbamoyloxy" or "substituted carbamoyloxy" refers to the groups —OC(O)NR$^{47}$R$^{47}$ where each R$^{47}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R$^{47}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{49}$C(O)NR$^{49}$— where R$^{49}$ is selected from the group consisting of hydrogen and alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is the aryl group. Preferred aryls include phenyl and naphthyl.

"Substituted aryl" refers to aryl groups, as defined herein, which are substituted with from 1 to 4, preferably 1-3, substituents selected from the group consisting of hydroxy, acyl, acylamino, carbonylaminothio, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{51}$R$^{51}$ where each R$^{51}$ is hydrogen or alkyl, —NR$^{51}$S(O)$_2$-alkyl, —NR$^{51}$S(O)$_2$-substituted alkyl, —NR$^{51}$S(O)$_2$-aryl, —NR$^{51}$S(O)$_2$-substituted aryl, —NR$^{51}$S(O)$_2$-heteroaryl, —NR$^{51}$S(O)$_2$-substituted heteroaryl, —NR$^{51}$S(O)$_2$-heterocyclic, —NR$^{51}$S(O)$_2$-substituted heterocyclic, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic where each R$^{51}$ is hydrogen or alkyl, wherein each of the terms is as defined herein.

"Aryloxy" refers to the group aryl-O— that includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings as defined above for substituted aryl.

"Carboxyl" refers to —COOH or salts thereof.

"Carboxyl esters" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein. "Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 15 carbon atoms, preferably from 1 to 10 carbon atoms, and 1 to 4 heteroatoms selected from the group consisting of oxygen, nitrogen and sulphur within the ring. Such heteroaryl groups can have a single ring (e.g., pyridinyl or furyl) or multiple condensed rings (e.g., indolizinyl or benzothienyl). Preferred heteroaryls include pyridinyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulphur or oxygen within the ring wherein, in fused ring systems, one or more the rings can be aryl or heteroaryl provided that the point of attachment is at the heterocycle.

"Substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" or "mercapto" refers to the group —SH.

"Alkylsulfanyl" and "alkylthio" refer to the groups —S-alkyl where alkyl is as defined above.

"Substituted alkylthio" and "substituted alkylsulfanyl" refer to the group —S-substituted alkyl is as defined above.

"Cycloalkylthio" or "cycloalkylsulfanyl" refers to the groups —S-cycloalkyl where cycloalkyl is as defined above.

"Substituted cycloalkylthio" refers to the group —S-substituted cycloalkyl where substituted cycloalkyl is as defined above.

"Arylthio" refers to the group —S-aryl and "substituted arylthio" refers to the group —S-substituted aryl where aryl and substituted aryl are as defined above.

"Heteroarylthio" refers to the group —S-heteroaryl and "substituted heteroarylthio" refers to the group —S-substituted heteroaryl where heteroaryl and substituted heteroaryl are as defined above.

"Heterocyclicthio" refers to the group —S-heterocyclic and "substituted heterocyclicthio" refers to the group —S-substituted heterocyclic where heterocyclic and substituted heterocyclic are as defined above.

The term "amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active .alpha.-Amino Acids, Pergamon Press (1989); Evans et al., J. Amer. Chem. Soc., 112:4011-4030 (1990); Pu et al., J. Amer. Chem. Soc., 56:1280-1283 (1991); Williams et al., J. Amer. Chem. Soc., 113:9276-9286 (1991); and all references cited therein. The present invention includes the side chains of unnatural amino acids as well.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "prodrug" refers to compounds of this invention which have been modified to include a physiologically and biocompatible removable group which group is removed in vivo to provide for the active drug, a pharmaceutically acceptable salt thereof or a biologically active metabolite thereof. Suitable removable groups are well known in the art and particularly preferred removable groups include esters of the carboxylic acid moiety on the glycine substituent. Preferably such esters include those derived from alkyl alcohols, substituted alkyl alcohols, hydroxy substituted aryls and heteroaryls and the like. Another preferred removable group are the amides formed from the carboxylic acid moiety on the glycine substituent. Suitable amides are derived from amines of the formula $HNR^{20}R^{21}$ where $R^{20}$ and $R^{21}$ are independently hydrogen, alkyl, substituted alkyl, aryl, substituted aryl, and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

These and other embodiments of the present invention will readily occur to those of ordinary skill in the art in view of the disclosure herein.

EXAMPLES

The invention will be further understood by reference to the following examples, which are intended to be purely exemplary of the invention. The examples are provided solely to illustrate the claimed invention. The present invention is not limited in scope by the exemplified embodiments, which are intended as illustrations of single aspects of the invention only. Any methods which are functionally equivalent are within the scope of the invention. Various modifications of the invention, in addition to those described herein, will become apparent to those skilled in the art from the foregoing description and accompanying figures. Such modifications are intended to fall within the scope of the appended claims.

Example 1

Increased Expression of Cytoprotective and Neuroprotective Factors in Hep3B Cells The effect of compounds of the present invention on expression of cytoprotective and neuroprotective factors in cells was evaluated as follows. Human cells derived from hepatocarcinoma (Hep3B) tissue (see, e.g., American Type Culture Collection, Manassas Va.) were seeded into 35 mm culture dishes and grown at 37° C., 20% $O_2$, 5% $CO_2$ in Minimal Essential Medium (MEM), Earle's balanced salt solution (Mediatech Inc., Herndon Va.), 2 mM L-glutamine, 0.1 mM non-essential amino acids, 1 mM sodium pyruvate, and 10% FBS. When cell layers reached confluence, the media was replaced with OPTI-MEM media (Invitrogen Life Technologies, Carlsbad Calif.) and cell layers were incubated for approximately 24 hours in 20% $O_2$, 5% $CO_2$ at 37° C. Various compounds of the present invention or 1% DMSO (negative control) were then added to existing media and incubation was continued overnight.

Following incubation, the conditioned media was collected from cell cultures and analyzed for erythropoietin (EPO) expression using a QUANTIKINE immunoassay (R&D Systems, Inc., Minneapolis Minn.) according to the manufacturer's instructions. As shown below in Table 1, addition of compounds of the present invention to Hep3B cells resulted in increased expression of erythropoietin (EPO). These results indicated that methods and compounds of the present invention are useful for increasing expression of cytoprotective and neuroprotective factors in cells.

TABLE 1

| Compound | EPO (mIU/ml) | Fold Increase Over Control |
| --- | --- | --- |
| A | 18.3 | 13.6 |
| B | 14.2 | 9.8 |
| C | 241.4 | 2.2 |
| D | 205.7 | 2.7 |
| E | 127.6 | 17.0 |

TABLE 1-continued

| Compound | EPO (mIU/ml) | Fold Increase Over Control |
| --- | --- | --- |
| AC | 160.1 | 10.8 |
| F | 369.4 | 3.0 |
| G | 73.4 | 5.1 |
| H | 84.0 | 5.4 |
| I | 41.0 | ND |
| J | 120.0 | ND |
| K | 57.4 | 1.8 |
| AD | 34.9 | 6.5 |
| L | 11.1 | 4.2 |
| AE | 12.6 | 3.0 |
| M | 64.1 | 11.6 |
| N | 89.9 | 13.5 |
| AF | 101.6 | 15.3 |
| O | 97.4 | 14.7 |
| X | 126.2 | 19.0 |
| P | 54.9 | 7.2 |
| Q | 37.1 | 4.8 |
| AG | 27.3 | 8.5 |
| AH | 13.4 | 7.1 |
| R | 49.1 | 25.3 |
| S | 12.5 | 10.1 |
| AI | 7.9 | 6.1 |
| T | 100.7 | 49.3 |
| AJ | 62.9 | 42.8 |
| AK | 35.3 | 14.9 |
| AL | 74.8 | 13.9 |
| AM | 44.3 | 8.2 |
| AN | 42.8 | 16.2 |
| AO | 83.4 | 83.4 |
| AP | 53.4 | 17.2 |
| AQ | 32.9 | 16.5 |
| AR | 82.7 | 21.8 |
| AS | 40.5 | 10.7 |
| AT | 81.0 | 30.0 |
| AU | 19.2 | 7.1 |

ND—Not determined

Example 2

Increased Expression of Cytoprotective and Neuroprotective Factors in Neuroblastoma Cells The effect of compounds of the present invention on expression of cytoprotective and neuroprotective factors in neuroblastoma cells was evaluated as follows. Kelly neuroblastoma cells (see, e.g., DSMZ, cat# ACC-355, Braunschweig Germany) were treated with various compounds of the present invention or 1% DMSO (negative control). Following an overnight incubation, the conditioned media was collected from cell cultures and analyzed for erythropoietin (EPO) and vascular endothelial growth factor (VEGF) expression using a QUANTIKINE immunoassay (R&D Systems, Inc., Minneapolis Minn.) according to the manufacturer's instructions. As shown below in Table 2, addition of various compounds of the present invention to Kelly neuroblastoma cells resulted in increased expression of erythropoietin (EPO) and vascular endothelial growth factor (VEGF). These results indicated that methods and compounds of the present invention are useful for increasing expression of cytoprotective and neuroprotective factors in neuronal cells.

TABLE 2

| Compound | EPO (mIU/ml) | EPO Fold Increase | VEGF (pg/ml) | VEGF Fold Increase |
|---|---|---|---|---|
| C | 21.8 | 3.5 | 1445.7 | 9.1 |
| E | 55.8 | 9.0 | 2495.8 | 15.8 |
| AC | 73.8 | 11.9 | 2503.8 | 15.8 |
| F | 65 | 10.5 | 2564.9 | 16.2 |
| G | 34.4 | 5.5 | 2271.5 | 14.4 |
| I | 14.8 | 3.4 | 2370.0 | 7.2 |
| AD | 138.2 | 7.3 | 5123.0 | 3.5 |
| L | 98.2 | 5.2 | 4750.0 | 3.3 |
| U | 8.9 | 1.4 | 1526.0 | 9.7 |
| V | 24.2 | 3.9 | 2132.0 | 13.5 |
| AE | 95.5 | 3.6 | 3710.0 | 2.7 |
| M | 57 | 285 | 1436 | 2.0 |
| N | 380.5 | 14.52 | 6316 | 4.6 |
| AF | 231.3 | 12.24 | 5124 | 3.5 |
| O | 149.8 | 7.93 | 5235 | 3.6 |
| X | 260.1 | 13.76 | 5751 | 3.9 |
| P | 262.8 | 13.90 | 7453 | 5.1 |
| Q | 52.9 | 2.80 | 6369 | 4.4 |
| AG | 273 | 14.44 | 8670 | 5.9 |
| AH | 225.8 | 11.95 | 6590 | 4.5 |
| R | 372.6 | 19.71 | 2735 | 7.4 |
| W | 214.6 | 11.35 | 1846 | 5.0 |
| S | 40.4 | 2.89 | 725 | 1.9 |
| AI | 321.6 | 17.02 | 7003 | 4.8 |
| T | 299.1 | 15.83 | 8159 | 5.6 |
| AJ | ND | ND | 4102 | 3.0 |
| AK | 42.2 | 2.23 | 5698 | 3.9 |
| AL | 213.8 | 11.31 | 5499 | 3.8 |
| AM | 118.07 | 6.25 | 5825 | 4.0 |
| AN | 251 | 13.28 | 7252 | 5.3 |
| AO | 369.5 | 19.55 | 6653 | 4.6 |
| AP | 27.2 | 1.44 | 3266 | 2.2 |
| AQ | 82 | 4.34 | 3795 | 2.6 |
| AR | 842.9 | 32.17 | 14745 | 10.8 |
| AS | 221.5 | 11.72 | 8197 | 5.6 |
| AT | 587.5 | 31.08 | 11350 | 8.3 |
| AU | 109.1 | 4.16 | 6877 | 5.1 |

Example 3

Animal Dosing

The following guidelines were used to administer compounds of the present invention to the animal subjects in the studies described herein. Animals useful for measuring in vivo effects of compounds of the present invention include Swiss Webster male mice (30-32 g), C57BL/6 male mice (25-35 g), db/db male mice (45-55 g), Sprague Dawley male rats (200-350 g), Wistar male rats (300-350 g), and Lewis female rats obtained from Simonsen, Inc. (Gilroy Calif.), Charles River (Hollister Calif.), or Harlan. Animals were maintained using standard procedures, and food and water were available to the animals ad libitum.

During treatment, animals were monitored for changes in body weight and signs of overt toxicity and mortality.

Compounds were generally administered orally by gavage (p.o.) or by intravenous (i.v.) administration. Animals treated by oral gavage received a 4-10 ml/kg volume of either 0.5% carboxymethyl cellulose (CMC; Spectrum, Gardena Calif.) with or without 0.1% Polysorbate 80 or various doses (6-60 mg/kg) of a compound of the present invention in 0.5% CMC, with or without 0.1% Polysorbate 80 (JT Baker, Phillipsburg N.J.) Animals treated by intravenous injection received a 2-6 ml/kg volume of either 5% Dextrose (Spectrum, Gardena Calif.) with an equimolar amount of NaOH (JT Baker, Phillipsburg N.J.) or Meglumine (Spectrum, Gardena Calif.) or various doses (6-60 mg/kg) of a compound of the present invention in 5% dextrose with an equimolar amount of NaOH or Meglumine. Blood samples were collected at appropriate intervals during treatment from, e.g., tail vein (rats), or abdominal vein or cardiocentesis (mice or rats). Generally, animals were anesthetized with isoflurane and blood samples were collected into MICROTAINER serum separator tubes (Becton-Dickinson, Franklin Lakes N.J.).

At the end of each study, animals were euthanized, e.g. by exsanguination under general anesthesia or by $CO_2$ asphyxiation, and organ and tissue samples were collected. Tissues were either fixed in neutral buffered formalin or stored frozen at −70° C. Tissues for genomic analysis were placed in RNAlater solution (Ambion, Austin Tex.).

Example 4

Increased Expression of Cytoprotective and Neuroprotective Factors In Vivo

The effect of compounds of the present invention on expression of cytoprotective and neuroprotective factors in vivo was evaluated as follows. In one series of experiments, male Swiss Webster mice (29-34 g) were administered various compounds of the present invention via intravenous injection into the caudal tail vein. Animals treated by intravenous injection received a 6 ml/kg volume of either 5% Dextrose with an equimolar amount of NaOH or Meglumine (vehicle control) or 20 mg/kg of a compound of the present invention in 5% dextrose with an equimolar amount of NaOH or Meglumine. Four hours after injection, the animals were anesthetized and exsanguinated. Plasma samples were collected in EDTA and heparin coated microtainer tubes. Plasma samples were assayed for erythropoietin and VEGF using commercially-available ELISA kits purchased from R & D Systems (Minneapolis Minn.).

As shown below in Table 3, administration of various compounds of the present invention by intravenous injection into mice increased systemic levels of EPO and VEGF. These results indicated that methods and compounds of the present invention are useful for increasing expression of various cytoprotective and neuroprotective factors in vivo. These results further showed that systemic expression of cytoprotective and neuroprotective factors increased following intravenous administration of various compounds of the present invention.

TABLE 3

| Compound | EPO | EPO Fold Increase | VEGF (pg/ml) | VEGF Fold Increase |
|---|---|---|---|---|
| E* | 122 | ND | 66.5 | 1.58 |
| AC* | 294 | 2940 | 70 | 2.15 |
| F** | 2283 | 254 | 64 | 2.21 |
| G* | 162 | 270 | 86.5 | 2.46 |
| I* | 62.1 | 155.25 | 77.8 | 2.13 |
| AD** | 1997 | 27.4 | 66 | 2.54 |
| L** | 400.3 | 14.56 | 13 | 0.43 |
| AE** | 3825 | ND | 29 | 1.45 |
| M** | 161.6 | 179.56 | 38 | 1.31 |
| N** | 63.2 | 70.22 | 66 | 2.28 |
| AF** | 192 | 21.33 | 82 | 2.83 |
| O** | 157 | 174.44 | 64 | 2.21 |
| X** | 183 | ND | 48 | 2.40 |
| P** | 62.3 | 5.88 | 45 | 1.15 |
| Q** | 17.1 | 1.61 | 50 | 1.28 |
| AG** | 303 | 1.91 | 51 | 1.76 |
| AH** | 1242 | 11.61 | 44 | 1.76 |
| R** | 555.5 | 52.41 | 54 | 1.38 |

TABLE 3-continued

| Compound | EPO | EPO Fold Increase | VEGF (pg/ml) | VEGF Fold Increase |
|---|---|---|---|---|
| W** | 725.4 | 45.62 | 40 | 1.38 |
| S** | 460.6 | 40.76 | 15 | 0.68 |
| AI** | 221 | 1.96 | 20 | 0.91 |
| T** | 498 | 4.65 | 31 | 1.24 |
| AJ** | 271 | 2.53 | 29 | 1.16 |
| AK** | 2763 | 62.80 | 47 | 1.12 |
| AL** | 22514 | 187.62 | 130 | 2.06 |
| AM** | 28206 | 235.05 | 24 | 0.38 |
| AN** | 14964 | 26.16 | 39 | 1.05 |
| AO** | 12719 | 92.84 | 38 | 0.97 |
| AP** | 3595 | 20.08 | 27 | 0.43 |
| AQ** | 11464 | 23.78 | 59 | 1.69 |
| AR** | 11000 | 22.82 | 29 | 0.83 |
| AS** | 49305 | 102.29 | 20 | 0.57 |
| AT** | 169 | 3.84 | 43 | 1.02 |

*indicates assays measuring mouse EPO levels [mIU/ml] were done using a human EPO ELISA kit.
**indicates assays measuring mouse EPO levels [pg/ml] were done using a mouse EPO ELISA kit.
ND—not determined In another series of experiments, male Swiss Webster mice (29-34 g) were administered various compounds of the present invention via oral gavage using a ball-tipped gavage needle. Animals treated by oral gavage received a 4-10 ml/kg volume of either 0.5% carboxymethyl cellulose with or without 0.1% Polysorbate 80 (vehicle control) or various doses (6-60 mg/kg) of a compound of the present invention in 0.5% CMC, with or without 0.1% Polysorbate 80. Blood samples were collected and tissues were processed as described above. Six hours after injection, the animals were anesthetized and exsanguinated.

Plasma samples were collected in EDTA and heparin coated microtainer tubes. Plasma samples were assayed for erythropoietin and VEGF using commercially-available ELISA kits purchased from R & D Systems (Minneapolis Minn.).

As shown below in Table 4, administration of various compounds of the present invention by oral gavage to mice increased systemic levels of EPO and VEGF. These results indicated that methods and compounds of the present invention are useful for increasing expression of various cytoprotective and neuroprotective factors in vivo. These results further showed that systemic expression of cytoprotective and neuroprotective factors increased following oral administration of various compounds of the present invention.

TABLE 4

| Compound | EPO | EPO Fold Increase | VEGF (pg/ml) | VEGF Fold Increase |
|---|---|---|---|---|
| E* | 17.4 | ND | 65.4 | 1.63 |
| G* | 173 | 123.57 | 110.8 | 2.58 |
| I* | 21.4 | 16.46 | 62.7 | 2.71 |
| Y* | 11.5 | 8.85 | 52.7 | 2.28 |
| L** | 82.7 | 11.81 | 41 | 1.32 |
| M** | 8.8 | 1.26 | 38 | 1.23 |
| O** | 83.1 | 11.87 | 46 | 1.48 |
| X** | 41 | 5.86 | 36 | 1.16 |

*assays measuring mouse EPO levels [mIU/ml] were done using a human EPO ELISA kit.
**assays measuring mouse EPO levels [pg/ml] were done using a mouse EPO ELISA kit.
ND—not determined.

Example 5

Increased Expression of Cytoprotective and Neuroprotective Factors in Brain

The effect of compounds of the present invention on regulation of cytoprotective and neuroprotective gene expression in brain was evaluated. In one series of experiments, male Swiss Webster mice were administered by intravenous injection various compounds of the present invention. Animals treated by intravenous injection received a 6 ml/kg volume of either 5% Dextrose with an equimolar amount of Meglumine (vehicle control) or 20 mg/kg of a compound of the present invention in 5% dextrose with an equimolar amount of Meglumine Animals were euthanized four hours later and their brains placed in RNAlater (Ambion, Austin Tex.) for subsequent analysis. Tissues were homogenized in Trizol (Invitrogen, Carlsbad Calif.) using 5-mm steel beads in a Mixer Mill (Qiagen, Valencia Calif.). RNA was isolated from the Trizol solution and then further purified using RNeasy kit (Qiagen). cDNA was prepared from 1 mg total RNA using Omniscript reverse transcriptase (Qiagen) and random hexamers. Quantitative real time PCR was performed in a 7900HT instrument (Applied Biosystems, Foster City Calif.) using TaqMan Assays-on-Demand (Applied Biosystems). Gene expression levels were normalized to that of 18s RNA.

As shown below in Table 5, compounds of the present invention were effective at increasing gene expression of the cytoprotective and neuroprotective factors adrenomedullin (ADM), vascular endothelial growth factor (VEGF), and erythropoietin (EPO) in the brain. These results indicated that methods and compounds of the present invention are effective at increasing expression of cytoprotective and neuroprotective factors in the brain. These results further showed that expression of cytoprotective and neuroprotective factors in the brain increased following intravenous administration of the various compounds of the present invention.

TABLE 5

| Compound | ADM | VEGF | EPO |
|---|---|---|---|
| E | 1.7 | ND | 2.0 |
| Z | 3.7 | 2.1 | 1.3 |
| AA | 3.4 | 2.1 | 21.9 |
| AB | 2.5 | 2.1 | 6.8 |
| F | 2.1 | 1.5 | 3.1 |
| J | 2.7 | ND | 2.0 |
| AB | 1.9 | ND | 1.8 |
| AW | 4.9 | ND | 4.0 |
| G | 2.8 | ND | 3.8 |
| AA | 1.8 | ND | 0.9 |
| AV | 1.5 | ND | 1.9 |
| Z | 3.8 | 2.2 | 1.5 |
| AC | 1.3 | ND | 1.3 |
| AY | 1.0 | ND | 1.8 |

ND = not determined.

In another series of experiments, male Swiss Webster mice were administered various compounds of the present invention via oral gavage using a ball-tipped gavage needle. Animals treated by oral gavage received a 4-10 ml/kg volume of either 0.5% carboxymethyl cellulose with or without 0.1% Polysorbate 80 (vehicle control) or various doses (20-60 mg/kg) of a compound of the present invention in 0.5% CMC, with or without 0.1% Polysorbate 80. Animals were euthanized six hours later and their brains placed in RNAlater (Ambion, Austin Tex.) for subsequent analysis.

Tissues were homogenized in Trizol (Invitrogen, Carlsbad Calif.) using 5-mm steel beads in a Mixer Mill (Qiagen, Valencia Calif.). RNA was isolated from the Trizol solution and then further purified using RNeasy kit (Qiagen). cDNA was prepared from 1 mg total RNA using Omniscript reverse transcriptase (Qiagen) and random hexamers. Quantitative real time PCR was performed in a 7900HT instrument (Applied Biosystems, Foster City Calif.) using TaqMan Assays-on-Demand (Applied Biosystems). Gene expression levels were normalized to that of 18s RNA.

As shown below in Table 6, compounds of the present invention were effective at increasing gene expression of ADM, VEGF, and EPO in the brain. These results indicated that methods and compounds of the present invention are effective at increasing expression of cytoprotective and neuroprotective factors in the brain. These results further showed that expression of cytoprotective and neuroprotective factors in the brain increased following oral administration of the various compounds of the present invention.

TABLE 6

| Compound | ADM | VEGF | EPO |
|---|---|---|---|
| R | 1.7 | 1.3 | ND |
| W | 1.8 | 1.8 | ND |
| AZ | 1.1 | 1.1 | 1.1 |
| A | 0.7 | 0.7 | 1.6 |
| BC | 1.1 | 1.0 | 2.3 |
| BB | 1.3 | 0.9 | 2.1 |
| S | 1.7 | 1.1 | 1.5 |
| BD | 1.6 | 1.0 | 1.6 |
| BA | 1.6 | 1.1 | 1.9 |
| AL | 1.6 | 1.2 | 2.0 |
| AM | 1.3 | 0.9 | 3.2 |
| F | 2.0 | 1.3 | 5.2 |
| AX | 2.0 | 1.9 | 1.0 |

ND = not determined.

Example 6

Reduction of Infarct Volume and Edema in a Mouse Model of Permanent Middle Cerebral Artery Occlusion (pMCAO)

The effect of compounds of the present invention on infarct volume and edema associated with stroke was examined in an animal model of ischemic stroke. In these studies, mice were subjected to permanent occlusion of the middle cerebral artery. Mice were anesthetized intraperitoneally with avertin (0.5 mg/g). Mice were then immobilized in a rodent stereotaxic frame (Kopf Instruments, Tujunga Calif.) and maintained with avertin as needed. The surgical area of the head was swabbed with 70% ethanol and a lateral incision was made between the right orbit and the right ear. The superior pole of the parotid gland was reflected downward, as was the temporalis after partial resection of its cranial insertion. The distal course of the middle cerebral artery (MCA) was visible through the translucent skull. A small burr-hole craniotomy was performed with a microdrill (Fine Science Tools, Foster City Calif.). The meninges/dura was removed and the MCA was coagulated by bipolar diathermy. The muscle and soft tissue were replaced and the incision closed with vet-bond adhesive (3M, St. Paul Minn.). These studies were performed in two different mouse models of pMCAO as described below.

pMCAO in C57BL/6 Mice

In one series of experiments, male C57BL/6 mice (25-35 g) were subjected to permanent occlusion of the MCA as described above. Compounds of the present invention were administered by intravenous injection at various times before or after MCA occlusion (see Table 7). Animals administered compound by intravenous injection received a 6 ml/kg volume of either 5% Dextrose with an equimolar amount of Meglumine (vehicle control) or 20-60 mg/kg of a compound of the present invention in 5% dextrose with an equimolar amount of Meglumine. Body temperature of the animals was maintained by use of a heating pad both during and after surgery. Twenty-four hours after MCA occlusion animals were euthanized with $CO_2$ and their brains removed. After removal, the brain was sliced in 7 coronal sections, each 1 mm thick. The sections were placed rostral side down in a petri dish and stained with 1% Triphenyl tetrazolium chloride for 20 minutes at 37° C. for determination of infarct volume. Brain sections were then digitally photographed and analyzed for changes in infarct volume and extent of edema. Infarct volumes were determined by measuring the infarcted (i.e., non-stained) areas of each brain section and multiplying this value by the section thickness. Extent of edema was determined by the net increase in volume of the ipsilateral cortex compared to that of the contralateral cortex of brain sections.

As shown below in Table 7, compounds of the present invention reduced infarct volume and extent of edema in an animal model of permanent middle cerebral artery occlusion compared to that observed in non-treated control animals. These results indicated that methods and compounds of the present invention are useful for treating ischemic stroke. Additionally, these results showed that administration of compounds of the present invention at the time of MCA occlusion or 4 hours following MCA occlusion was effective at reducing infarct volume and extent of edema. Taken together, these results indicated that compounds of the present invention are effective for reducing brain tissue damage (e.g., infarct volume and edema) associated with stroke when administered up to at least 4 hours after onset of stroke.

TABLE 7

| Compound | Percent Reduction in Infarct Volume | Percent Reduction in Edema | Time of Compound Administration |
|---|---|---|---|
| E | 51 | 54 | −6 hr |
| P | 37 | ND | 0 hr |
| F | 68 | 47 | 0 hr |
| AC | 17 | ND | 0 hr |
| N | 46 | ND | 0 hr |
| AF | 21 | ND | 0 hr |
| O | 31 | ND | 0 hr |
| X | 36 | ND | 0 hr |
| R | 32 | ND | 0 hr |
| AK | 13 | −12* | 0 hr |
| AS | 50 | 54 | 0 hr |
| AL | 43 | 73 | 0 hr |
| AM | 71 | ND | 4 hr |
| AN | 46 | ND | 4 hr |
| AO | 55 | ND | 4 hr |
| AE | 63 | ND | 4 hr |
| E | 9 | ND | 4 hr |
| G | 48 | ND | 4 hr |
| L | 48 | ND | 4 hr |

*indicates that the increase in the extent of edema was not statistically significant
ND = not determined.

The effect of compounds of the present invention administered at various times following the onset of stroke was examined further as follows. In these studies, changes in infarct volume were measured using an animal model of stroke when compounds of the present invention were administered from 0 to 8 hours following permanent MCA occlusion. In one series of experiments, male C57BL/6 mice (25-35 g) were subjected to permanent occlusion of the MCA as described above. Compound F was administered to the animals by a single intravenous bolus injection at various times up to 5 hours after MCA occlusion (see Table 8 below). Animals administered compound by intravenous injection received a 6 ml/kg volume of either 5% Dextrose with an equimolar amount of NaOH (vehicle control) or 60 mg/kg of Compound F in 5% dextrose with an equimolar amount of NaOH. Body temperature of the animals was maintained by use of a heating pad both during and after surgery. Changes in infarct volumes were determined as described above.

As shown below in Table 8, administration of Compound F at various times following MCA occlusion reduced infarct volume in an animal model of permanent middle cerebral artery occlusion compared to that of non-treated control animals. In particular, administration of Compound F at 0, 1, 3, and 5 hours following MCA occlusion resulted in a reduction of infarct volume of 50%, 62%, 53%, and 55%, respectively, compared to that observed in non-treated control animals. These results indicated that methods and compounds of the present invention are useful for treating ischemic stroke. Additionally, these results showed that compounds of the present invention are effective at reducing infarct volume associated with stroke when administered 0, 1, 3, and 5 hours following onset of stroke. Taken together, these results showed that compounds of the present invention are effective at reducing infarct volume, and therefore effective for treatment of stroke, when administered up to at least 5 hours following the onset of stroke.

TABLE 8

| Time of Compound F Administration after MCA Occlusion | Percent Reduction in Infarct Volume |
| --- | --- |
| 0 hr | 50 |
| 1 hr | 62 |
| 3 hr | 53 |
| 5 hr | 55 |

In another set of experiments, male C57BL/6 mice (25-35 g) were subjected to permanent occlusion of the MCA as described above. Compound F was administered by single intravenous bolus injection at various times up to 8 hours after MCA occlusion (see Table 9 below). Animals administered compound by intravenous injection received a 6 ml/kg volume of either 5% Dextrose with an equimolar amount of Meglumine (vehicle control) or 60 mg/kg of Compound F in 5% dextrose with an equimolar amount of Meglumine. Body temperature of the animals was maintained by use of a heating pad both during and after surgery. Changes in infarct volumes were determined as described above.

As shown below in Table 9, administration of Compound F at various times following MCA occlusion reduced infarct volume in an animal model of permanent middle cerebral artery occlusion compared to that of non-treated control animals. In particular, administration of Compound F at 0, 4, 6, and 8 hours following MCA occlusion resulted in a reduction of infarct volume of 43%, 36%, 15%, and 8%, respectively, compared to that observed in non-treated control animals. These results indicated that methods and compounds of the present invention are useful for treating ischemic stroke. Additionally, these results showed that compounds of the present invention are effective at reducing infarct volume associated with stroke when administered 0, 4, 6, and 8 hours following onset of stroke. Taken together, these results showed that compounds of the present invention are effective at reducing infarct volume, and therefore effective for treatment of stroke, when administered up to at least 8 hours following the onset of stroke.

TABLE 9

| Time of Compound F Administration after MCA Occlusion | Percent Reduction in Infarct Volume |
| --- | --- |
| 0 hr | 43 |
| 4 hr | 36 |
| 6 hr | 15 |
| 8 hr | 8 | pMCAO in db/db Mice

Diabetes is an established risk factor for stroke and is associated with a greater degree of tissue damage following an ischemic insult compared to that observed in non-diabetic subjects. In addition, diabetic subjects who have had a stroke have higher mortality rates, poorer neurological outcomes, and more severe long-term disabilities compared to that observed in non-diabetic stroke subjects. Therefore, the effect of compounds of the present invention on infarct volume and edema associated with stroke was examined in db/db mice, an established animal model of noninsulin dependent (Type 2) diabetes. (See Kaarisalo et al., (2005) Diabetes Res and Clin Pract, 69:293-298; see Vannucci et al., (2001) J Cereb Blood Flow Metab, 21:52-60.)

To evaluate the effect of compounds of the present invention on infarct volume in an animal model of diabetes, db/db mice were subjected to ischemic stroke. Eight week-old male db/db mice were subjected to permanent occlusion of the MCA as described above. Compound F (20 mg/kg) or vehicle-control was administered by intravenous injection immediately after MCA occlusion. Body temperature of the animals was maintained by use of a heating pad both during and after surgery. Twenty-four hours after MCA occlusion animals were euthanized with $CO_2$ and their brains removed. Changes in infarct volumes were determined as described above.

Diabetic animals subjected to permanent occlusion of the MCA and administered Compound F showed a 52% reduction in infarct volume compared that observed in non-treated control diabetic animals. These results showed that the methods and compounds of the present invention are effective at reducing infarct volume and for treatment of stroke in diabetic subjects.

Example 7

Rat Model of Permanent Middle Cerebral Artery Occlusion (pMCAO)

Male Wistar rats (250-320 g) are used for this study. Animals are anesthetized with Isoflurane (3% induction, 1-2% maintenance). Anesthesia is monitored by toe pinch. Aseptic technique is used for all procedures during this study. The surgical site is clipped and cleaned with alcohol and surgical scrub. The animal is placed on a warm water heating pad to maintain body temperature. A paramedian incision is made on the neck over the carotid artery. The tissue is bluntly dissected away to reveal the carotid artery and the bifurcation. Sutures are placed around the proximal portion or the common carotid and the external carotid arteries. These sutures are tied off. An incision is made in the common carotid, distal to the ligation. A pre-prepared filament (4-0 monofilament suture or like material) is placed in the carotid and advanced into the internal carotid artery. The filament is advanced ~20 mm past the carotid bifurcation until slight resistance is felt as it wedges in the middle cerebral artery. Care must be taken to not rupture the artery upon insertion of the filament. The filament is tied in place and the skin incision closed. The animal is evaluated when awake for successful occlusion using the Bederson scale as previously described. (See Bederson et al., (1986) Stroke, 17:1304-1308.) Body temperature is taken every 15 minutes to maintain normothermia. Animals that have undergone the MCAO procedure may have difficulty in thermoregulation for a few hours after surgery Animals are placed in a cooling or heating box as determined by their temperature. Body temperature is maintained at 37.5° C. Animals are monitored for 6 hours following MCAO and are then placed in cages overnight. Twenty-four hours after MCAO animals are euthanized with $CO_2$ and their brains removed. After removal, the brain is sliced in 7 coronal slices, 2 mm thick and the slices placed rostral side down in a petri dish. The slices are then stained with 1% Triphenyl tetrazolium chloride for 20 minutes at 37° C. for determination of infarct size. Brain slices are photographed and analyzed for infarct size, infarct volume, penumbra, and edema.

Example 8

Mouse Model of Transient Middle Cerebral Artery Occlusion (tMCAO)

Male C57Bl6 mice (25-30 g) are used in this study. Mice are anesthetized with Isoflurane (3% induction, 1-2% maintenance). The surgical site is clipped and cleaned with alcohol and surgical scrub. A midline neck incision is made over the carotid artery and the artery is dissected to its bifurcation. A monofilament suture is introduced into the internal carotid artery and advanced until it lodges in the middle cerebral artery. The suture is tied in placed and the incision is closed. Two hours after occlusion the mice will be re-anesthetized and the suture will be removed from the MCA. Body temperature is maintained by use of a heating pad both during and after surgery. Animals are monitored for 4 hours following MCAO. Twenty-four hours later, the animals will be euthanized and the brains harvested. Brains are sliced in 1 mm coronal sections and stained with Triphenyl tetrazolium chloride for determination of infarct volume and extent of edema.

Example 9

Recruitment of Progenitor Cells in Mice

Male C57Bl6 mice (25-30 g) are used in this study. Mice are anesthetized with Isoflurane (3% induction, 1-2% maintenance). The surgical site is clipped and cleaned with alcohol and surgical scrub. A midline neck incision is made over the carotid artery and the artery is dissected to its bifurcation. A monofilament suture is introduced into the internal carotid artery and advanced until it lodges in the middle cerebral artery. The suture is tied in placed and the incision is closed. Two hours after occlusion the mice will be re-anesthetized and the suture will be removed from the MCA. Body temperature is maintained by use of a heating pad both during and after surgery. To detect proliferating cells, cell proliferation-specific marker, BrdU (Sigma-Aldrich, St. Louis Mo.), is administered intraperitoneally (50 mg/kg) daily, beginning 24 hours following transient MCAO until the day prior to sacrifice (day 14). After 14 days, the animals are euthanized and the brains harvested. Brains sections are prepared and stained for BrdU using immunohistochemical techniques. Cell proliferation in regions associated with or adjacent to the infarct area and penumbra is confirmed by the presence of BrdU positive cells. Brain sections are also stained for BrdU in combination with markers specific for neuronal, glial, endothelial, and microglial cell types.

Example 10

Rat Model of Transient Middle Cerebral Artery Occlusion (tMCAO)

The effect of compounds of the present invention on infarct volume and edema was examined in an animal model of ischemic stroke. For these studies, male Wistar rats (320 g) were subjected to transient occlusion of the middle cerebral artery. Rats were anesthetized with 3% isoflurane in oxygen. Aseptic technique was used for all procedures during these studies. The surgical site was clipped and cleaned with alcohol and surgical scrub. Each animal was placed on a warm water heating pad to maintain body temperature. A paramedian incision was made on the neck over the carotid artery. The tissue was bluntly dissected away to reveal the carotid artery and the carotid artery bifurcation. Sutures were placed around the proximal portion of the common carotid and the external carotid arteries and were then tied off. An incision was made in the common carotid, distal to the ligation and a pre-prepared filament (3-0 monofilament suture or like material) was placed in the carotid and advanced into the internal carotid artery. The filament was advanced approximately 20 millimeters past the carotid bifurcation until slight resistance was felt as it wedged inside the middle cerebral artery (MCA). Care was taken to not rupture the artery upon insertion of the filament. The filament was tied in place and the skin incision closed. At this time isoflurane was discontinued and the animals were allowed to awaken.

One hour after surgery, the success of MCA occlusion was assessed using the Bederson scale, as previously described. (See Bederson et al., (1986) Stroke, 17:1304-1308.) Sixty minutes after occlusion, the animals were re-anesthetized for reperfusion. The skin incision was reopened and the filament was carefully withdrawn from the MCA but not completely removed. Body temperature was taken every 15 minutes throughout the study to maintain normothermia. Animals that have undergone the MCA occlusion procedure may have difficulty in thermoregulation for a few hours after surgery. Animals were placed in a cooling or heating box as determined by their body temperature. Body temperature was maintained at 37.5° C.

Various compounds of the present invention were administered by oral gavage (p.o.) at reperfusion or at reperfusion and again at 24 hours after reperfusion in 0.5% CMC and 0.1% Polysorbate 80 at various doses (see Table 10 below). Forty-eight hours after MCA occlusion animals were euthanized with $CO_2$ and their brains removed. After removal, the brain was sliced into 7 coronal sections, 2 mm thick. The sections were placed rostral side down in a petri dish and stained with 1% Triphenyl tetrazolium chloride for 20 minutes at 37° C. for determination of infarct volume. Brain sections were then digitally photographed and analyzed for changes in infarct volume and extent of edema. Infarct volumes were determined by measuring the infarcted (i.e., non-stained) areas of each brain section and multiplying this value by the section thickness. Extent of edema was determined by the net increase in volume of the ipsilateral cortex compared to that of the contralateral cortex of brain sections.

As shown below in Table 10, administration of compounds of the present invention at the time of reperfusion reduced infarct volume and edema in an animal model of transient middle cerebral artery occlusion compared to that observed in non-treated control animals.

TABLE 10

| Compound | Dosage (mg/kg) | Percent Reduction in Infarct Volume | Percent Reduction in Edema |
| --- | --- | --- | --- |
| F | 60 | 70 | 39 |
| AS | 6 | 58 | 32 |
| AL | 6 | 51 | 12 |

As shown below in Table 11, animals administered two doses (60 mg/kg) of Compound F (one dose administered at the time of reperfusion and a second dose administered 24 hours later) showed a greater reduction in infarct volume and a greater decrease in the extent of edema compared to that observed in animals that received only a single dose of compound administered at reperfusion.

TABLE 11

| Compound Administration | Percent Reduction in Infarct Volume | Percent Reduction in Edema |
| --- | --- | --- |
| 1 Dose | 42 | 28 |
| 2 Doses | 70 | 39 |

These results indicated that methods and compounds of the present invention are useful for treating stroke. Additionally, these results showed administration of compounds of the present invention after an ischemic insult are effective at limiting brain tissue damage associated with stroke and are therefore useful for treating stroke.

In another series of experiments, the long term effect of administration of compounds of the present invention on stroke and brain tissue damage associated with stroke was examined. For these studies, the effect of compounds of the present invention on lesion area, neuronal degeneration, and brain tissue loss following stroke was examined 28 days after transient MCA occlusion. Wistar rats (320 g) were subjected to transient occlusion of the MCA as described above. Compound F (60 mg/kg) was administered by oral gavage at 1.5 hours and 24 hours after reperfusion and subsequently every other day (using a dose of 30 mk/kg, p.o.) for 28 days. Twenty-eight days after transient MCA occlusion, animals were anesthetized with 3% isoflurane in oxygen and transcardially perfused with 100 ml of 0.9% saline solution (Hospira Inc, Lake Forest Ill.). Brains were removed and sliced into 6 coronal sections, 2 mm thick, and embedded in cryomold standard (Sakura Finetek, Ca) using O.C.T. embedded medium (Sakura Finetek, Ca). Twenty micron thick sections were cut from each coronal section and stained with Fluoro-Jade B (according to the manufacturer's protocol) which reveals areas of dying or degenerating neurons. Stained sections were digitally photographed under fluorescent or brightfield light as described below for determination of lesion area, extent of neuronal degeneration, and area of tissue loss. (See Schmued et al., (1997) Brain Res, 751:37-46.)

Changes in lesion area were measured as follows. Digital photographs of Fluoro-Jade B stained sections taken under brightfield light were used to measure lesion area. Lesion area was determined by measuring the infarcted (i.e., non-Fluoro-Jade B stained) areas of each brain section. Values are presented as a percentage of lesion area using the following calculation: [Area of infarct (lesion)/Area of ischemic hemisphere (ipsilateral)]×100.

Changes in neuronal degeneration were measured as follows. Digital photographs of Fluoro-Jade B stained sections taken under fluorescent light were used to measure areas of neuronal degeneration. Fluoro-Jade B positive cells observed in the digital photographs were quantified using Image Pro-Plus image analysis software (Media Cybernetics, Silver Spring Md.). Extent of neuronal degeneration was determined by comparing the total number of Fluoro-Jade B positive cells per $mm^2$ area of the treated group to the same area of the corresponding vehicle-control group. The distance of each coronal section from bregma was determined.

Changes in area of brain tissue loss were measured as follows. Digital photographs of Fluoro-Jade B stained sections taken under brightfield light were used to measure area of tissue loss. Using image analysis software, areas for the contralateral (i.e. non-ischemic) and ipsilateral (i.e. ischemic) hemisphere were obtained. Area of brain tissue loss, associated with the ischemic insult, was measured by subtracting the area of the contralateral hemisphere from the area of the ipsilateral hemisphere. A percentage value was then determined by dividing the area of brain tissue loss associated with the stroke by the total area of the contralateral hemisphere. [Area of Non-ischemic hemisphere (contralateral)−Area of ischemic hemisphere (ipsilateral)/Area of Non-ischemic hemisphere (contralateral)]×100.)

Figure 2:
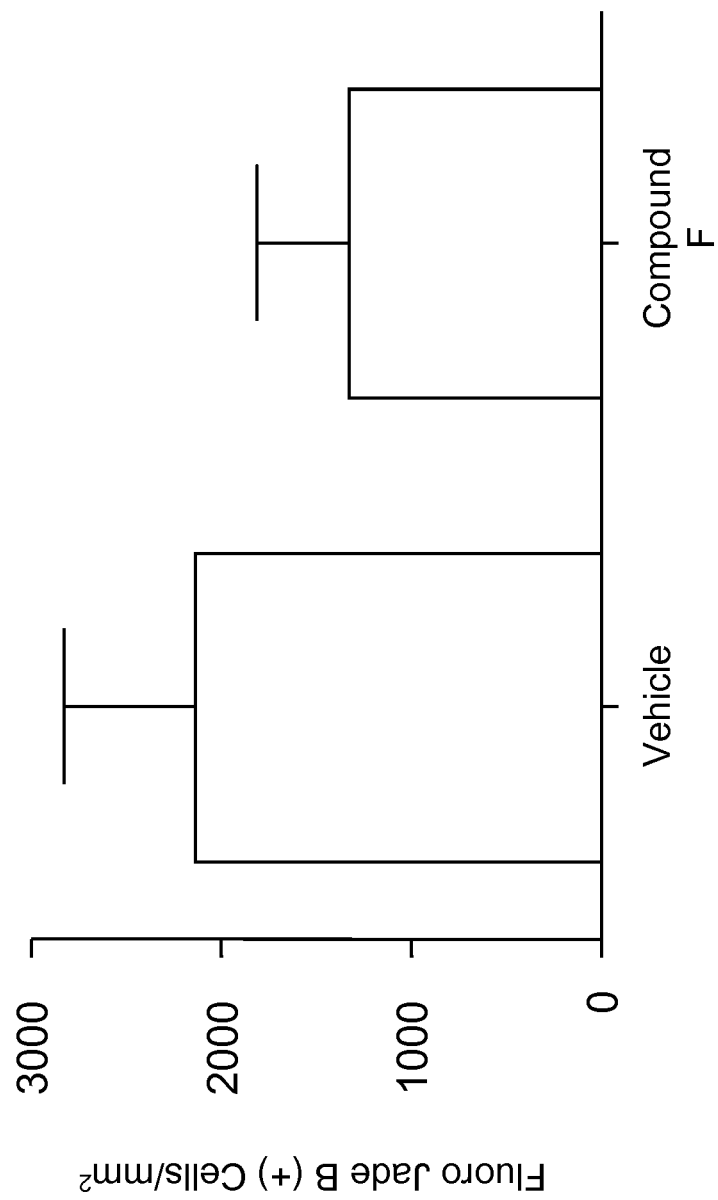
FIG. 2 sets forth data showing methods and compounds of the present invention reduced neuronal degeneration in the brain in a transient middle cerebral artery occlusion animal model of stroke.
Figure 3:
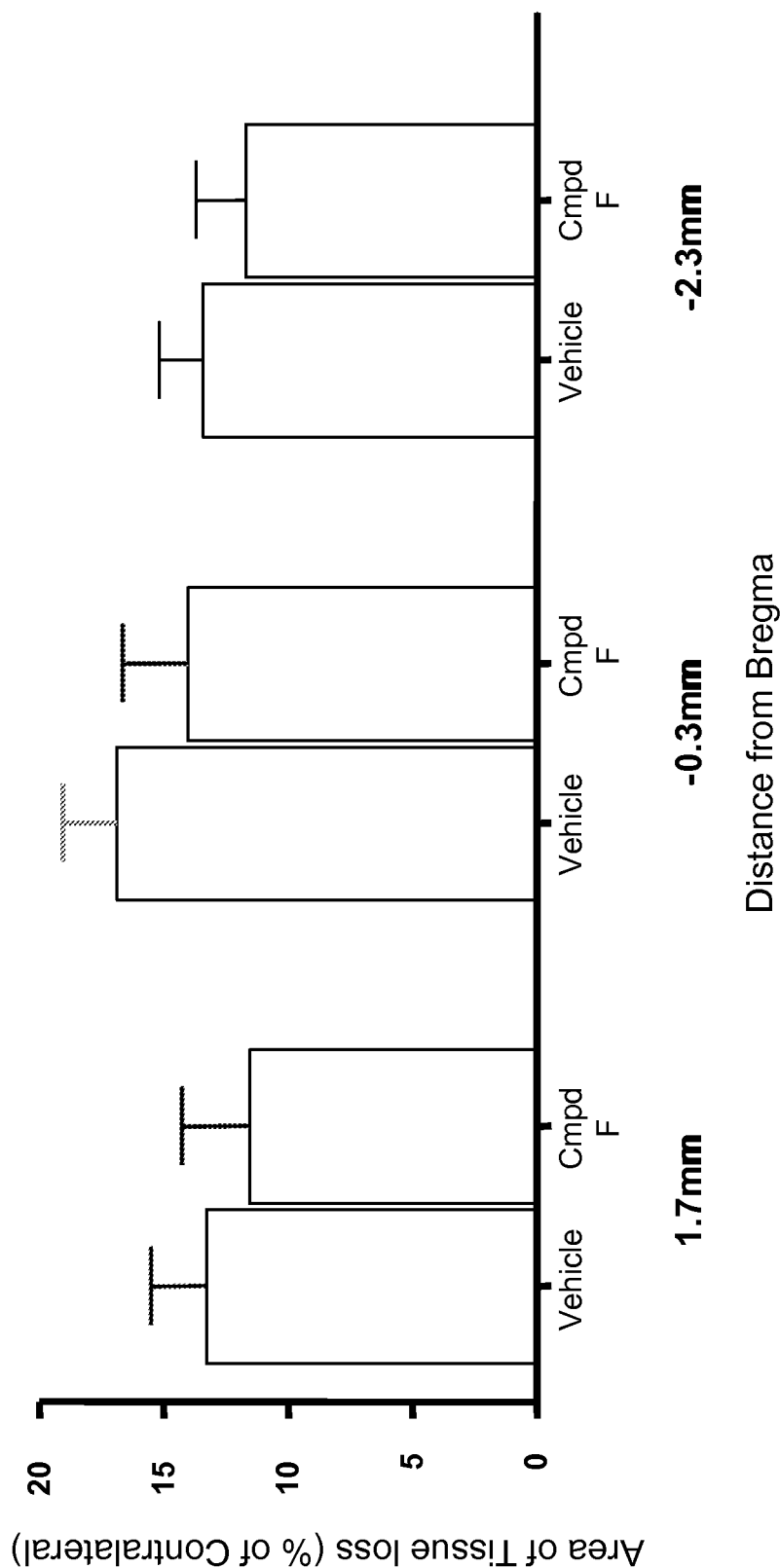
FIG. 3 sets forth data showing methods and compound of the present invention reduced the area of tissue loss in the brain in a transient middle cerebral artery occlusion animal model of stroke.

As shown in FIG. 1, FIG. 2, and FIG. 3, animals administered Compound F following transient middle cerebral artery occlusion showed reduced lesion area, neuronal degeneration, and brain tissue loss, respectively, compared to that observed in non-treated control animals 28 days after ischemic insult. Lesion area, neuronal degeneration, and area of brain tissue loss measurements are shown for non-treated vehicle control animals and for animals administered Compound F. Lesion area shown in FIG. 1 is presented as the percent area of positive stained ipsilateral brain hemisphere determined at various distances from the bregma. Neuronal degeneration shown in FIG. 2 is presented as the number of Fluoro-Jade B positive cells per $mm^2$ area. Area of brain tissue loss shown in FIG. 3 is presented as the percentage of the contralateral hemisphere. Lesion area, neuronal degeneration, and area of brain tissue loss measurements are shown in FIG. 1, FIG. 2, and FIG. 3 for non-treated vehicle control animals and for animals administered Compound F.

These results showed that methods and compounds of the present invention were effective at providing long term benefit for brain tissue damage associated with stroke. Taken together, these results indicated that methods and compounds of the present invention are useful for reducing both immediate and long-term brain tissue damage associated with stroke.

Example 11

Behavioral Testing in Rat Model of Transient Middle Cerebral Artery Occlusion (tMCAO)

Rats subjected to cerebral ischemia following transient MCA occlusion have deficits in sensorimotor and neuromuscular function which can be assessed using various behavioral tests. (See, e.g., Aronowski et al. J Cereb Blood Flow Metab (1996) 16:705-713; and Colbourne et al. J Cereb Blood Flow Metab (2000) 20:1702-1708.) The effect of compounds of the present invention on various functional impairments associated with stroke was examined using an animal model of ischemic stroke. In this series of experiments, male Wistar rats (300 g) underwent behavioral testing after transient MCA occlusion. One day prior to MCAO surgery, the rats were trained to the grip strength meter and subjected to tactile adhesion testing. Following their training, rats were subjected to transient occlusion of the MCA in the same manner described in Example 10 above. Compound F (60 mg/kg, p.o.) was administered by oral gavage at 1.5 hours and 24 hours after reperfusion and then every other day (with a dose of 30 mk/kg, p.o.) for 28 days.

Assessment of functional impairments following stroke was performed using two behavioral tests—a tactile adhesion test and a grip strength test—during the 28 days following transient occlusion of the middle cerebral artery. Both behavioral tests (described below) were performed on rats at 1, 3, 7, 14, and 28 days after onset of transient MCA occlusion.

Tactile Adhesion Test

A tactile adhesion test was used to measure sensorimotor deficits and function. A tactile stimulus (1 cm$^2$ of "sticky tape") was applied to the dorsal side of each animal's forelimbs. The latency (i.e. time required for the animal to remove each stimulus from the forelimbs) was recorded for ipsilateral (right) and contralateral (left) forelimbs separately. Three trials separated by 5 minutes were carried out for each rat and mean latency values in seconds (sec) were recorded.

Grip Strength

Grip strength was used to assess neuromuscular function. Rat grip strength was determined using a standard rodent grip strength meter (Columbus Instruments, Columbus Ohio). Briefly, rats were held by an investigator and allowed to flex their forepaws and grasp a trapeze bar connected to an electronic sensor. Grip strength was assessed with a gentle consistent pull in the caudal direction. The digital reading on the meter was recorded and the mean of three trials reported. Grip strength of both contralateral (left) and ipsilateral (right) forelimbs was tested.

Figure 4:
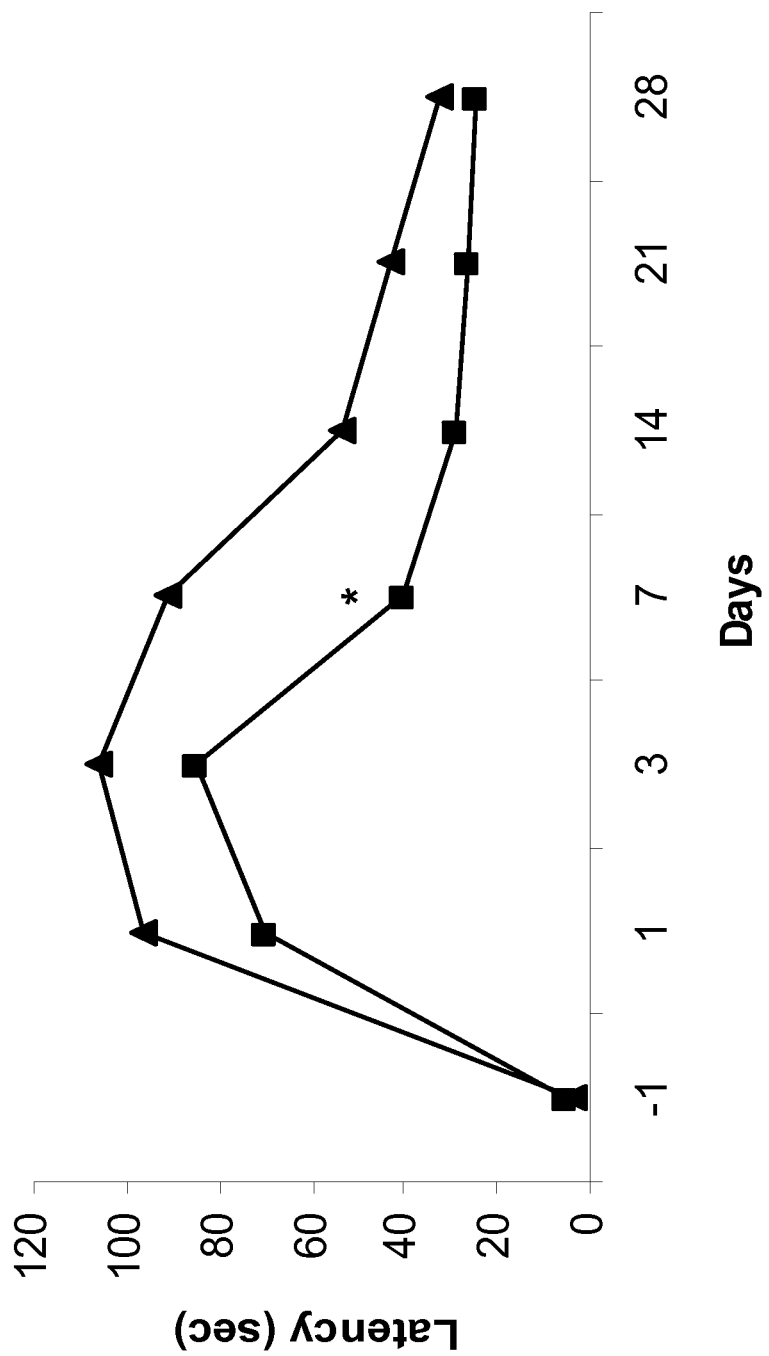
FIG. 4 sets forth data showing methods and compounds of the present invention improved sensorimotor function in a transient middle cerebral artery occlusion animal model of stroke.

As shown in FIG. 4, administration of Compound F significantly improved latency in the tactile adhesion test at day 7 in pMCAO animals compared to latency observed in non-treated control pMCAO animals. (Data in FIG. 4 is presented as latency in seconds in a tactile adhesion test for non-treated control animals (triangles in FIG. 4) and for animals administered Compound F (squares in FIG. 4). In FIG. 4, * indicates a significant difference in latency was observed in compound-treated animals compared to non-treated control animals.) These results indicated that methods and compounds of the present invention are useful for reducing sensorimotor deficits associated with and following stroke.

Figure 5:
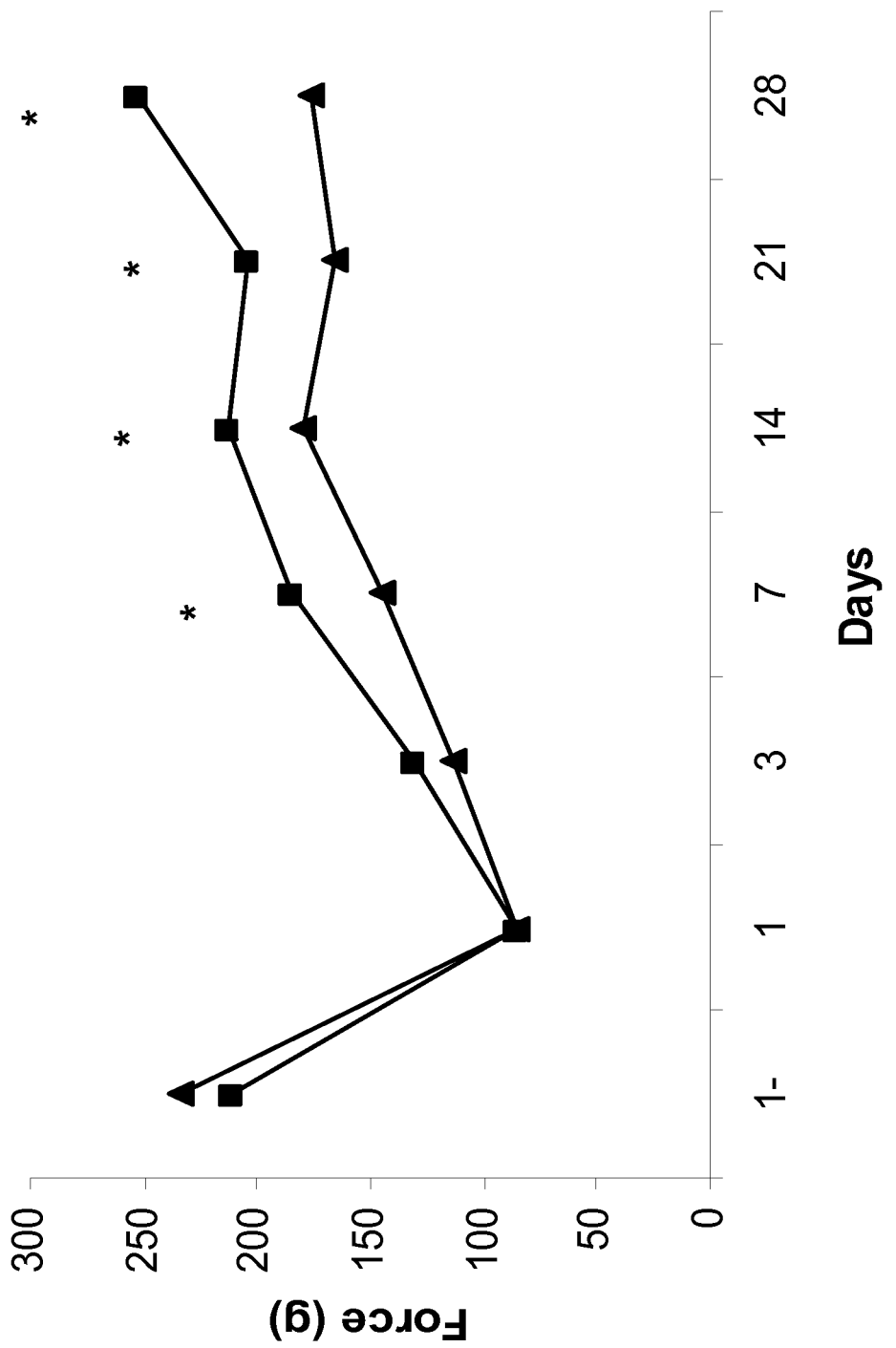
FIG. 5 sets forth data showing methods and compounds of the present invention improved neuromuscular function in a transient middle cerebral artery occlusion animal model of stroke.

As shown in FIG. 5, administration of Compound F significantly improved grip strength on days 7, 14, 21, and 28 in pMCAO animals compared to grip strength observed in non-treated control pMCAO animals. (In FIG. 5, data from non-treated control animals (triangles) and animals administered Compound F (squares) are presented. In FIG. 5, * indicates a significant difference in grip strength was observed in treated animals compared to non-treated control animals.) These results demonstrated that methods and compounds of the present invention are useful for reducing neuromuscular deficits associated with and following stroke. Taken together, these results indicated that methods and compounds of the present invention are useful for treating stroke. Additionally, these results showed administration of compounds of the present invention after an ischemic insult improved functional recovery and recovery of motor function and are therefore useful for treating stroke.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for treating a subject suspected of having had a stroke, prior to diagnosis of the stroke as an ischemic stroke or a hemorrhagic stroke, the method comprising the steps of:
    a) administering a first dose of a compound which inhibits hypoxia inducible factor (HIF) prolyl hydroxylase activity to the subject; and
    b) subsequently diagnosing the stroke as an ischemic stroke or a hemorrhagic stroke,
    wherein if the subject is subsequently diagnosed as having had an ischemic stroke, the method further comprises the additional step of: administering a thrombolytic agent to the subject, wherein the administering of the thrombolytic agent occurs at least 3 hours after onset of the stroke.

2. The method of claim 1, wherein the compound is a 2-oxoglutarate mimetic.

3. The method of claim 1, wherein the treating comprises amelioration of brain tissue damage.

4. The method of claim 3, wherein the brain tissue damage is selected from the group consisting of infarct volume, edema, neuronal degeneration, a lesion, and brain tissue loss.

5. The method of claim 1, wherein the step of administering for first dose occurs at least 'hours after onset of the stroke.

6. The method of claim 1, wherein the thrombolytic agent is tissue plasminogen activator (tPA).

7. The method of claim 1, wherein the subject is subsequently diagnosed as having had an ischemic stroke and the method further comprises the additional step of: administering a second dose of compound at or subsequent to reperfusion.

8. The method of claim 7, wherein the administering of the second dose of the compound occurs at least 24 hours after administrating the first dose.

9. The method of claim 1, wherein the subject has diabetes.

10. The method of claim 1, wherein the compound is a heterocyclic carboxamide.

* * * * *